United States Patent
Osborn et al.

(10) Patent No.: US 12,343,397 B2
(45) Date of Patent: Jul. 1, 2025

(54) DRUG-RESISTANT IMMUNE CELLS AND METHODS OF USE THEREOF

(71) Applicant: Regents of the University of Minnesota, Minneapolis, MN (US)

(72) Inventors: Mark J. Osborn, St. Louis Park, MN (US); Keli Hippen, Minneapolis, MN (US); Bruce R. Blazer, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1156 days.

(21) Appl. No.: 17/056,233

(22) PCT Filed: May 16, 2019

(86) PCT No.: PCT/US2019/032686
§ 371 (c)(1),
(2) Date: Nov. 17, 2020

(87) PCT Pub. No.: WO2019/222513
PCT Pub. Date: Nov. 21, 2019

(65) Prior Publication Data
US 2021/0213062 A1    Jul. 15, 2021

Related U.S. Application Data

(60) Provisional application No. 62/672,868, filed on May 17, 2018.

(51) Int. Cl.
| | | |
|---|---|---|
| *A61P 37/06* | (2006.01) | |
| *A61K 31/436* | (2006.01) | |
| *A61K 31/573* | (2006.01) | |
| *A61K 35/28* | (2015.01) | |
| *A61K 38/13* | (2006.01) | |
| *A61K 40/10* | (2025.01) | |
| *A61K 40/11* | (2025.01) | |
| *A61K 40/22* | (2025.01) | |
| *A61K 40/41* | (2025.01) | |
| *A61K 45/06* | (2006.01) | |
| *C07K 14/705* | (2006.01) | |
| *C12N 5/0783* | (2010.01) | |
| *C12N 9/16* | (2006.01) | |
| *C12N 9/22* | (2006.01) | |
| *C12N 15/11* | (2006.01) | |
| *C12N 15/90* | (2006.01) | |

(52) U.S. Cl.
CPC ............ *A61K 45/06* (2013.01); *A61K 31/436* (2013.01); *A61K 31/573* (2013.01); *A61K 35/28* (2013.01); *A61K 38/13* (2013.01); *A61K 40/10* (2025.01); *A61K 40/11* (2025.01); *A61K 40/22* (2025.01); *A61K 40/418* (2025.01); *A61P 37/06* (2018.01); *C07K 14/705* (2013.01); *C12N 5/0637* (2013.01); *C12N 9/16* (2013.01); *C12N 9/22* (2013.01); *C12N 15/11* (2013.01); *C12N 15/907* (2013.01); *C12Y 301/03016* (2013.01); *A61K 2239/31* (2023.05); *A61K 2239/38* (2023.05); *C12N 2310/20* (2017.05); *C12N 2800/80* (2013.01)

(58) Field of Classification Search
CPC ........ A61K 35/17; A61K 35/28; A61K 38/13; A61P 37/06
See application file for complete search history.

(56) References Cited

U.S. PATENT DOCUMENTS

| | | |
|---|---|---|
| 4,690,915 A | 9/1987 | Rosenberg |
| 4,797,368 A | 1/1989 | Carter et al. |
| 5,139,941 A | 8/1992 | Muzyczka et al. |
| 5,399,346 A | 3/1995 | Anderson et al. |
| 5,580,859 A | 12/1996 | Felgner et al. |
| 5,589,466 A | 12/1996 | Felgner et al. |
| 5,858,358 A | 1/1999 | June et al. |
| 5,883,223 A | 3/1999 | Gray |
| 5,993,434 A | 11/1999 | Dev et al. |
| 5,994,136 A | 11/1999 | Naldini et al. |
| 6,013,516 A | 1/2000 | Verma et al. |
| 6,181,964 B1 | 1/2001 | Hofmann et al. |
| 6,233,482 B1 | 5/2001 | Hofmann et al. |
| 6,241,701 B1 | 6/2001 | Hofmann |
| 6,326,193 B1 | 12/2001 | Liu et al. |
| 6,352,694 B1 | 3/2002 | June et al. |
| 6,516,223 B2 | 2/2003 | Hofmann |

(Continued)

FOREIGN PATENT DOCUMENTS

| | | |
|---|---|---|
| WO | WO 1993003769 | 3/1993 |
| WO | WO 1993009239 | 5/1993 |

(Continued)

OTHER PUBLICATIONS

Summers et al., (Blood (2016) 128 (22): 1159) (Year: 2016).*
Dimeloe et al., "Regulatory T cells, inflammation and the allergic response: The role of glucocorticoids and Vitamin D," J. Steroid Biochem. Mol. Biology, May 31, 2010, 120(2-3):86-95.
EP Extended Search Report in European Appln. No. 19802710.4, dated Jan. 19, 2022, 8 pages.
Aldevron.com [online], "Aldevron Announces Availability of GMP SpCas9," dated Nov. 15, 2017, retrieved on May 28, 2021, retrieved from URL<https://www.aldevron.com/about-us/news/aldevron-announces-availability-of-gmp-spcas92>, 4 pages.
Ali et al., "Adeno-Associated Virus Gene Transfer to Mouse Retina," Hum. Gene Therapy, Jan. 1, 1998, 9(1):81-86.

(Continued)

*Primary Examiner* — Richard A Schnizer
(74) *Attorney, Agent, or Firm* — Fish & Richardson P.C.

(57) ABSTRACT

The present disclosure provides modified cells including pluripotent stem cells, hematopoietic precursor cells, and hematopoietic cells (e.g., modified Tregs) that are steroid and/or calcineurin inhibitor-resistant. The present disclosure provides methods for generating steroid and/or calcineurin inhibitor-resistant modified cells including pluripotent stem cells, hematopoietic precursor cells, and hematopoietic cells. Also provided herein are compositions and methods of treatment.

13 Claims, 41 Drawing Sheets

Specification includes a Sequence Listing.

(56) References Cited

U.S. PATENT DOCUMENTS

| | | | |
|---|---|---|---|
| 6,534,055 | B1 | 3/2003 | June et al. |
| 6,567,694 | B2 | 5/2003 | Hayakawa |
| 6,678,556 | B1 | 1/2004 | Nolan et al. |
| 6,692,964 | B1 | 2/2004 | June et al. |
| 6,746,670 | B2 | 6/2004 | Levings et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,171,264 | B1 | 1/2007 | Hofmann et al. |
| 7,172,869 | B2 | 2/2007 | June et al. |
| 7,173,116 | B2 | 2/2007 | Fewell et al. |
| 7,175,843 | B2 | 2/2007 | June et al. |
| 7,232,566 | B2 | 6/2007 | June et al. |
| 7,651,855 | B2 | 1/2010 | Blazar et al. |
| 7,754,482 | B2 | 7/2010 | Riley et al. |
| 8,093,049 | B2 | 1/2012 | Tseng et al. |
| 8,129,185 | B2 | 3/2012 | Blazar et al. |
| 8,722,400 | B2 | 5/2014 | Riley et al. |
| 9,068,179 | B1 | 6/2015 | Liu et al. |
| 9,181,526 | B2 | 11/2015 | Blazar et al. |
| 9,187,727 | B2 | 11/2015 | Godfrey et al. |
| 9,228,172 | B2 | 1/2016 | Riley et al. |
| 9,273,282 | B2 | 3/2016 | Godfrey et al. |
| 9,555,105 | B2 | 1/2017 | Riley et al. |
| 9,574,179 | B2 | 2/2017 | Yu et al. |
| 9,644,179 | B2 | 5/2017 | Riley et al. |
| 9,840,699 | B2 | 12/2017 | Liu et al. |
| 2003/0170238 | A1 | 9/2003 | Gruenberg et al. |
| 2004/0014645 | A1 | 1/2004 | Draghia-Akli et al. |
| 2004/0059285 | A1 | 3/2004 | Mathiesen et al. |
| 2004/0092907 | A1 | 5/2004 | Mathiesen et al. |
| 2004/0131637 | A1 | 7/2004 | Chatfield |
| 2005/0052630 | A1 | 3/2005 | Smith et al. |
| 2005/0070841 | A1 | 3/2005 | Mathiesen et al. |
| 2006/0121005 | A1 | 6/2006 | Berenson et al. |
| 2007/0128708 | A1 | 6/2007 | Gamelin |
| 2011/0059502 | A1 | 3/2011 | Chalasani |
| 2013/0101567 | A1 | 4/2013 | Riley et al. |
| 2014/0068797 | A1 | 3/2014 | Doudna et al. |
| 2015/0166980 | A1 | 6/2015 | Liu et al. |
| 2015/0166984 | A1 | 6/2015 | Liu et al. |
| 2015/0166985 | A1 | 6/2015 | Liu et al. |
| 2016/0151471 | A1 | 6/2016 | Riley et al. |
| 2016/0272999 | A1 | 9/2016 | Duchateau et al. |
| 2016/0304846 | A1 | 10/2016 | Liu et al. |
| 2017/0121693 | A1 | 5/2017 | Liu et al. |
| 2017/0211042 | A1 | 7/2017 | Riley et al. |
| 2018/0073012 | A1 | 3/2018 | Liu et al. |
| 2018/0362975 | A1* | 12/2018 | Chen .................... C12N 15/09 |

FOREIGN PATENT DOCUMENTS

| | | |
|---|---|---|
| WO | WO 1993019191 | 9/1993 |
| WO | WO 1994012649 | 6/1994 |
| WO | WO 1994028938 | 12/1994 |
| WO | WO 1995000655 | 1/1995 |
| WO | WO 1995011984 | 5/1995 |
| WO | WO 1996017951 | 6/1996 |
| WO | WO 2001029058 | 4/2001 |
| WO | WO 2001096584 | 12/2001 |
| WO | WO 2002092793 | 11/2002 |
| WO | WO 2003054189 | 7/2003 |
| WO | WO 2003054201 | 7/2003 |
| WO | WO 2003099215 | 12/2003 |
| WO | WO 2006108882 | 10/2006 |
| WO | WO 2007010406 | 1/2007 |
| WO | WO 2014191128 | 12/2014 |
| WO | WO 2015089406 | 6/2015 |
| WO | WO 2017093969 | 6/2017 |

OTHER PUBLICATIONS

Ali et al., "Gene transfer into the mouse retina mediated by an adeno-associated viral vector," Hum. Mol. Genetics, May 5, 1996, 5(5):591-594.

Alpuche-Aranda et al., "*Salmonella typhimurium* activates virulence gene transcription within acidified macrophage phagosomes," Proc. Natl. Acad. Sci. USA, Nov. 1992, 89(21):10079-10083.

Anderson, "Human Gene Therapy," Science, May 8, 1992, 256(5058):808-813.

Bennett et al., "Real-Time, Noninvasive In Vivo Assessment of Adeno-Associated Virus-Mediated Retinal Transduction," Invest. Opthalmol. Vis. Science, Dec. 1997, 38(13):2857-2863.

Borrás et al., "Adenoviral reporter gene transfer to the human trabecular meshwork does not alter aqueous humor outflow. Relevance for potential gene therapy of glaucoma," Gene Therapy, Apr. 1999, 6(4):515-524.

Brewin et al., "Generation of EBV-specific cytotoxic T cells that are resistant to calcineurin inhibitors for the treatment of posttransplantation lymphoproliferative disease," Blood, Nov. 26, 2009, 114(23):4792-4803.

Briner et al., "Guide RNA Functional Modules Direct Cas9 Activity and Orthogonality," Mol. Cell, Oct. 23, 2014, 56(2):333-339.

Chatfield et al., "Use of the nirB promoter to direct the stable expression of heterologous antigens in *Salmonella* oral vaccine strains: development of a single-dose oral tetanus vaccine," Nat. Biotechnology, Aug. 1, 1992, 10(8):888-892.

Chen et al., "Enhanced proofreading governs CRISPR-Cas9 targeting accuracy," Nature, Oct. 19, 2017, 550(7676):407-410.

Cougot et al., "'Cap-tabolism'," Trends in Biochem. Science, Aug. 2004, 29(8):436-444.

Danthinne et al., "Production of first generation adenovirus vectors: a review," Gene Therapy, Oct. 25, 2000, 7(20):1707-1714.

Davidson et al., "Cutting Edge: IL-2 Is Essential for TGF-β-Mediated Induction of Foxp3 T Regulatory Cells," J. Immunology, Apr. 1, 2007, 178(7):4022-4026.

Davila et al., "CD19 CAR-Targeted T Cells Induce Long-Term Remission and B Cell Aplasia in an Immunocompetent Mouse Model of B Cell Acute Lymphoblastic Leukemia," PLoS One, Apr. 9, 2013, 8(4):e61338, 14 pages.

De Boer et al., "The tac promoter: a functional hybrid derived from the trp and lac promoters," Proc. Natl. Acad. Sci. USA, Jan. 1, 1983, 80(1):21-25.

Dunstan et al., "Use of In Vivo-Regulated Promoters To Deliver Antigens from Attenuated *Salmonella enterica* var. *typhimurium*," Infect. Immunity, Oct. 1999, 67(10):5133-5141.

Eckelhart et al., "A novel Ncr1-Cre mouse reveals the essential role of STAT5 for NK-cell survival and development," Blood, Feb. 3, 2011, 117(5):1565-1573.

Elango et al., "Optimized transfection of mRNA transcribed from a d(A/T)100 tail-containing vector," Biochem. Biophys. Res. Communications, May 13, 2005, 330(3):958-966.

Flannery et al., "Efficient photoreceptor-targeted gene expression in vivo by recombinant adeno-associated virus," Proc. Natl. Acad. Sci. USA, Jun. 24, 1997, 94(13):6916-6921.

Flotte et al., "Stable in vivo expression of the cystic fibrosis transmembrane conductance regulator with an adeno-associated virus vector," Proc. Natl. Acad. Sci. USA, Nov. 15, 1993, 90(22):10613-10617.

Fuhrmann-Benzakein et al., "Inducible and irreversible control of gene expression using a single transgene," Nucleic Acids Research, Dec. 1, 2000, 28(23):E99.

Gaudelli et al., "Programmable base editing of A•T to G•C in genomic DNA without DNA cleavage," Nature, Nov. 1, 2017, 551(7681):464-471.

GenBank Accession No. ACX34095.1, "calcineurin B [synthetic construct]," dated Jan. 21, 2010, 1 page.

GenBank Accession No. AX798183.1, "Sequence 59 from Patent WO03054201," dated Oct. 8, 2003, 1 page.

GenBank Accession No. AX798961.1, "Sequence 53 from Patent WO03054189," dated Oct. 8, 2003, 1 page.

(56) References Cited

OTHER PUBLICATIONS

GenBank Accession No. AX798980.1, "Sequence 72 from Patent WO03054189," dated Oct. 8, 2003, 1 page.
GenBank Accession No. GQ463594.1, "Synthetic construct clone CNa12 calcineurin A gene, complete cds," dated Jan. 21, 2010, 2 pages.
GenBank Accession No. GQ463595.1, "Synthetic construct clone CNa22 calcineurin A gene, complete cds," dated Jan. 21, 2010, 2 pages.
GenBank Accession No. GQ463597.1, "Synthetic construct clone CNb30 calcineurin B gene, complete cds," dated Jan. 21, 2010, 1 page.
GenBank Accession No. NG_009014.2, "*Homo sapiens* androgen receptor (AR), RefSeqGene on chromosome X," dated Mar. 16, 2017, 46 pages.
GenBank Accession No. NG_009062.1, "*Homo sapiens* nuclear receptor subfamily 3 group C member 1 (NR3C1), RefSeqGene on chromosome 5," dated Apr. 10, 2017, 38 pages.
GenBank Accession No. NG_013350.1, "*Homo sapiens* nuclear receptor subfamily 3 group C member 2 (NR3C2), RefSeqGene on chromosome 4," dated Apr. 10, 2017, 80 pages.
GenBank Accession No. NG_016475.1, "*Homo sapiens* progesterone receptor (PGR), RefSeqGene on chromosome 11," dated Mar. 31, 2017, 26 pages.
GenBank Accession No. NM_001018074.1, "*Homo sapiens* nuclear receptor subfamily 3 group C member 1 (NR3C1), transcript variant 2, mRNA," dated Apr. 30, 2017, 7 pages.
Grindley et al., "Mechanisms of Site-Specific Recombination," Ann. Rev. Biochem., Jul. 7, 2006, 75:567-605.
Groux et al., "A CD4+T-cell subset inhibits antigen-specific T-cell responses and prevents colitis," Nature, Oct. 16, 1997, 389(6652):737-742.
Harborne et al., "Transcriptional control, translation and function of the products of the five open reading frames of the *Escherichia coli* nir operon," Mol. Microbiology, Oct. 1992, 6(19):2805-2813.
Herman et al., "The VITAL assay: a versatile fluorometric technique for assessing CTL- and NKT-mediated cytotoxicity against multiple targets in vitro and in vivo," J. Immunol. Methods, Feb. 1, 2004, 285(1):25-40.
Hillen et al., "Tet repressor-tel operator interaction," in Topics in Molecular and Structural Biology: Protein-Nucleic Acid Interaction, 1989, 10:143-162.
Hippen et al., "Generation and Large-Scale Expansion of Human Inducible Regulatory T Cells That Suppress Graft-Versus-Host Disease," Am. J. Transplantation, Jun. 2011, 11(6):1148-1157.
Hippen et al., "Umbilical cord blood regulatory T-cell expansion and functional effects of tumor necrosis factor receptor family members OX40 and 4-1BB expressed on artificial antigen-presenting cells," Blood, Oct. 1, 2008, 112(7):2847-2857.
Hu et al., "Evolved Cas9 variants with broad PAM compatibility and high DNA specificity," Nature, Feb. 28, 2018, 556(7699):57-63.
Jasin et al., "Repair of Strand Breaks by Homologous Recombination," Cold Spring Harb. Perspect. Biology, Oct. 4, 2013, 5(11):a012740, 19 pages.
Jiang et al., "RNA-guided editing of bacterial genomes using CRISPR-Cas systems," Nat. Biotechnology, Jan. 29, 2013, 31(3):233-239.
Jinek et al., "A Programmable Dual-RNA-Guided DNA Endonuclease in Adaptive Bacterial Immunity," Science, Aug. 17, 2012, 337(6096):816-821.
Jomary et al., "Rescue of photoreceptor function by AAV-mediated gene transfer in a mouse model of inherited retinal degeneration," Gene Therapy, Jul. 1997, 4(7):683-690.
Kleinstiver et al., "High-fidelity CRISPR-Cas9 nucleases with no detectable genome-wide off-target effects," Nature, Jan. 6, 2016, 529(7587):490-495.
Kluesner et al., "EditR: A novel base editing quantification software using Sanger sequencing," bioRxiv, Nov. 5, 2017, 19 pages.

Kochenderfer et al., "Construction and Preclinical Evaluation of an Anti-CD19 Chimeric Antigen Receptor," J. Immunotherapy, Sep. 2009, 32(7):689-702.
Li et al., "In vivo transfer of a reporter gene to the retina mediated by an adenoviral vector," Invest. Opthalmol. Vis. Science, Apr. 1994, 35(5):2543-2549.
Li et al., "Phenotype correction in retinal pigment epithelium in murine mucopolysaccharidosis VII by adenovirus-mediated gene transfer," Proc. Natl. Acad. Sci. USA, Aug. 15, 1995, 92(17):7700-7704.
Mali et al., "RNA-guided human genome engineering via Cas9," Science, Feb. 15, 2013, 339(6121):823-826.
Marodon et al., "Specific transgene expression in human and mouse CD4 cells using lentiviral vectors with regulatory sequences from the CD4 gene," Blood, May 1, 2003, 101(9):3416-3423.
McKelvie et al., "Expression of heterologous antigens in *Salmonella typhimurium* vaccine vectors using the in vivo-inducible, SPI-2 promoter, ssaG," Vaccine, Sep. 3, 2004, 22(25-26):3243-3255.
Melton et al., "Efficient in vitro synthesis of biologically active RNA and RNA hybridization probes from plasmids containing a bacteriophage SP6 promoter," Nucleic Acids Research, Sep. 25, 1984, 12(18):7035-7056.
Mendelson et al., "Expression and rescue of a nonselected marker from an integrated AAV vector," Virology, Sep. 1988, 166(1):154-165.
Menger et al., "TALEN-mediated genetic inactivation of the glucocorticoid receptor in cytomegalovirus-specific T cells," Blood, Dec. 24, 2015, 126(26):2781-2789.
Miyoshi et al., "Stable and efficient gene transfer into the retina using an HIV-based lentiviral vector," Proc. Natl. Acad. Sci. USA, Sep. 16, 1997, 94(19):10319-10323.
Mumtaz et al., "Design of liposomes for circumventing the reticuloendothelial cells," Glycobiology, Nov. 5, 1991, 1(5):505-510.
Nacheva et al., "Preventing nondesired RNA-primed RNA extension catalyzed by T7 RNA polymerase," Eur. J. Biochemistry, Apr. 2003, 270(7):1485-1465.
OSU.edu [online], "NCH GMP + Viral Vector Cores," available on or before Jan. 20, 2018 via Internet Archive: Wayback Machine URL<https://web.archive.org/web/20180120022629/https://ccts.osu.edu/content/nch-gmp-viral-vector>, retrieved on May 28, 2021, retrieved from URL<https://ccts.osu.edu/content/nch-gmp-viral-vector>, 2 pages.
Pandolfi et al., "Regulatory and effector T-cells are differentially modulated by Dexamethasone," Clin. Immunology, Dec. 2013, 149(3):400-410.
PCT International Preliminary Report on Patentability in International Appln. No. PCT/US2019/032686, dated Nov. 17, 2020, 15 pages.
PCT International Search Report and Written Opinion in International Appln. No. PCT/US2019/032686, dated Aug. 20, 2019, 18 pages.
Porter et al., "Suppressor Function of Umbilical Cord Blood-Derived CD4+ CD25+ T-Regulatory Cells Exposed to Graft-versus-Host Disease Drugs," Transplantation, Jul. 15, 2006, 82(1):23-29.
Pulkkinen et al., "A *Salmonella typhimurium* virulence protein is similar to a Yersinia enterocolitica invasion protein and a bacteriophage lambda outer membrane protein," J. Bacteriology, Jan. 1991, 173(1):86-93.
Qi et al., "Repurposing CRISPR as an RNA-Guided Platform for Sequence-Specific Control of Gene Expression" Cell, Feb. 28, 2013, 152(5):1173-1183.
Rolling et al., "Evaluation of Adeno-Associated Virus-Mediated Gene Transfer into the Rat Retina by Clinical Fluorescence Photography," Hum. Gene Therapy, Mar. 1, 1999, 10(4):641-648.
Rosenberg, "Cell transfer immunotherapy for metastatic solid cancer—what clinicians need to know," Nat. Rev. Clin. Oncology, Aug. 2, 2011, 8(10):577-585.
Sakamoto et al., "A vitrectomy improves the transfection efficiency of adenoviral vector-mediated gene transfer to Müller cells," Gene Therapy, Aug. 17, 1998, 5(8):1088-1097.

(56) References Cited

OTHER PUBLICATIONS

Salmon et al., "Characterization of the human CD4 gene promoter: transcription from the CD4 gene core promoter is tissue-specific and is activated by Ets proteins," Proc. Natl. Acad. Sci. USA, Aug. 15, 1993, 90(16):7739-7743.
Samulski et al., "Helper-free stocks of recombinant adeno-associated viruses: normal integration does not require viral gene expression," J. Virology, Sep. 1989, 63(9):3822-3828.
Sather et al., "Efficient modification of CCR5 in primary human hematopoietic cells using a megaTAL nuclease and AAV donor template," Sci. Transl. Medicine, Sep. 30, 2015, 7(307):307ra156, 15 pages.
Schenborn et al., "A novel transcription property of SP6 and T7 RNA polymerases: dependence on template structure," Nucleic Acids Research, Sep. 11, 1985, 13(17):6223-6236.
Shetron-Rama et al., "Intracellular induction of Listeria monocytogenes actA expression," Infect. Immunity, Mar. 2002, 70(3):1087-1096.
Slaymaker et al., "Rationally engineered Cas9 nucleases with improved specificity," Science, Jan. 1, 2016, 351(6268):84-88.
Stepinski et al., "Synthesis and properties of mRNAs containing the novel "anti-reverse" cap analogs 7-methyl(39-O-methyl)GppppG and 7-methyl(39-deoxy)GppppG," RNA, Oct. 2001, 7(10):1468-1495.
Takahashi et al., "Rescue from Photoreceptor Degeneration in the rd Mouse by Human Immunodeficiency Virus Vector-Mediated Gene Transfer," J. Virology, Sep. 1999, 73(9):7812-7816.
Themeli et al., "Generation of tumor-targeted human T lymphocytes from induced pluripotent stem cells for cancer therapy," Nat. Biotechnology, Aug. 11, 2013, 31(10):928-933.
Thomson et al., "Embryonic Stem Cell Lines Derived from Human Blastocysts," Science, Nov. 6, 1998, 282(5391):1145-1147.
Tsukahara et al., "CD19 target-engineered T-cells accumulate at tumor lesions in human B-cell lymphoma xenograft mouse models," Biochem. Biophys. Res. Communications, Aug. 16, 2013, 438(1):84-89.
Ui-Tei et al., "Sensitive assay of RNA interference in *Drosophila* and Chinese hamster cultured cells using firefly luciferase gene as target," FEBS Letters, Aug. 18, 2000, 479(3):79-82.
Valdivia et al., "Bacterial genetics by flow cytometry: rapid isolation of *Salmonella typhimurium* acid-inducible promoters by differential fluorescence induction," Mol. Microbiology, Oct. 1996, 22(2):367-378.
Wakkach et al., "Characterization of Dendritic Cells that Induce Tolerance and T Regulatory 1 Cell Differentiation In Vivo," Immunity, May 2003, 18(5):605-617.
Wu et al., "MicroRNA-30 family members regulate calcium/calcineurin signaling in podocytes," J. Clin. Investigation, Oct. 5, 2015, 125(11):4091-4106.
Yu et al., "Induced Pluripotent Stem Cell Lines Derived from Human Somatic Cells," Science, Dec. 21, 2007, 318(5858):1917-1920.
Yu et al., "Progress towards gene therapy for HIV infection," Gene Therapy, Jan. 1994, 1:13-26.
Zeiser et al., "Differential impact of mammalian target of rapamycin inhibition on CD4+CD25+Foxp3+ regulatory T cells compared with conventional CD4+ T cells," Blood, Jan. 1, 2008, 111(1):453-462.
Zeiser et al., Inhibition of CD4+CD25+ regulatory T-cell function by calcineurin-dependent interleukin-2 production, Blood, Jul. 1, 2006, 108(1):390-399.
Zhao et al., "Multiple Injections of Electroporated Autologous T Cells Expressing a Chimeric Antigen Receptor Mediate Regression of Human Disseminated Tumor," Cancer Research, Nov. 15, 2010, 70(22):9053-9061.

\* cited by examiner

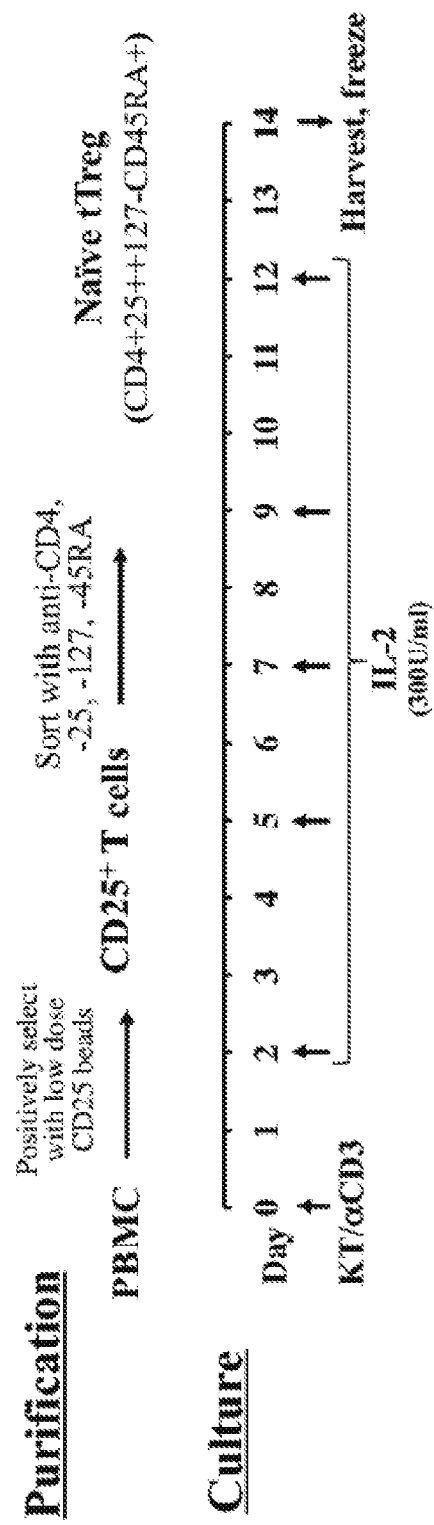

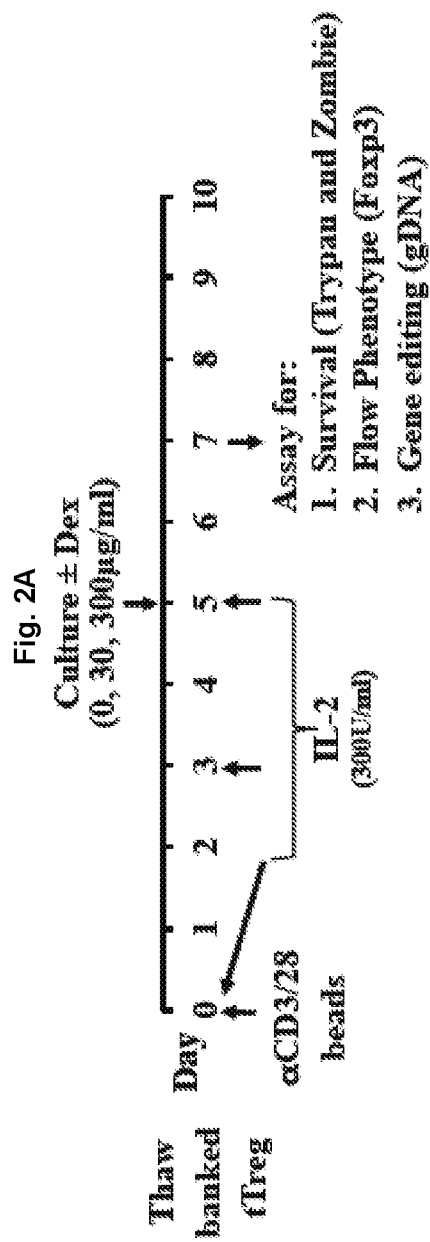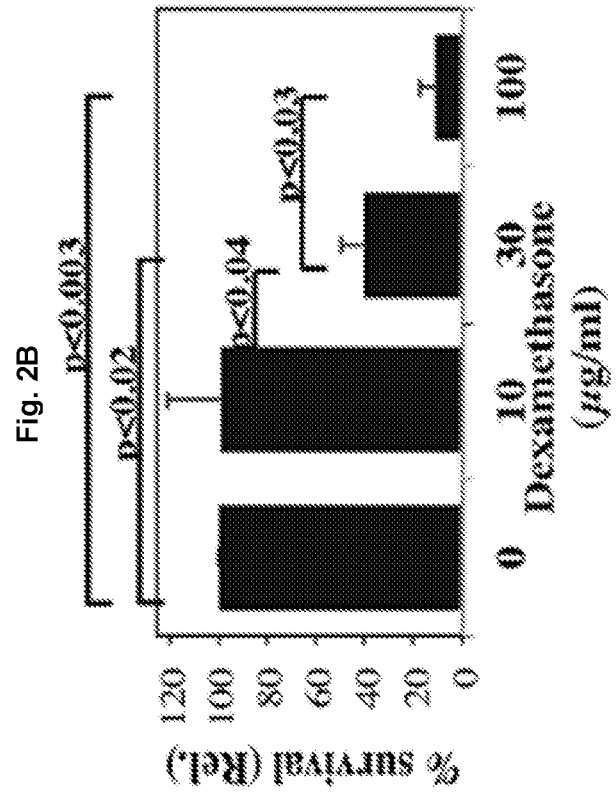
Fig. 2A
Fig. 2B

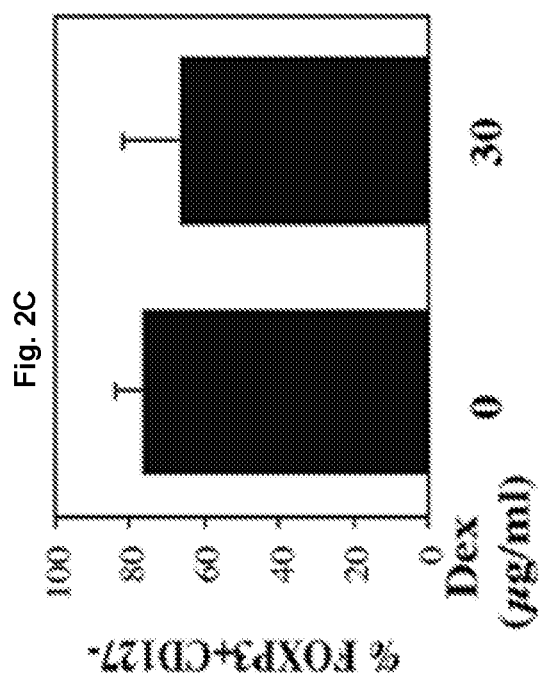
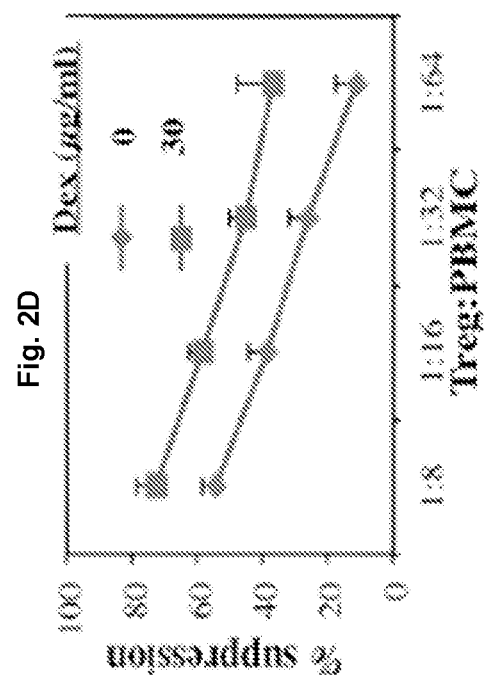

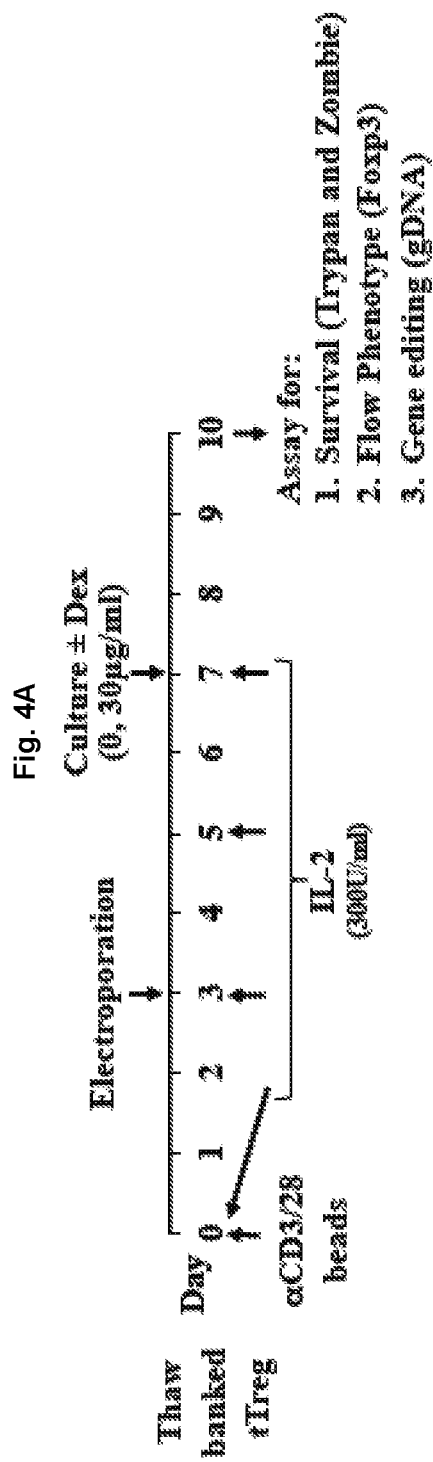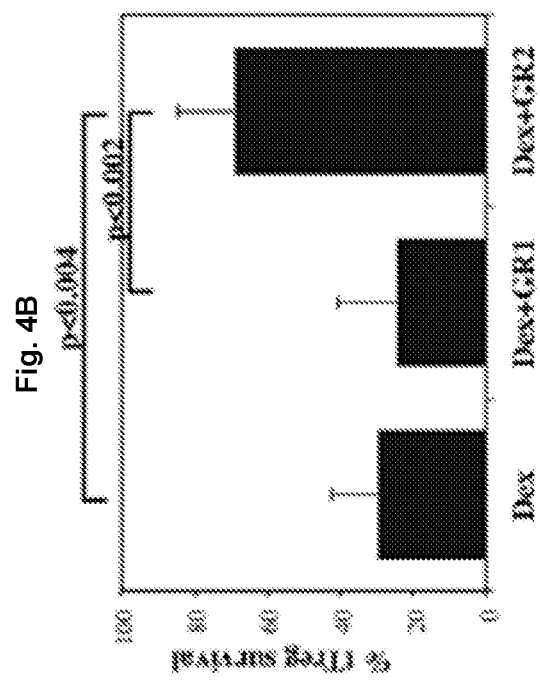

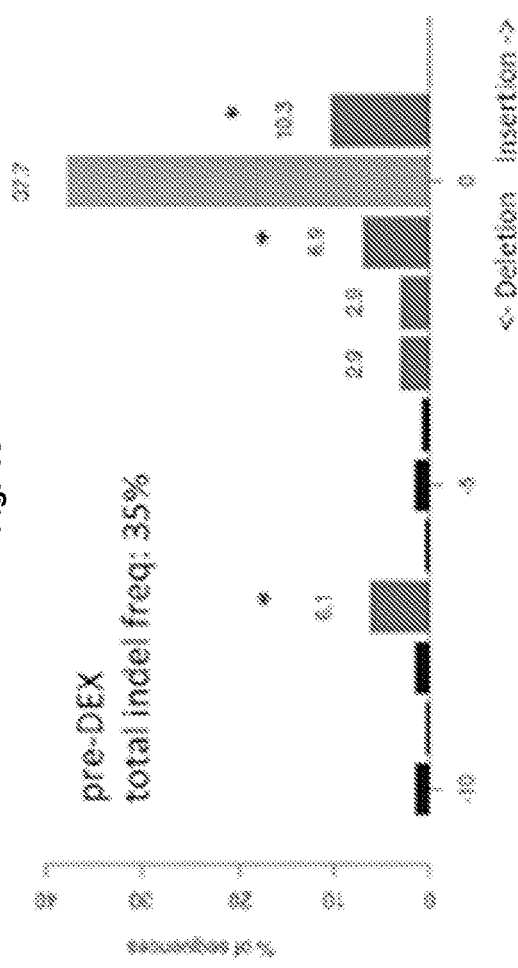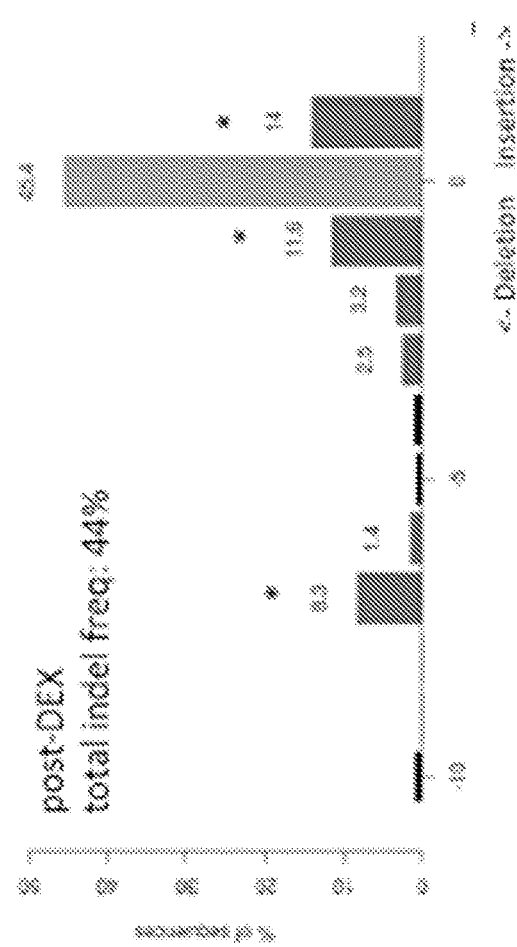

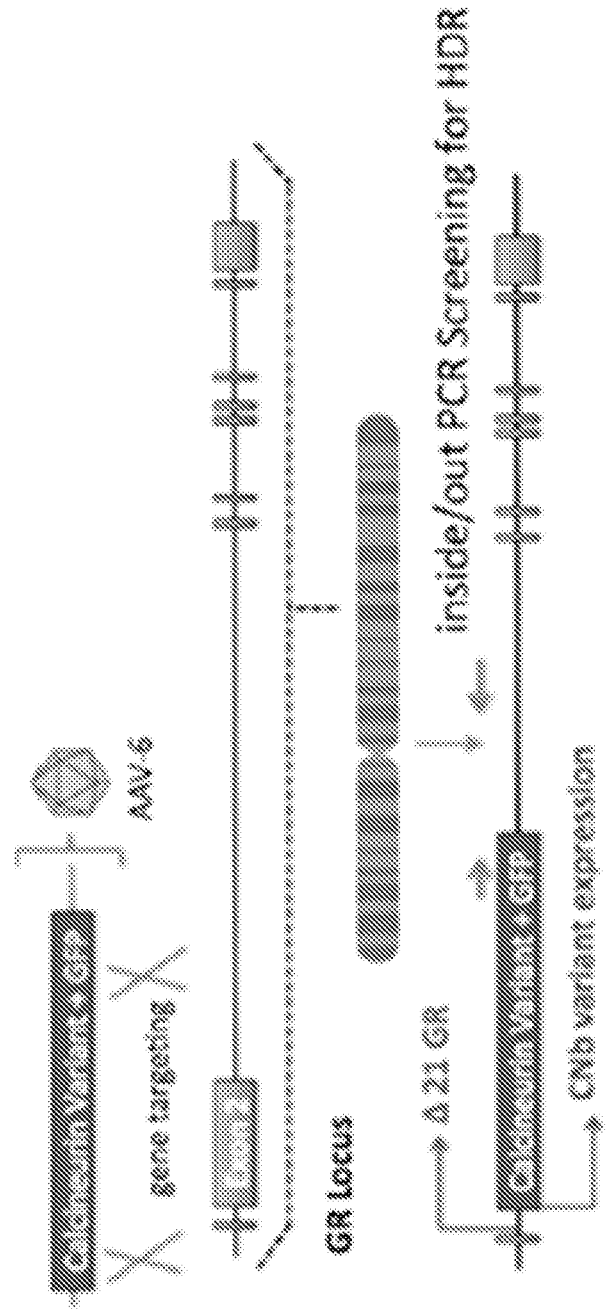
Fig. 5A
Fig. 5B

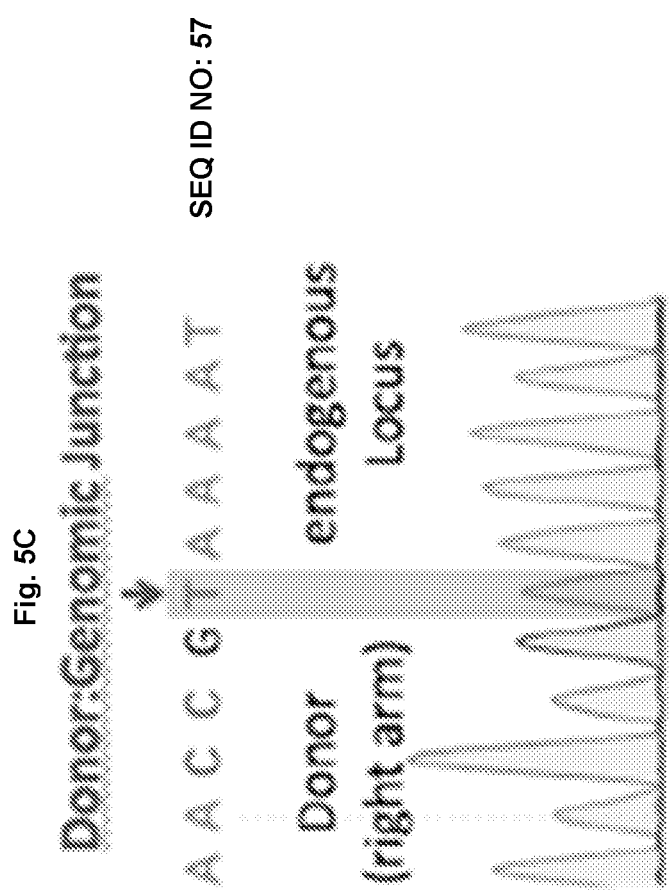

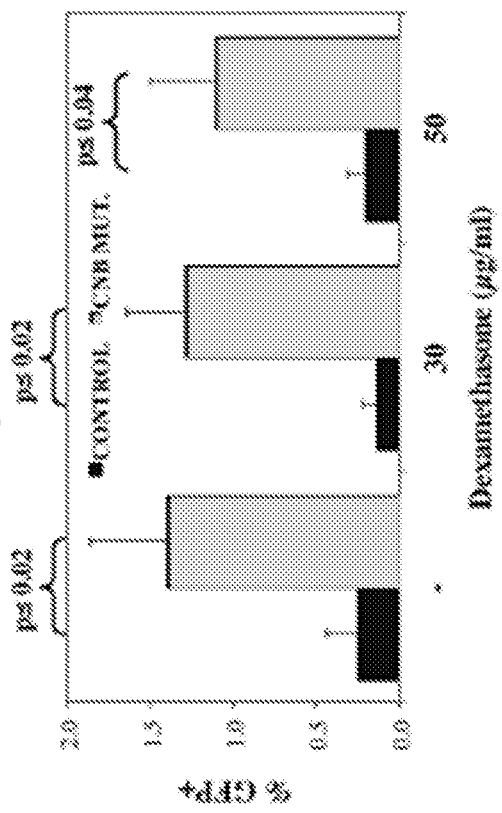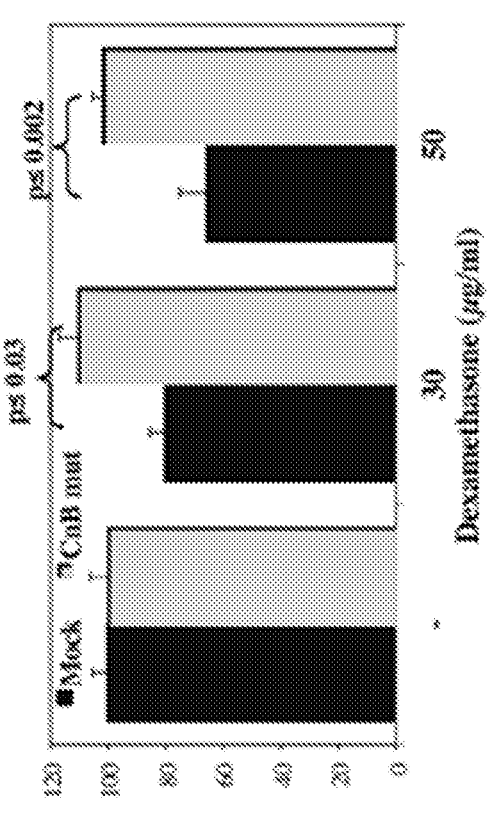

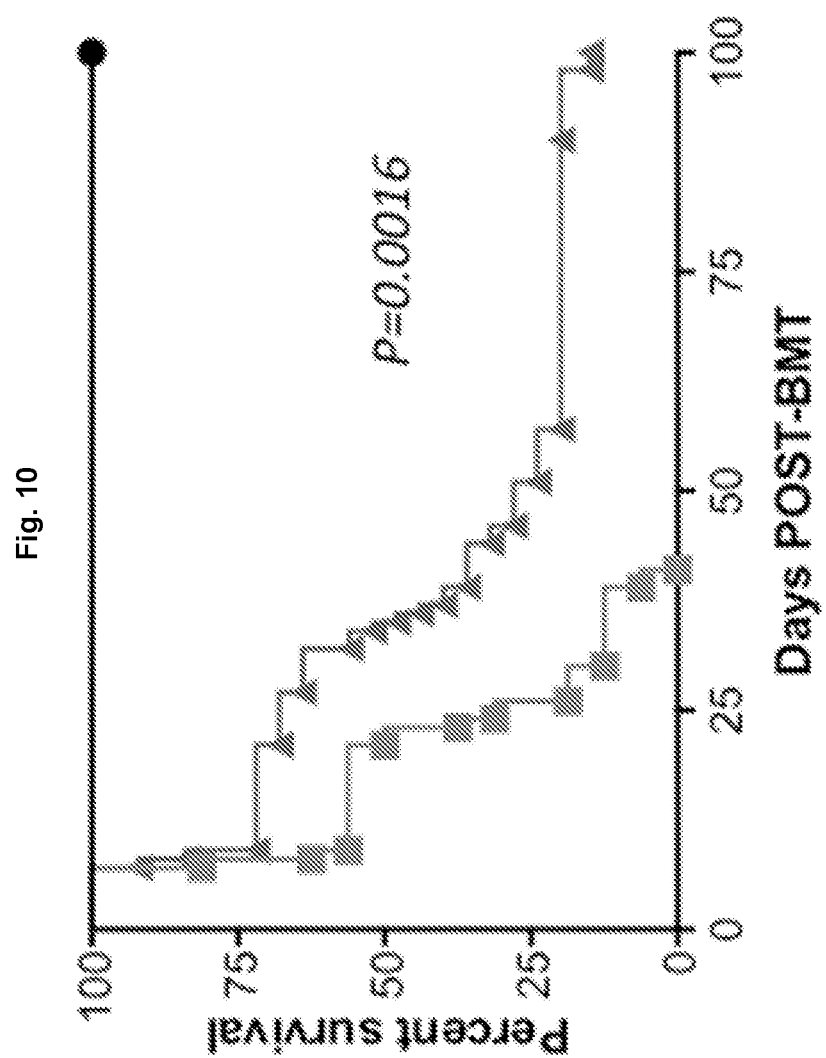

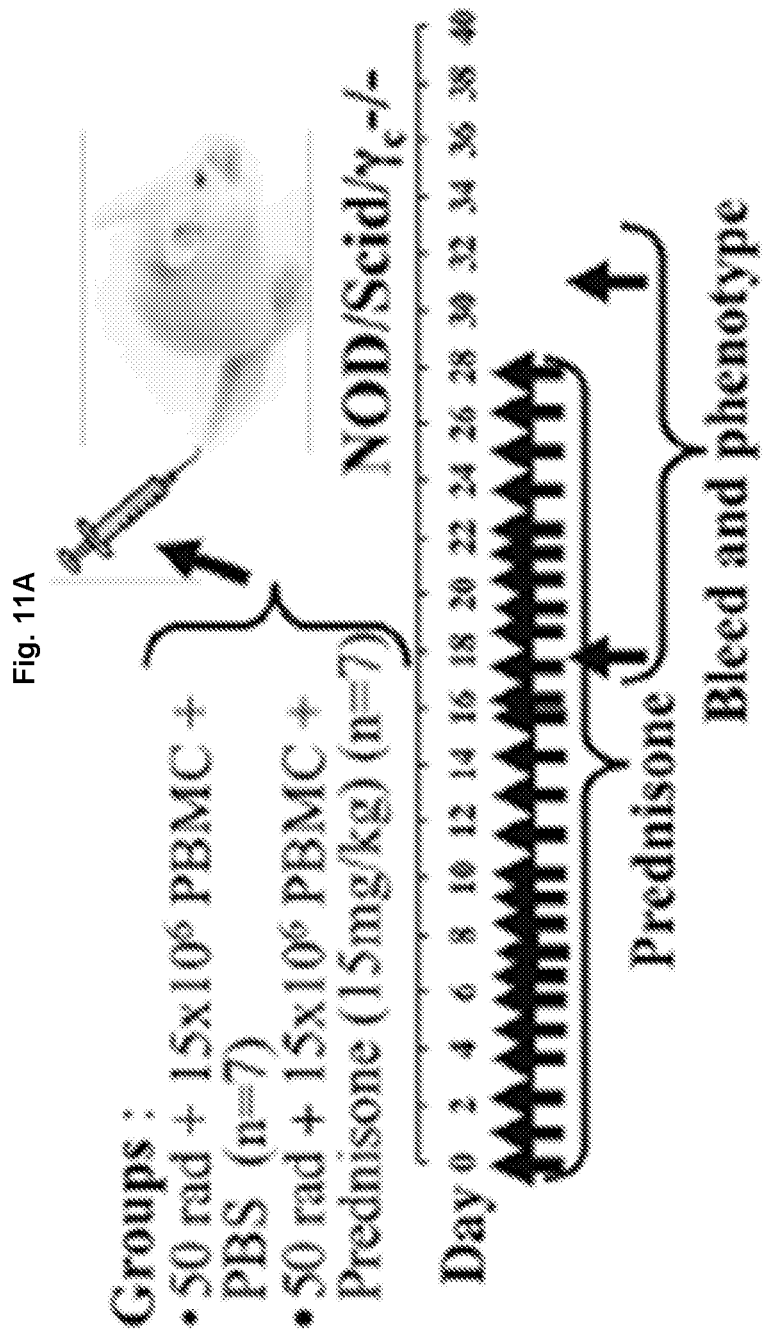

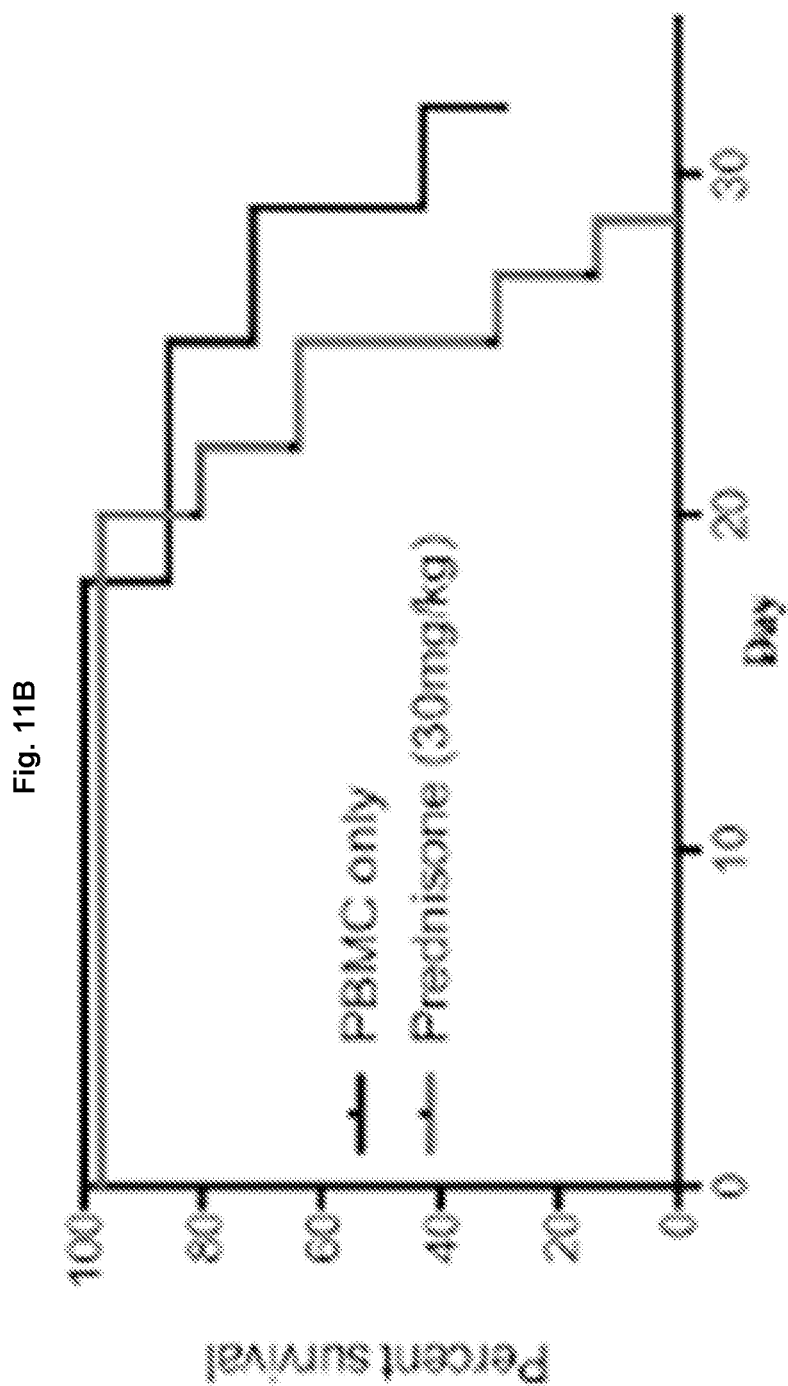

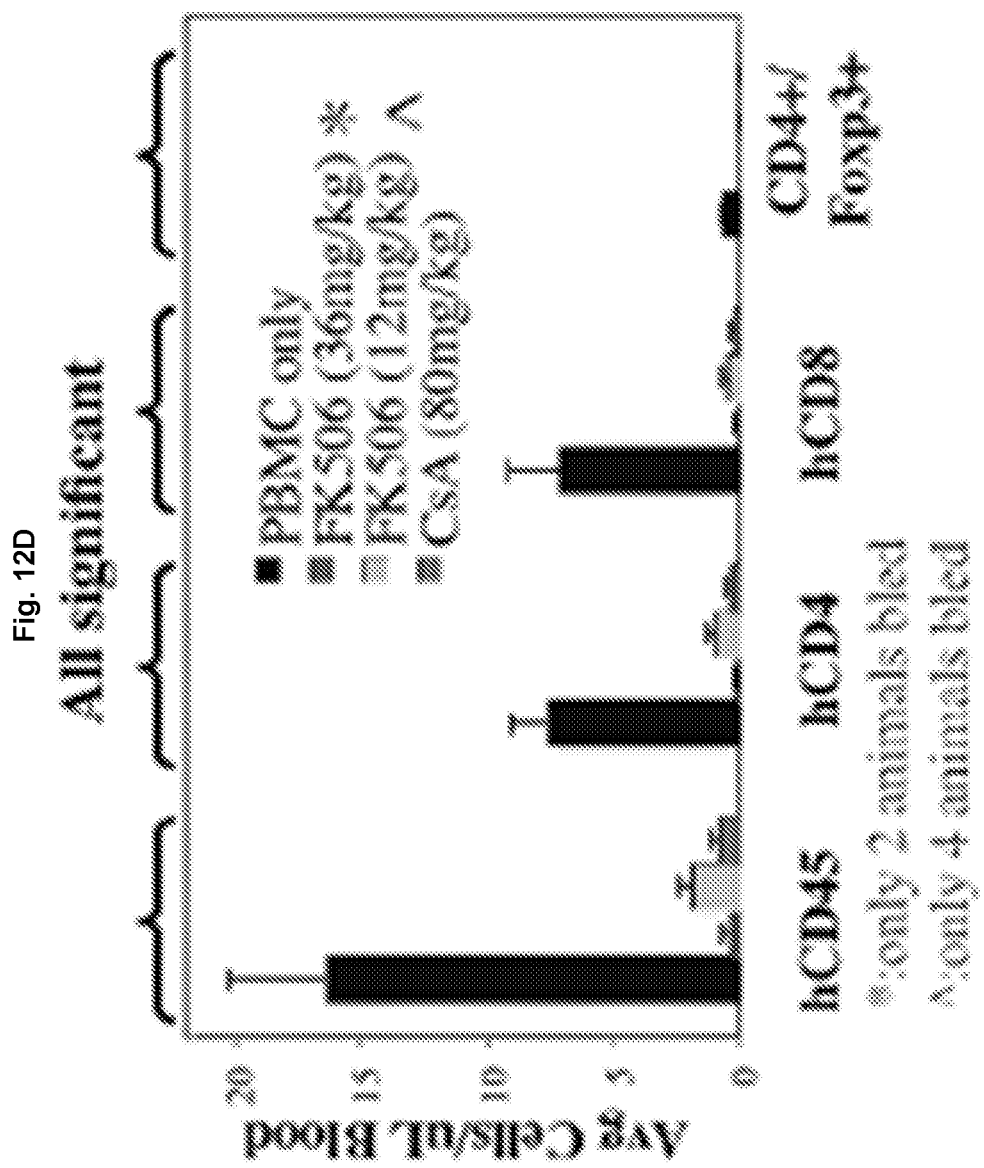

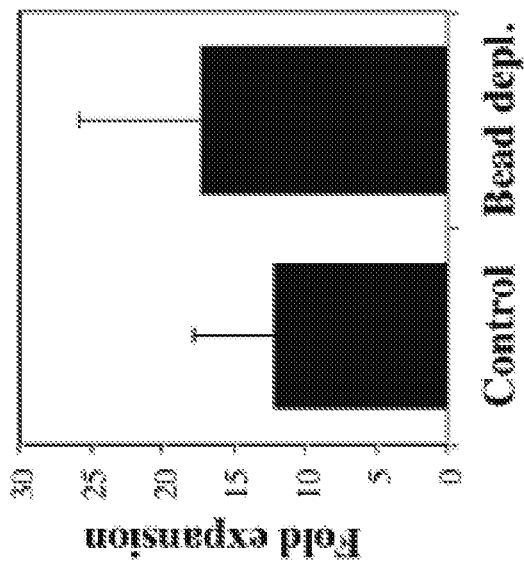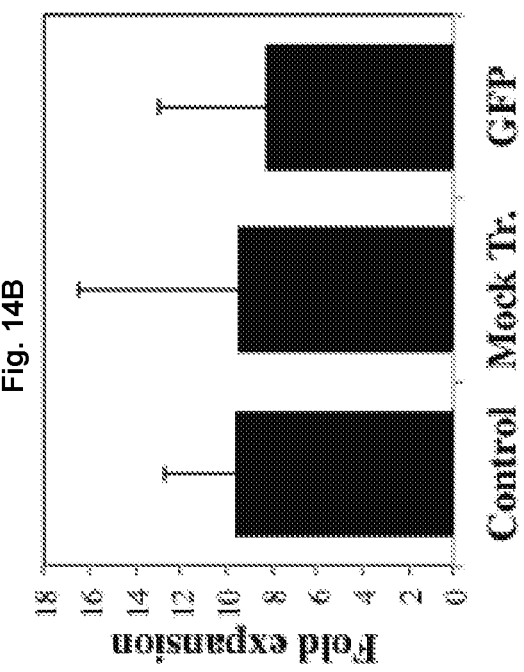

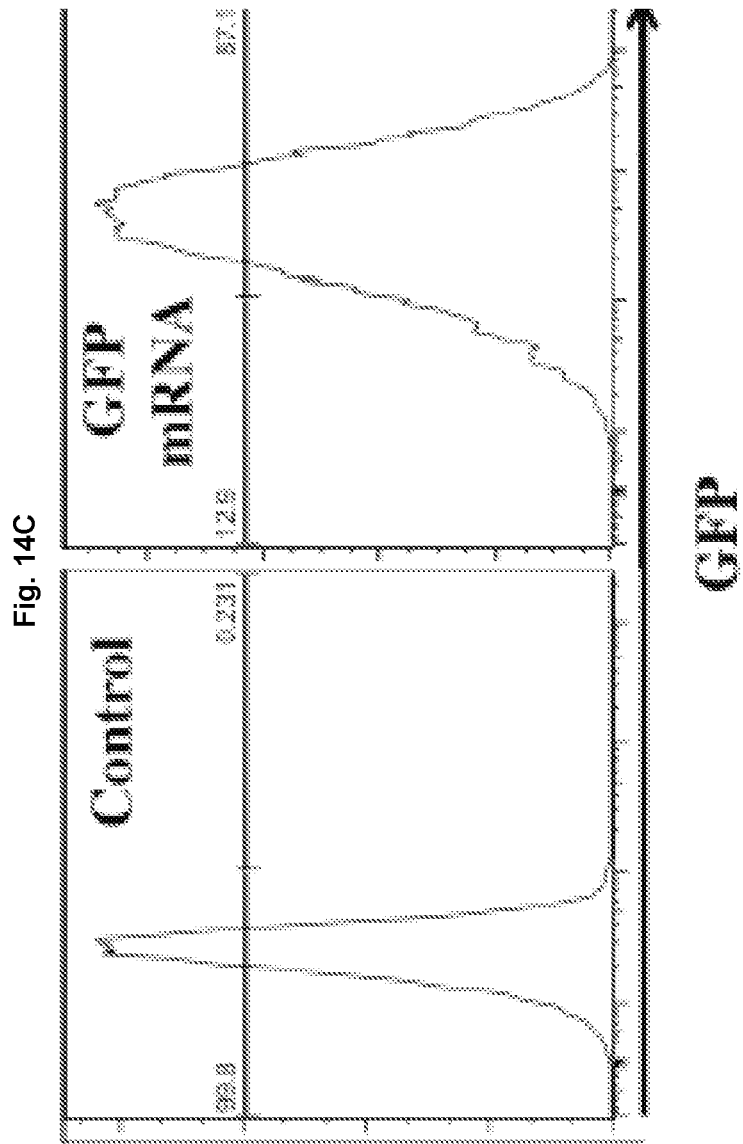

SEQUENCE LISTING

```
<160> NUMBER OF SEQ ID NOS: 67

<210> SEQ ID NO 1
<211> LENGTH: 521
<212> TYPE: PRT
<213> ORGANISM: Artificial Sequence
<220> FEATURE:
<223> OTHER INFORMATION: synthetic

<400> SEQUENCE: 1

Met Ser Glu Pro Lys Ala Ile Asp Pro Lys Leu Ser Thr Thr Asp Arg
1               5                   10                  15

Val Val Lys Ala Val Pro Phe Pro Pro Ser His Arg Leu Thr Ala Lys
            20                  25                  30

Glu Val Phe Asp Asn Asp Gly Lys Pro Arg Val Asp Ile Leu Lys Ala
        35                  40                  45

His Leu Met Lys Glu Gly Arg Leu Glu Glu Ser Val Ala Leu Arg Ile
    50                  55                  60

Ile Thr Glu Gly Ala Ser Ile Leu Arg Gln Glu Lys Asn Leu Leu Asp
65                  70                  75                  80

Ile Asp Ala Pro Val Thr Val Cys Gly Asp Ile His Gly Gln Phe Phe
                85                  90                  95
```

```
Asp Leu Met Lys Leu Phe Glu Val Gly Gly Ser Pro Ala Asn Thr Arg
            100                 105                 110

Tyr Leu Phe Leu Gly Asp Tyr Val Asp Arg Gly Tyr Phe Ser Ile Glu
            115                 120                 125

Cys Val Leu Tyr Leu Trp Ala Leu Lys Ile Leu Tyr Pro Lys Thr Leu
            130                 135                 140

Phe Leu Leu Arg Gly Asn His Glu Cys Arg His Leu Thr Glu Tyr Phe
145                 150                 155                 160

Thr Phe Lys Gln Glu Cys Lys Ile Lys Tyr Ser Glu Arg Val Tyr Asp
            165                 170                 175

Ala Cys Met Asp Ala Phe Asp Cys Leu Pro Leu Ala Ala Leu Met Asn
            180                 185                 190

Gln Gln Phe Leu Cys Val His Gly Gly Leu Ser Pro Glu Ile Asn Thr
            195                 200                 205

Leu Asp Asp Ile Arg Lys Leu Asp Arg Phe Lys Glu Pro Pro Ala Tyr
210                 215                 220

Gly Pro Met Cys Asp Ile Leu Trp Ser Asp Pro Leu Glu Asp Phe Gly
225                 230                 235                 240

Asn Glu Lys Thr Gln Glu His Phe Thr His Asn Thr Val Arg Gly Cys
            245                 250                 255

Ser Tyr Phe Tyr Ser Tyr Pro Ala Val Cys Glu Phe Leu Gln His Asn
            260                 265                 270

Asn Leu Leu Ser Ile Leu Arg Ala His Glu Ala Gln Asp Ala Gly Tyr
            275                 280                 285

Arg Met Tyr Arg Lys Ser Gln Thr Thr Gly Phe Pro Ser Leu Ile Thr
290                 295                 300

Ile Phe Ser Ala Pro Asn Tyr Leu Asp Val Tyr Asn Asn Lys Ala Ala
305                 310                 315                 320

Val Leu Lys Tyr Glu Asn Asn Val Met Asn Ile Arg Gln Phe Asn Cys
            325                 330                 335

Ser Pro His Pro Tyr Trp Leu Pro Asn Phe Met Asp Val Phe Thr Trp
            340                 345                 350

Ser Leu Pro Phe Val Gly Glu Lys Val Thr Glu Met Leu Val Asn Val
            355                 360                 365

Leu Asn Ile Cys Ser Asp Asp Glu Leu Gly Ser Glu Glu Asp Gly Phe
370                 375                 380

Asp Gly Ala Thr Ala Ala Ala Arg Lys Glu Val Ile Arg Asn Lys Ile
385                 390                 395                 400

Arg Ala Ile Gly Lys Met Ala Arg Val Phe Ser Val Leu Arg Glu Glu
            405                 410                 415

Ser Glu Ser Val Leu Thr Leu Lys Gly Leu Thr Pro Thr Gly Met Leu
            420                 425                 430

Pro Ser Gly Val Leu Ser Gly Gly Lys Gln Thr Leu Gln Ser Ala Thr
            435                 440                 445

Val Glu Ala Ile Glu Ala Asp Glu Ala Ile Lys Gly Phe Ser Pro Gln
            450                 455                 460

His Lys Ile Thr Ser Phe Glu Glu Ala Lys Gly Leu Asp Arg Ile Asn
465                 470                 475                 480

Glu Arg Met Pro Pro Arg Arg Asp Ala Met Pro Ser Asp Ala Asn Leu
            485                 490                 495

Asn Ser Ile Asn Lys Ala Leu Thr Ser Glu Thr Asn Gly Thr Asp Ser
            500                 505                 510
```

```
Asn Gly Ser Asn Ser Ser Asn Ile Gln
        515                 520
```

```
<210> SEQ ID NO 2
<211> LENGTH: 170
<212> TYPE: PRT
<213> ORGANISM: Artificial Sequence
<220> FEATURE:
<223> OTHER INFORMATION: synthetic

<400> SEQUENCE: 2
```

```
Met Gly Asn Glu Ala Ser Tyr Pro Leu Glu Met Cys Ser His Phe Asp
1               5                   10                  15

Ala Asp Glu Ile Lys Arg Leu Gly Lys Arg Phe Lys Lys Leu Asp Leu
            20                  25                  30

Asp Asn Ser Gly Ser Leu Ser Val Glu Glu Phe Met Ser Leu Pro Glu
        35                  40                  45

Leu Gln Gln Asn Pro Leu Val Gln Arg Val Ile Asp Ile Phe Asp Thr
    50                  55                  60

Asp Gly Asn Gly Glu Val Asp Phe Lys Glu Phe Ile Glu Gly Val Ser
65                  70                  75                  80

Gln Phe Ser Val Lys Gly Asp Lys Glu Gln Lys Leu Arg Phe Ala Phe
                85                  90                  95

Arg Ile Tyr Asp Met Asp Lys Asp Gly Tyr Ile Ser Asn Gly Glu Leu
            100                 105                 110

Phe Gln Val Leu Lys Met Met Val Gly Asn Asn Leu Lys Asp Thr Gln
        115                 120                 125

Leu Gln Gln Ile Val Asp Lys Thr Ile Ile Asn Ala Asp Lys Asp Gly
    130                 135                 140

Asp Gly Arg Ile Ser Phe Glu Glu Phe Cys Ala Val Val Gly Gly Leu
145                 150                 155                 160

Asp Ile His Lys Lys Met Val Val Asp Val
                165                 170
```

```
<210> SEQ ID NO 3
<211> LENGTH: 1566
<212> TYPE: DNA
<213> ORGANISM: Artificial Sequence
<220> FEATURE:
<223> OTHER INFORMATION: synthetic

<400> SEQUENCE: 3
```

```
atgagcgagc ccaaggccat cgaccccaag ctgtccacca ccgacagagt ggtgaaggcc      60 gtgcccttc  cccctccca  ccgcctgacc gccaaggagg tgttcgacaa cgatggcaag     120
cccagagtgg acatcctgaa agcccacctg atgaaggagg cagactgga  ggagagcgtg     180 gccctgcgca tcatcaccga gggcgccagc atcctgcgcc aggagaagaa cctgctggat     240
atcgacgccc ctgtgaccgt gtgcggcgac atccacggac agttttttcga cctgatgaag    300 ctgttcgagg tgggcggctc tcccgccaac accagatacc tgttcctggg cgactacgtg    360
gacagaggct acttctctat cgagtgcgtg ctgtacctgt gggccctgaa gatcctgtac    420
cccaagaccc tgttcctgct gagaggcaac cacgagtgcc gccacctgac cgagtacttt    480
accttcaagc aggagtgcaa gatcaagtac agcgagcgcg tgtacgatgc ctgcatggac    540
gccttcgact gtctgcccct ggccgctctg atgaaccagc agttcctgtg tgtgcacgga    600
ggcctgagcc ccgagatcaa cacccctgga cgacatccgga agctggaccg cttcaaggag    660 cccctgcct  atggcccat  gtcgacatc  ctgtggagcg accccctgga ggactttgcc     720
```

```
aacgagaaga cccaggagca ctttacccac aacaccgtga gaggctgcag ctacttctac      780
tcctaccctg ctgtgtgcga gttcctgcag cacaacaacc tgctgagcat cctgagggcc      840
cacgaggccc aggatgccgg ctaccgcatg taccgcaagt cccagaccac cggcttcccc      900
tccctgatca ccatcttctc tgcccccaac tacctggacg tgtacaacaa caaagccgct      960
gtgctgaagt acgagaacaa cgtgatgaac atcggcagt tcaactgctc ccccacccc      1020 tactggctgc ccaacttcat ggacgtgttc gagtggagcg cccccttgt gggcgagaag      1080 gtgaccgaga tgctggtgaa cgtgctgaac atctgctccg acgatgagct gggcagcgag      1140
gaggacggct cgatggcgc caccgctgcc gccagaaagg aggtgatccg caataagatc      1200
agagccatcg gcaagatggc cagagtgttc tccgtgctgc gcgaggagag cgagtccgtg      1260 ctgacccctga agggcctgac ccccaccggc atgctgccct ccggcgtgct gagcggaggc      1320
aagcagaccc tgcagagcgc cacagtggag gccatcgagg ccgatgaggc catcaagggc      1380
ttctcccccc agcacaagat caccagcttc gaggaggcca agggcctgga ccggatcaac      1440
gagcggatgc acccagacg ggatgccatg cccagcgatg ccaacctgaa ctccatcaac      1500
aaggccctga ccagcgagac caacggcacc gacagcaacg gcagcaactc ctccaacatc      1560
cagtga                                                                1566

<210> SEQ ID NO 4
<211> LENGTH: 1566
<212> TYPE: DNA
<213> ORGANISM: Artificial Sequence
<220> FEATURE:
<223> OTHER INFORMATION: synthetic

<400> SEQUENCE: 4
atgagcgagc ccaaggccat cgaccccaag ctgtccacca ccgacagagt ggtgaaggcc       60 gtgcccttc ccccctccca ccgcctgacc gccaaggagg tgttcgacaa cgatggcaag      120
cccagagtgg acatcctgaa agcccaccctg atgaaggagg cagactgga ggagagcgtg      180 gccctgcgca tcatcaccga gggcgccagc atcctgcgcc aggagaagaa cctgctggat      240
atcgacgccc ctgtgaccgt gtgcggcgac atccacggac agtttttcga cctgatgaag      300
ctgttcgagg tgggcggctc tcccgccaac accagatacc tgttcctggg cgactacgtg      360
gacagaggct acttctctat cgagtgcgtg ctgtacctgt gggccctgaa gatcctgtac      420
cccaagaccc tgttcctgct gagaggcaac cacgagtgcc gccacctgac cgagtacttt      480
accttcaagc aggagtgcaa gatcaagtac agcgagcgcg tgtacgatgc ctgcatggac      540
gccttcgact gtctgccccct ggccgctctg atgaaccagc agttcctgtg tgtgcacgga      600
ggcctgagcc ccgagatcaa caccctggac gacatccgga gctggaccg cttcaaggag      660 ccccctgcct atggccccat gtgcgacatc ctgtggagcg acccctgga ggactttggc      720 aacgagaaga cccaggagca ctttacccac aacaccgtga gaggctgcag ctacttctac      780
tcctaccctg ctgtgtgcga gttcctgcag cacaacaacc tgctgagcat cctgagggcc      840
cacgaggccc aggatgccgg ctaccgcatg taccgcaagt cccagaccac cggcttcccc      900
tccctgatca ccatcttctc tgcccccaac tacctggacc ggtacaacaa caaagccgct      960
gtgctgaagt acgagaacaa cgtgatgaac atcggcagt tcaactgctc ccccacccc     1020 ttctggctgc ccaacttcat ggacgtgttc acctggtccc tgcccttgt gggcgagaag     1080 gtgaccgaga tgctggtgaa cgtgctgaac atctgctccg acgatgagct gggcagcgag     1140
```

```
gaggacggct tcgatggcgc caccgctgcc gccagaaagg aggtgatccg caataagatc    1200
agagccatcg gcaagatggc cagagtgttc tccgtgctgc gcgaggagag cgagtccgtg    1260
ctgaccctga agggcctgac ccccaccggc atgctgccct ccggcgtgct gagcggaggc    1320
aagcagaccc tgcagagcgc cacagtggag gccatcgagg ccgatgaggc catcaagggc    1380 ttctccccccc agcacaagat caccagcttc gaggaggcca agggcctgga ccggatcaac    1440
gagcggatgc cacccagacg ggatgccatg cccagcgatg ccaacctgaa ctccatcaac    1500
aaggccctga ccagcgagac caacggcacc gacagcaacg gcagcaactc ctccaacatc    1560
cagtga                                                              1566

<210> SEQ ID NO 5
<211> LENGTH: 519
<212> TYPE: DNA
<213> ORGANISM: Artificial Sequence
<220> FEATURE:
<223> OTHER INFORMATION: synthetic

<400> SEQUENCE: 5
atgggcaacg aggccagcta ccctctggag atgtgctccc acttcgacgc cgacgagatc      60
aagcggctgg gcaagcgctt caagaagctg gacctggaca cagcggcag cctgagcgtg     120 gaggagttta tgtctctgcc cgagctgcag cagaaccccc tggtgcagcg cgtgatcgac     180
atcttcgaca ccgacggcaa cggcgaggtg gacttcaagg agttcatcga gggcgtgagc     240
cagttcagcg tgaagggcga caaggagcag aagctgcggt tcgccttccg gatctacgat     300
atggataaag atggctatat ttctaatggc gagctgttcc aggtgctgaa gatgatggtg     360
ggcaacaata ccaagctggc cgatacccag ctgcagcaga tcgtggacaa gaccatcatc     420
aacgccgaca ggacggcga cggcagaatc agcttcgagg agttctgtgc cgtggtggga     480
ggcctggata ttcacaaaaa aatggtggtg gacgtgtga                           519

<210> SEQ ID NO 6
<211> LENGTH: 5
<212> TYPE: PRT
<213> ORGANISM: Artificial Sequence
<220> FEATURE:
<223> OTHER INFORMATION: synthetic

<400> SEQUENCE: 6

Val Ile Val Ile Thr
1               5

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
aaccaaaagt cttcgctgct                                                 20

<210> SEQ ID NO 8
<211> LENGTH: 20
<212> TYPE: DNA
<213> ORGANISM: Artificial Sequence
<220> FEATURE:
<223> OTHER INFORMATION: synthetic
```

```
<400> SEQUENCE: 8
ttgagaagcg acagccagtg                                               20

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
accaggagtt aatgattctt                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
tcctgagcaa gcacactgct                                               20

<210> SEQ ID NO 11
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: X = any naturally occuriring amino acid

<400> SEQUENCE: 11

Arg Xaa Lys Arg
1

<210> SEQ ID NO 12
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: X = any naturally occurring amino acid

<400> SEQUENCE: 12

Arg Xaa Arg Arg
1

<210> SEQ ID NO 13
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X = R or K
<220> FEATURE:
<221> NAME/KEY: MISC_FEATURE
<222> LOCATION: (3)..(3)
<223> OTHER INFORMATION: X = any naturally occurring amino acid
<220> FEATURE:
```

```
<221> NAME/KEY: MISC_FEATURE
<222> LOCATION: (4)..(4)
<223> OTHER INFORMATION: X = R or K

<400> SEQUENCE: 13

Xaa Arg Xaa Xaa Arg
1               5

<210> SEQ ID NO 14
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (2)..(3)
<223> OTHER INFORMATION: X = any naturally occurring amino acid

<400> SEQUENCE: 14

Arg Xaa Xaa Arg
1

<210> SEQ ID NO 15
<211> LENGTH: 4
<212> TYPE: PRT
<213> ORGANISM: Artificial Sequence
<220> FEATURE:
<223> OTHER INFORMATION: synthetic

<400> SEQUENCE: 15

Arg Gln Lys Arg
1

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
ugcucaggag agggagaug                                                  20

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
cuugcucagg agagggaga                                                  20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
uucucaauca gacuccaagc                                                 20

<210> SEQ ID NO 19
<211> LENGTH: 20
<212> TYPE: DNA
```

```
<213> ORGANISM: Artificial Sequence
<220> FEATURE:
<223> OTHER INFORMATION: synthetic

<400> SEQUENCE: 19
gggccaaauc agccuuuccu                                                   20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
ucagaacagc aacauuugaa                                                   20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
aagggccaga cuggcaccaa                                                   20

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
ccccaaguga aaacagaaaa                                                   20

<210> SEQ ID NO 23
<211> LENGTH: 20
<212> TYPE: DNA
<213> ORGANISM: Artificial Sequence
<220> FEATURE:
<223> OTHER INFORMATION: synthetic

<400> SEQUENCE: 23
uacugucagg caagcuuucc                                                   20

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
acugucaggc aagcuuuccu                                                   20

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
ggaggacaga uguaccacua                                                   20
```

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
ccuuucucaa cagcaggauc                                                    20

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
auuccaauuu ucggaaccaa                                                    20

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
uuccaauuuu cggaaccaac                                                    20

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
aggugccaag gaucuggaga                                                    20

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
ggucgaacag uuuuuucuaa                                                    20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
uaucgaaaau gucuucaggc                                                    20

<210> SEQ ID NO 32
<211> LENGTH: 20
<212> TYPE: DNA
<213> ORGANISM: Artificial Sequence
<220> FEATURE:

<223> OTHER INFORMATION: synthetic

<400> SEQUENCE: 32
ucuucaggcu ggaaugaacc                                               20

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
cuucaggcug gaaugaaccu                                               20

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
acagcucgaa aaacaaagaa                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
ggaauucagc aggccacuac                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
gaauucagca ggccacuaca                                               20

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
accacaacuc accccuaccc                                               20

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
uuaccacaac ucaccccuac                                               20

```
<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
ugauccucca aguugagucu                                                   20

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
cuccaaguug agucuggaac                                                   20

<210> SEQ ID NO 41
<211> LENGTH: 20
<212> TYPE: DNA
<213> ORGANISM: Artificial Sequence
<220> FEATURE:
<223> OTHER INFORMATION: synthetic

<400> SEQUENCE: 41
ggaugaccaa augacccuac                                                   20

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
acauccagga guacugcagu                                                   20

<210> SEQ ID NO 43
<211> LENGTH: 20
<212> TYPE: DNA
<213> ORGANISM: Artificial Sequence
<220> FEATURE:
<223> OTHER INFORMATION: synthetic

<400> SEQUENCE: 43
aacauccagg aguacugcag                                                   20

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
aggcuucagg uaucuuauga                                                   20

<210> SEQ ID NO 45
<211> LENGTH: 20
<212> TYPE: DNA
<213> ORGANISM: Artificial Sequence
<220> FEATURE:
<223> OTHER INFORMATION: synthetic
```

```
<400> SEQUENCE: 45
caggcuucag guaucuuaug                                              20

<210> SEQ ID NO 46
<211> LENGTH: 20
<212> TYPE: DNA
<213> ORGANISM: Artificial Sequence
<220> FEATURE:
<223> OTHER INFORMATION: synthetic

<400> SEQUENCE: 46
aagagccaag agcuauuuga                                              20

<210> SEQ ID NO 47
<211> LENGTH: 20
<212> TYPE: DNA
<213> ORGANISM: Artificial Sequence
<220> FEATURE:
<223> OTHER INFORMATION: synthetic

<400> SEQUENCE: 47
uuaucaacug acaaaacucu                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic

<400> SEQUENCE: 48
uaucaacuga caaaacucuu                                              20

<210> SEQ ID NO 49
<211> LENGTH: 20
<212> TYPE: DNA
<213> ORGANISM: Artificial Sequence
<220> FEATURE:
<223> OTHER INFORMATION: synthetic

<400> SEQUENCE: 49
uuuaucaacu gacaaaacuc                                              20

<210> SEQ ID NO 50
<211> LENGTH: 20
<212> TYPE: DNA
<213> ORGANISM: Artificial Sequence
<220> FEATURE:
<223> OTHER INFORMATION: synthetic

<400> SEQUENCE: 50
cuuccaaaca uuuuuggaua                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic

<400> SEQUENCE: 51
ccaaucagau accaaaauau                                              20

<210> SEQ ID NO 52
<211> LENGTH: 20
```

```
<212> TYPE: DNA
<213> ORGANISM: Artificial Sequence
<220> FEATURE:
<223> OTHER INFORMATION: synthetic

<400> SEQUENCE: 52
aaccacauaa cauucuauaa                                               20

<210> SEQ ID NO 53
<211> LENGTH: 20
<212> TYPE: DNA
<213> ORGANISM: Artificial Sequence
<220> FEATURE:
<223> OTHER INFORMATION: synthetic

<400> SEQUENCE: 53
guuucaucaa aagugacugc                                               20

<210> SEQ ID NO 54
<211> LENGTH: 20
<212> TYPE: DNA
<213> ORGANISM: Artificial Sequence
<220> FEATURE:
<223> OTHER INFORMATION: synthetic

<400> SEQUENCE: 54
gcuguccuau auggaauaaa                                               20

<210> SEQ ID NO 55
<211> LENGTH: 20
<212> TYPE: DNA
<213> ORGANISM: Artificial Sequence
<220> FEATURE:
<223> OTHER INFORMATION: synthetic

<400> SEQUENCE: 55
uacucauuaa uaaucagauc                                               20

<210> SEQ ID NO 56
<211> LENGTH: 11
<212> TYPE: DNA
<213> ORGANISM: Artificial Sequence
<220> FEATURE:
<223> OTHER INFORMATION: synthetic

<400> SEQUENCE: 56
aaccgtaaaa t                                                        11

<210> SEQ ID NO 57
<211> LENGTH: 20
<212> TYPE: DNA
<213> ORGANISM: Artificial Sequence
<220> FEATURE:
<223> OTHER INFORMATION: synthetic

<400> SEQUENCE: 57
gggccaaatc agcctttcct                                               20

<210> SEQ ID NO 58
<211> LENGTH: 20
<212> TYPE: DNA
<213> ORGANISM: Artificial Sequence
<220> FEATURE:
<223> OTHER INFORMATION: synthetic
```

<400> SEQUENCE: 58
tcagaacagc aacatttgaa                                          20

<210> SEQ ID NO 59
<211> LENGTH: 31
<212> TYPE: DNA
<213> ORGANISM: Artificial Sequence
<220> FEATURE:
<223> OTHER INFORMATION: synthetic

<400> SEQUENCE: 59
ttttattcca tataggacag cacaattacc t                              31

<210> SEQ ID NO 60
<211> LENGTH: 19
<212> TYPE: DNA
<213> ORGANISM: Artificial Sequence
<220> FEATURE:
<223> OTHER INFORMATION: synthetic

<400> SEQUENCE: 60
tttattccat ataggacag                                            19

<210> SEQ ID NO 61
<211> LENGTH: 21
<212> TYPE: DNA
<213> ORGANISM: Artificial Sequence
<220> FEATURE:
<223> OTHER INFORMATION: synthetic

<400> SEQUENCE: 61
ttttattcca tataggacag c                                         21

<210> SEQ ID NO 62
<211> LENGTH: 15
<212> TYPE: DNA
<213> ORGANISM: Artificial Sequence
<220> FEATURE:
<223> OTHER INFORMATION: synthetic

<400> SEQUENCE: 62
gattattaat gagta                                                15

<210> SEQ ID NO 63
<211> LENGTH: 20
<212> TYPE: DNA
<213> ORGANISM: Artificial Sequence
<220> FEATURE:
<223> OTHER INFORMATION: synthetic

<400> SEQUENCE: 63
gatctgatta ttaatgagta                                           20

<210> SEQ ID NO 64
<211> LENGTH: 20
<212> TYPE: DNA
<213> ORGANISM: Artificial Sequence
<220> FEATURE:
<223> OTHER INFORMATION: synthetic

<400> SEQUENCE: 64
tactcattaa taatcagatc                                           20

<210> SEQ ID NO 65

```
<211> LENGTH: 23
<212> TYPE: DNA
<213> ORGANISM: Artificial Sequence
<220> FEATURE:
<223> OTHER INFORMATION: synthetic

<400> SEQUENCE: 65
tcagaacagc aacatttgaa ggg                                              23

<210> SEQ ID NO 66
<211> LENGTH: 5077
<212> TYPE: DNA
<213> ORGANISM: Artificial Sequence
<220> FEATURE:
<223> OTHER INFORMATION: synthetic

<400> SEQUENCE: 66
ctttaacaga agattcagtt tgaagaatag ggctctttgt tagtacttct gcttttaact       60
ctttaatctc aagctaacac ttaacgaatt tacaaataag gcagcacaac ttttgactat      120
gtaagtaagg gtatcattta ttgtaatata agaacatatt ctaaaacagc tgaatgacca      180
tgcacaacac aatatgatat tatgagacat tatactctcc tgaatttata taattttcg       240 ttaagatatc tgttaatgag caacattatt ttaaaaatgt taaataaaat cctcaccgtt      300
ggccaatggg atactgaaaa ccactattta aggaaaaaac ctgaaatggt tacgtacaga      360
tgtcacttag gttgtctacc tttcctactt tcaaaaggcc acttaaactt attcatataa      420
aaaagcacat gaatctttag agaacacata taaatcaatg aagatttaca tctattaatc      480
taccttaaat gtaccattct taagaaacag aaaaacactg atcttacctt gaatagccat      540
tagaaaaaac tgttcgacca gggaagttca gagtccccag agaagtcaag ttgtcatctc      600
cagatccttg gcacctattc caattttcgg aaccaacggg aattggtgga atgacattaa      660
aaataggctt ctgatcctgc tgttgagaaa gggatgctgt attcatgtca tagtggtaca      720
tctgtcctcc agaggtactc acaccatgaa cagaaatggc agacatttta ttaccaatta      780
tatttgctcc aggaaagctt gcctgacagt aaactgtgcc cagtttctct tgcttaatta      840 ccccagggt gcagagttcg atgaaatctt ctttttctgt tttcacttgg ggcagtgtta      900
cattactggg gcttgacaaa accagatctc cattatcctt aattttgggt ttagtgtccg      960
gtaaaatgag aggcttgcag tcctcattcg agtttccttc caaaaggaat gaatcgtctt     1020
ctcccgccag aggagaaagc aaacagtttt catctatcaa caggtctgat ctccaaggac     1080
tctcattcgt ctctttacct ggggacccag aagaaaactc caaatcctgc aaaatgtcaa     1140
aggtgctttg gtctgtggta tacaatttca cattgccacc gttggtgcca gtctggccct     1200
tcaaatgttg ctgttctgaa gatacatcag agtgagtttt tggaaactcc ttctctgtgg     1260
gggcagcaga cacagcagtg gatgctgaac tcttggggtt ctctggaaca ctggtcgacc     1320
tattgaggtt tgcaatgctt tcttccaaaa gctttaagtc tgtttccccc gaggaaaggc     1380
tgatttggcc ctgctgtggg aatcccaggt catttcccat cacttttgtt tctgtctctc     1440
ccatatacag tcccattgag agtgaaactg ctttggacag atctggctat cgatcacgag     1500
actagcctcg agaagcttga tatcgaattc cacggggttg gacgcgtctt aattaaggat     1560
ccaaggtcag gaacagagaa acaggagaat atgggccaaa caggatatct gtggtaagca     1620
gttcctgccc cggctcaggg ccaagaacag ttggaacagc agaatatggg ccaaacagga     1680
tatctgtggt aagcagttcc tgccccggct cagggccaag aacagatggt ccccagatgc     1740
ggtcccgccc tcagcagttt ctagagaacc atcagatgtt tccagggtgc cccaaggacc     1800
```

```
tgaaatgacc ctgtgcctta tttgaactaa ccaatcagtt cgcttctcgc ttctgttcgc    1860
gcgcttctgc tccccgagct ctatataagc agagctcgtt tagtgaaccg tcagatcgcc    1920
tggagacgcc atccacgctg ttttgacctc catagaagac accgactcta gaggatcgat    1980
cccccgggct gcaggaattc aagcgagaag acaagggcag aaagcaccat gggcaacgag    2040
gccagctacc ctctggagat gtgctcccac ttcgacgccg acgagatcaa gcggctgggc    2100
aagcgcttca gaagctggaa cctggacaac agcggcagcc tgagcgtgga ggagtttatg    2160
tctctgcccg agctgcagca gaaccccctg gtgcagcgcg tgatcgacat cttcgacacc    2220
gacggcaacg cgaggtggac cttcaaggag ttcatcgagg cgtgagcca gttcagcgtg     2280
aagggcgaca aggagcagaa gctgcggttc gccttccgga tctacgatat ggataaagat    2340
ggctatattt ctaatggcga gctgttccag gtgctgaaga tgatggtggg caacaatacc    2400
aagctggccg ataccagct gcagcagatc gtggacaaga ccatcatcaa cgccgacaag    2460
gacggcgacg gcagaatcag cttcgaggag ttctgtgccg tggtgggagg cctggatatt    2520
cacaaaaaaa tggtggtgga cgtgctcgag ggcggcggag agggcagagg aagtcttcta    2580
acatgcggtg acgtggagga gaatcccggc cctagggtaa gcaaggggga ggagctgttc    2640
accggcgtag tacctatact ggtcgagttg gatggggacg tgaacggcca taaattctct    2700
gtgtctgggg agggcgaagg tgatgcgacc tacggaaagc tcaccctcaa attcatttgt    2760
acaacgggta agctgcctgt tccgtggccc accttggtaa ctaccttgac ttatggtgtc    2820
cagtgcttct ccaggtaccc agatcacatg aagcagcacg acttcttcaa atccgccatg    2880
cctgaaggct atgtgcaaga gcggacaatt ttttttaagg acgatggcaa ctataagact    2940
cgagccgaag ttaaatttga gggagacacc cttgtcaata ggatcgagct aaaggcatt    3000
gattttaagg aagacggaaa tatattgggc cataagctgg agtataacta caatagtcat    3060
aacgtgtaca tcatggctga caagcagaag aacgggatta aggtaaattt taagatcagg    3120
cataacatag aggacgggag cgtccaactt gccgaccact accagcaaaa taccccgata    3180
ggcgatggtc ctgtactgtt gccggataat cactacctct ctacgcaatc cgcgcttagt    3240
aaggatccta acgagaaacg cgaccacatg gtgcttctgg agttcgtaac tgctgctggc    3300
atcacacttg gcatggacga attgtacaaa tagcgctgat cagcctcgac tgtgccttct    3360
agttgccagc catctgttgt ttgcccctcc cccgtgcctt ccttgaccct ggaaggtgcc    3420
actcccactg tccttttccta ataaaatgag gaaattgcat cgcattgtct gagtaggtgt    3480
cattctattc tggggggtgg ggtggggcag gacagcaagg gggaggattg ggaagacaat    3540
agcaggcatg ctggggaagc tcgattgaga agcgacagcc agtgagggtg aagacgcaga    3600
aaccttcaca gtagcctcc ctcttagggt tttatagaag tccatcacat ctcccctctc     3660
ctgagcaagc acactgctgg ggttttcttc tctaccagga gttaatgatt ctttggagtc    3720
catcagtgaa tatcaactac aaaacaaaaa acaaaaacgg ggggaaaaca tcataagctc    3780
taaagtcaca ttatcttcct gatccgatta gtaagaggca gcttgttaaa tgaaccttt    3840
agttaactcc gaatcaaatt ctttgttacc agaagagtag tttctatctt ccagaataaa    3900
aagccatgtc cctgctcccc attcagcatg ccacatttaa aagtacaatg caatccattt    3960
gcacagctga gggcaaaagt gtatcgaact aagcttggct attcatcctg ccgctcactg    4020
aacgtgtagc tttgttaatc acagacatta taattcatta catctgatta ttctgaaggt    4080
tcaagttgat gtcaaagtat ttaatttcaa aaaaaggaag tgtgatcatt aaaattccta    4140
```

```
cctcttttca atcacggctg tttgcttttc tgagaaccaa tacatataac atttgataaa    4200
tactatgcta gaattctcaa tccctaatta cttccaaatt tccctcctac cagctagtca    4260
cacatccaaa cctttgagta caaccaactg gtgaaccatg cacgttttct ttgaaaaata    4320
aacaatgctg atctgcttat cttccgacag gctgggaaaa ggcttttttaa cccatacttc    4380 tgactggatg tgcctacctc caaattttgg atatatgaaa tgagatacac tttatatagg    4440
ccaactaaaa tttagatttt aaagagcaga agagaaggtg tagtagtttc tcactacgtt    4500
gttagcttac ataacttaaa tatagctgac ccttatcata actcacaaaa acatctagat    4560
taagctacat ttgtttacat tgcttgagat cctcaatatg aaatgctatt acatctctaa    4620
gttctttcct ttccaaacaa atatcgaagt actgaaaaat ggaaaaacac agaaccgtaa    4680
aatcacattc atataaattc aggtacaact gtatccagta aaatgttcaa aataattttc    4740
tctgccttca cctatccaaa ccttcaccta tcccaattct cagcctattc tcaagagagt    4800
aagactgtta gtatatcgtt aatcagggtg ttttaagaga tgggctaaga cggagaagcg    4860
catttgggac actatagtca aatcccgtcc aataaaaggt aacttttcct atgcgatgac    4920
gttaggcagc ataaatgtca ctggccctca ctgaaaagtg aatatgaagg tagagagagg    4980
ggtgtggact tgccactaca aatcttgagg gtaaactgct tatctcccca cctctctgcc    5040
ccgtttatct gaggcgataa cgatctctaa acacgag                             5077

<210> SEQ ID NO 67
<211> LENGTH: 16
<212> TYPE: PRT
<213> ORGANISM: Artificial Sequence
<220> FEATURE:
<223> OTHER INFORMATION: synthetic

<400> SEQUENCE: 67

Met Ala Gly Pro His Pro Val Ile Val Ile Thr Gly Pro His Glu Glu
1               5                   10                  15
```

DRUG-RESISTANT IMMUNE CELLS AND METHODS OF USE THEREOF

CROSS-REFERENCE TO RELATED APPLICATIONS

This application is a National Stage application under 35 U.S.C. § 371 of International Application No. PCT/US2019/032686, having an International Filing Date of May 16, 2019, which claims priority to U.S. Application Provisional Application No. 62/672,868, filed on May 17, 2018 which is incorporated herein by reference as if set forth in its entirety.

BACKGROUND

Regulatory T cells (Tregs) are critical to the maintenance of immune cell homeostasis as evidenced by the catastrophic consequences of genetic or physical ablation of the Treg population. Specifically, Treg cells maintain order in the immune system by enforcing a dominant negative regulation on other immune cells. Broadly classified into natural or adaptive (induced) Tregs; natural Tregs are CD4+CD25+ T-cells which develop, and emigrate from the thymus to perform their key role in immune homeostasis. Adaptive Tregs are non-regulatory CD4+ T-cells which acquire CD25 (IL-2R alpha) expression outside of the thymus, and are typically induced by inflammation and disease processes, such as autoimmunity and cancer.

Regulatory T cells (Tregs) suppress exuberant immune system activation and promote immunologic tolerance. Because Tregs modulate both innate and adaptive immunity, there has recently been intense interest in using Tregs for immunotherapy. Conditions that require clinical tolerance to improve outcomes—autoimmune disease, solid organ transplantation, and hematopoietic stem cell transplantation—may benefit from Treg immunotherapy. Barriers to clinically feasible Treg immunotherapy include Treg stability, off-cell effects, and demonstration of cell preparation purity and potency. Clinical trials involving Treg adoptive transfer to treat graft versus host disease (GVHD) preliminarily demonstrated the safety and efficacy of Treg immunotherapy in humans. In these trials, Tregs have been found to not persist longer than two weeks in the blood of GVHD patients.

Thus, there is a need in the art to develop immune cells that overcome barriers such as short persistence. In particular, there is a need in the art to develop Tregs that have increased persistence in vivo.

SUMMARY

Steroids and/or calcineurin inhibitors represent standard of care prophylaxis when treating subjects with graft versus host disease (GVHD) and may inhibit Treg persistence and function. Treg suppression of T effector (Teff) cells in combination with standard of care GVHD prophylaxis (e.g., calcineurin inhibitors, steroids) may directly inhibit Treg persistence and function. The present invention is based on the discovery that immune cells (e.g., Tregs) genetically modified to be resistant to steroids and/or calcineurin inhibitors have enhanced function and viability. The present invention provides steroid and/or calcineurin inhibitor resistant immune cells (e.g., Tregs). The present invention also provides methods of making such genetically modified immune cells, and methods of using the same to treat alloresponses and/or alloimmunity in which steroids and/or calcineurin inhibitors are used as prophylaxis.

In a first aspect, provided herein is a steroid-resistant genetically-modified hematopoietic cell or precursor cell thereof, comprising a genetic modification in a gene locus encoding for NR3C1, wherein the modification is capable of downregulating gene expression of NR3C1, wherein the modification is located in an exon, a splice donor, or a splice acceptor of NR3C1, and wherein the modified cell is rendered steroid-resistant as a result of said genetic modification. The genetic modification can be mediated by a CRISPR-Cas system, a CRISPR-Cpf1 system, a Cas9 orthologue, a Cas9 paralog, a Cas-related family member, zinc fingers, TALENs, or a meganuclease. The modification can be an indel. The indel can be located in exon 2 of NR3C1. The indel in NR3C1 can be mediated by a CRISPR system. The CRISPR system can comprise a CRISPR nuclease and a guide RNA. The guide RNA can comprise a guide sequence that is sufficiently complementary with a target sequence in exon 2 of NR3C1. The guide RNA can comprise a nucleic acid sequence set forth in any one of SEQ ID NOs: 7-10. The guide RNA can comprise a nucleic acid sequence set forth in SEQ ID NO:8. The modification can be a base pair substitution. The substitution in NR3C1 can be mediated by a CRISPR system. The CRISPR system can comprise a base editor and a guide RNA. The base editor can comprise a CRISPR deactivated or nicking DNA binding domain or a variant thereof, and a base-editing domain. The CRISPR deactivated or nicking DNA binding domain can be a Cas9 domain. The CRISPR deactivated or nicking DNA binding domain can be a variant Cas9 domain. The variant Cas9 domain can be a nuclease-inactive Cas9 domain. The base-editing domain can be a deaminase domain. The deaminase domain can have specificity for cytosine or adenine. The deaminase domain can be a cytidine or an adenosine deaminase. The substitution can introduce a premature stop codon in NR3C1, thereby resulting in downregulated gene expression of NR3C1. The guide RNA can comprise a guide sequence that is sufficiently complementary with a target sequence in an exon of NR3C1. The guide RNA can comprise a guide sequence that is sufficiently complementary with a target sequence in exon 2 of NR3C1. The guide RNA can comprise a nucleic acid sequence set forth in any one of SEQ ID NOs: 17-54. The guide RNA can comprise a guide sequence that is sufficiently complementary with a target sequence comprising a splice acceptor or a splice donor of NR3C1. The substitution can be capable of disrupting splicing of an NR3C1 mRNA, thereby resulting in downregulated gene expression of NR3C1. The guide RNA can comprise a nucleic acid sequence set forth in any one of SEQ ID NO 55 or 56. The modified cell can be resistant to a corticosteroid. The modified cell can be resistant to a glucocorticosteroid. The glucocorticosteroid can be selected from the group consisting of a progesterone-type glucocorticosteroid, a hydrocortisone-type glucocorticosteroid, a methasone-type glucocorticosteroid, and a acetonide-type glucocorticosteroid. The glucocorticosteroid can be selected from the group consisting of dexamethasone, betamethasone, hydrocortisone (cortisol), prednisone, prednisolone, loteprednol, deflazacort, methylprednisolone, triamcinolone, fludrocortisone, and deoxycorticosterone.

In another aspect, provided herein is a calcineurin inhibitor (CNI)-resistant, genetically-modified hematopoietic cell or precursor cell thereof, comprising an exogenous calcineurin inhibitor (CNI) resistance gene in the genome of the cell, wherein the CNI-resistance gene is inserted as a result of CRISPR-mediated homology directed repair (HDR) and wherein the modified cell is rendered CNI-resistant as a result of said resistance gene. The calcineurin inhibitor resistance gene can be inserted at a gene locus encoding for NR3C1. The calcineurin inhibitor resistance gene can be a mutant form of a Calcineurin A (CNa) gene selected from the group consisting of PPP3Ca, PPP3Cb and PPP3Cc or a mutant form of the Calcineurin B (CNb) gene selected from the group consisting of PPP3R1 and PPP3R2. The mutant calcineurin gene can be inserted into the NR3C1 locus via homologous recombination using an exogenous donor DNA sequence. The exogenous donor DNA sequence can comprise the nucleic acid sequence set forth in SEQ ID NO:11. The calcineurin inhibitor resistance gene can encode for a calcineurin variant protein. The calcineurin variant protein can be selected from the group consisting of CNa12, CNa22, and CNb30. The calcineurin variant can comprise the amino acid sequence set forth in any one of SEQ ID NOs: 3-5. The calcineurin variant protein can bind a calcineurin inhibitor but not calcineurin, thereby resulting in sequestration of the calcineurin inhibitor and prevention of calcineurin inhibition. The modified cell can be resistant to a calcineurin inhibitor selected from the group consisting of Cyclosporin A (CsA), Voclosporin, Tacrolimus (FK-506, fujimycin), Pimecrolimus, and derivatives and analogs thereof.

In a further aspect, provided herein is a genetically modified, steroid-resistant and calcineurin inhibitor (CNI)-resistant hematopoietic cell or precursor cell thereof, comprising (1) a first genetic modification comprising an indel in a gene locus encoding for NR3C1, wherein the indel is capable of downregulating gene expression of NR3C1, and (2) a second genetic modification comprising an exogenous CNI resistance gene inserted in the genome of the cell, wherein the CNI resistance gene resides at the site of the indel in the gene locus encoding for NR3C1, wherein the modified cell is rendered steroid- and CNI-resistant as a result of said genetic modifications. The gene locus can correspond to exon 2 of NR3C1. The indel can be mediated by a CRISPR system comprising a guide RNA comprising a nucleic acid sequence set forth in any one of SEQ ID NOs: 7-10. The indel can be mediated by a CRISPR system comprising a guide RNA comprising the nucleic acid sequence set forth in SEQ ID NO:8.

In another aspect, provided herein is a genetically modified, steroid-resistant and calcineurin inhibitor (CNI)-resistant hematopoietic cell or precursor cell thereof, comprising (1) a first genetic modification comprising a modification in a NR3C1 gene locus, wherein the modification is capable of downregulating gene expression of NR3C1, and (2) a second genetic modification comprising an exogenous CNI resistance gene inserted in the genome of the cell, wherein the modified cell is rendered steroid- and CNI-resistant as a result of said genetic modifications. The first or second modification can be mediated by a CRISPR-Cas9 system, a CRISPR-Cpf1 system, a Cas9 orthologue, a Cas9 paralog, a Cas-related family member, zinc fingers, TALENs, or a meganuclease. The modification can be an indel. The indel can be located in exon 2 of NR3C1. The indel in NR3C1 can be mediated by a CRISPR system. The CRISPR system can comprise a CRISPR nuclease and a guide RNA. The guide RNA can comprise a guide sequence that is sufficiently complementary with a target sequence in exon 2 of NR3C1. The guide RNA can comprise a nucleic acid sequence set forth in any one of SEQ ID NOs: 7-10. The guide RNA can comprise a nucleic acid sequence set forth in SEQ ID NO:8. The modification can be a base pair substitution. The substitution in NR3C1 can be mediated by a CRISPR system. The CRISPR system can comprise a base editor and a guide RNA. The base editor can comprise a CRISPR deactivated or nicking DNA binding domain or a variant thereof, and a base-editing domain. The CRISPR deactivated or nicking DNA binding domain can be a Cas9 domain. The CRISPR deactivated or nicking DNA binding domain can be a variant Cas9 domain. The variant Cas9 domain can be a nuclease-inactive Cas9 domain. The base-editing domain can be a deaminase domain. The deaminase domain can have specificity for cytosine or adenine. The deaminase domain can be a cytidine or an adenosine deaminase. The substitution can introduce a premature stop codon in NR3C1, thereby resulting in downregulated gene expression of NR3C1. The guide RNA can comprise a guide sequence that is sufficiently complementary with a target sequence in an exon of NR3C1. The guide RNA can comprise a guide sequence that is sufficiently complementary with a target sequence in exon 2 of NR3C1. The guide RNA can comprise a nucleic acid sequence set forth in any one of SEQ ID NOs: 17-54. The guide RNA can comprise a guide sequence that is sufficiently complementary with a target sequence comprising a splice acceptor or a splice donor of NR3C1. The substitution can be capable of disrupting splicing of an NR3C1 mRNA, thereby resulting in downregulated gene expression of NR3C1. The guide RNA can comprise a nucleic acid sequence set forth in any one of SEQ ID NOs: 55-56. The modified cell can be resistant to a corticosteroid. The modified cell can be resistant to a glucocorticosteroid. The glucocorticosteroid can be selected from the group consisting of a progesterone-type glucocorticosteroid, a hydrocortisone-type glucocorticosteroid, a methasone-type glucocorticosteroid, and a acetonide-type glucocorticosteroid. The glucocorticosteroid can be selected from the group consisting of dexamethasone, betamethasone, hydrocortisone (cortisol), prednisone, prednisolone, loteprednol, deflazacort, methylprednisolone, triamcinolone, fludrocortisone, and deoxycorticosterone. The calcineurin inhibitor resistance gene can be a mutant form of a Calcineurin A (CNa) gene selected from the group consisting of PPP3Ca, PPP3Cb and PPP3Cc or a mutant form of the Calcineurin B (CNb) gene selected from the group consisting of PPP3R1 and PPP3R2. The calcineurin inhibitor resistance gene can encode for a calcineurin variant protein. The calcineurin variant protein can be selected from the group consisting of CNa12, CNa22, and CNb30. The calcineurin variant protein can comprise the amino acid sequence set forth in any one of SEQ ID NOs: 3-5. The calcineurin variant protein can bind a calcineurin inhibitor but not calcineurin, thereby resulting in sequestration of the calcineurin inhibitor and prevention of calcineurin inhibition. The mutant calcineurin gene can be inserted into the genome of the cell via homologous recombination using an exogenous donor DNA sequence. The mutant calcineurin gene can be inserted into the NR3C1 locus. The modified cell can be resistant to a calcineurin inhibitor selected from the group consisting of Cyclosporin A (CsA), Voclosporin, Tacrolimus (FK-506, fujimycin), Pimecrolimus, and derivatives and analogs thereof. The modified cell can be a modified immune cell. The modified cell can be a modified regulatory T cell (Treg). The modified cell can be an autologous cell. The modified cell can be an allogeneic cell. The modified cell can be isolated from a human subject. The human subject can have received a stem cell transplant or is a candidate for stem cell transplantation. The human subject can have received a solid organ transplant or is a candidate for solid organ transplantation. The human subject can be suffering from an autoimmune disorder. The human subject can be suffering from Graft vs. Host Disease (GVHD). The human subject can be suffering from Type 1 Diabetes.

In a further aspect, provided herein is a method for generating a modified hematopoietic cell or precursor cell thereof, comprising introducing into the cell a CRISPR system that produces a modification in a gene locus encoding for NR3C1, wherein the modification is capable of downregulating gene expression of NR3C1. The modification can be an indel in exon 2 of NR3C1. The CRISPR system can comprise a CRISPR nuclease and a guide RNA. The guide RNA can comprise a guide sequence that is sufficiently complementary with a target sequence in exon 2 of NR3C1. The guide RNA can comprise a nucleic acid sequence set forth in any one of SEQ ID NOs: 7-10. The guide RNA can comprise a nucleic acid sequence set forth in SEQ ID NO:8. The modification can be a base pair substitution. The CRISPR system can comprise a base editor and a guide RNA. The base editor can comprise a CRISPR deactivated or nicking DNA binding domain or a variant thereof, and a base-editing domain. The CRISPR deactivated or nicking DNA binding domain can be a Cas9 domain. The CRISPR deactivated or nicking DNA binding domain can be a variant Cas9 domain. The variant Cas9 domain can be a nuclease-inactive Cas9 domain. The base-editing domain can be a deaminase domain. The deaminase domain can have specificity for cytosine or adenine. The deaminase domain can be a cytidine or a adenosine deaminase. The substitution can introduce a premature stop codon in NR3C1, thereby resulting in downregulated gene expression of NR3C1. The guide RNA can comprise a guide sequence that is sufficiently complementary with a target sequence in an exon of NR3C1. The guide RNA can comprise a guide sequence that is sufficiently complementary with a target sequence in exon 2 of NR3C1. The guide RNA can comprise a nucleic acid sequence set forth in any one of SEQ ID NOs: 17-54. The guide RNA can comprise a guide sequence that is sufficiently complementary with a target sequence comprising a splice acceptor or a splice donor of NR3C1. The substitution can be capable of disrupting splicing of an NR3C1 mRNA, thereby resulting in downregulated gene expression of NR3C1. The guide RNA can comprise a nucleic acid sequence set forth in any one of SEQ ID NOs: 55-56. The CRISPR nuclease/base editor and the guide RNA can comprise a ribonucleoprotein (RNP) complex. The CRISPR nuclease/base editor and/or the guide RNA can be encoded by a polynucleotide. The polynucleotide can comprise a vector and/or a synthetic mRNA. The RNP or polynucleotide can be introduced by electroporation. The method can further comprise insertion of an exogenous calcineurin inhibitor resistance gene into the genome of the cell. Insertion of the exogenous calcineurin inhibitor resistance gene can be via homologous recombination. The insertion can occur at the site of the indel in a gene locus encoding NR3C1. The insertion can occur at the site of the indel in a gene locus encoding NR3C1. The insertion can occur at the site of the indel in the gene locus encoding NR3C1 via homologous recombination from an exogenous donor DNA sequence. The exogenous donor DNA sequence can comprise the nucleic acid sequence set forth in SEQ ID NO: 11. The exogenous donor DNA sequence can be introduced via viral transduction. The exogenous donor DNA sequence can be introduced via electroporation. The exogenous donor DNA sequence comprises a promoter in operable linkage to a nucleic acid encoding a reporter molecule. The promoter and the nucleic acid encoding the reporter molecule can be separated by a linker. The linker can comprise a T2A sequence. The calcineurin inhibitor resistance gene can be a mutant form of a Calcineurin A (CNa) gene selected from the group consisting of PPP3Ca, PPP3Cb and PPP3Cc or a mutant form of the Calcineurin B (CNb) gene selected from the group consisting of PPP3R1 and PPP3R2. The calcineurin inhibitor resistance gene can encode for a calcineurin variant protein. The calcineurin variant protein can be selected from the group consisting of CNa12, CNa22, and CNb30. The calcineurin variant protein can comprise the amino acid sequence set forth in any one of SEQ ID NOs: 3-5. The modified cell can be a modified immune cell. The modified cell can be a modified regulatory T cell (Treg). The modified cell can be an autologous cell. The modified cell can be an allogeneic cell. The modified cell can be isolated from a human subject. The human subject can have received a stem cell transplant or is a candidate for stem cell transplantation. The human subject can have received a solid organ transplant or is a candidate for solid organ transplantation. The human subject can be suffering from an autoimmune disorder. The human subject can be suffering from Graft vs. Host Disease (GVHD). The human subject can be suffering from Type 1 Diabetes.

In another aspect, provided herein is a method of achieving an immunosuppressive effect in a subject in need thereof, comprising administering to the subject the modified cell as provided herein. The subject can be suffering from an alloresponse and/or an autoimmune response.

In a further aspect, provided herein is a method for achieving a preventative therapeutic effect in a subject in need thereof, comprising administering to the subject, prior to onset of an alloresponse and/or autoimmune response, a population of the modified cell as provided herein. The alloresponse and/or autoimmune response can follow transplantation of a biological material. The biological material can be selected from the group consisting of a cell, a tissue, and an organ. The biological material can be allogeneic. The subject can be human. The human subject can have received a stem cell transplant or is a candidate for stem cell transplantation. The human subject can have received a solid organ transplant or is a candidate for solid organ transplantation. The human subject can be suffering from an autoimmune disorder. The human subject can be suffering from Graft vs. Host Disease (GVHD). The human subject can be suffering from Type 1 Diabetes. The modified cells can be administered in combination with a steroid and/or a calcineurin inhibitor. The steroid and/or calcineurin inhibitor can be administered prior to administration of the modified cells. The steroid and/or calcineurin inhibitor can be administered simultaneous to or after administration of the modified cells. The steroid can be a corticosteroid. The steroid can be a glucocorticosteroid. The glucocorticosteroid can be selected from the group consisting of a progesterone-type glucocorticosteroid, a hydrocortisone-type glucocorticosteroid, a methasone-type glucocorticosteroid, and a acetonide-type glucocorticosteroid. The glucocorticosteroid can be selected from the group consisting of dexamethasone, betamethasone, hydrocortisone (cortisol), prednisone, prednisolone, loteprednol, deflazacort, methylprednisolone, triamcinolone, fludrocortisone, and deoxycorticosterone. The calcineurin inhibitor can be selected from the group consisting of Cyclosporin A (CsA), Voclosporin, Tacrolimus (FK-506, fujimycin), Pimecrolimus, and derivatives and analogs thereof.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1 depicts a schematic showing one version of a Treg banking protocol of an embodiment of the present invention.

FIGS. 2A-2D depicts data showing the effects of Dexamethasone on Treg survival. Four experiments were performed as described. Data shown are aggregate data from all experiments and represent the mean±1 standard error of the mean. FIG. 2A depicts a schematic showing a timeline of culture conditions. FIG. 2B depicts a graph showing the effect of Dexamethasone on survival. FIG. 2C depicts a graph showing the effect of Dexamethasone on FOXP3+ CD127-cells. FIG. 2D depicts a graph showing the effect of Dexamethasone on suppressive activity. P values were ≤0.05 between the two groups at each Treg:PBMC ratio.

FIG. 3A depicts a schematic illustrating the process of gene transfer. T cells or Tregs were harvested and activated with CD3/CD28 beads for 48 h (fresh) or 72 h (frozen). The Neon electroporation device was used to deliver Cas9 mRNA or protein with a gene specific guide RNA. FIG. 3B depicts a schematic illustrating NR3C1 gene targeting. Four sites in exon 2 were identified and tested. Four candidates were identified. The candidates were tested using the Surveyor method. FIG. 3C depicts a schematic illustrating the Surveyor assay. Gene modified ("mutant amplicon") and unmodified ("wild type amplicon") are hybridized resulting in homo- or heteroduplexes. Heteroduplexes caused by pairing of gene edited and wild type sequences are cleaved by the Surveyor enzyme resulting in predictable DNA fragments.

FIGS. 4A-4D depicts CRISPR/Cas9-mediated NR3C1 knockout in Tregs. Guide RNA candidates GR1 and GR2 were electroporated into activated Tregs as a ribonucleoprotein particle (RNP) with the Cas9 peptide. FIG. 4A depicts a schematic illustrating the culture process. FIG. 4B depicts a plot assessing the survival of Tregs after 72 h 30 µg/mL of Dexamethasone was added in the conditions as indicated. FIG. 4C and FIG. 4D shows the molecular analysis of the NR3C1 locus pre-Dexamethasone (FIG. 4C) and post-Dexamethasone (FIG. 4D). The NR3C1 locus was amplified from the pool of cells and indel analysis was performed by TIDE. The total gene modification rates were 35% and 44% for the pre- and post-Dexamethasone cells, respectively. The graph corresponds to the indel pattern observed in each population. Without being bound by any theory, it is predicted that out of frame indels (e.g., those non-divisible by three) will result in gene inactivation. Y-axis indicates the number of indels as a total percentage. X-axis indicates indels relative to unmodified (shown as bar in position 0). Deletions are shown to the left of the 0 position and each bar is between 1-10 bp away from the target site. Insertions of +1 bp are shown to the right of the 0 position. Asterisks show +1, −1, and −7 bp insertions/deletions and the frequency of these events increased with Dexamethasone exposure (comparing FIG. 4C with FIG. 4D), Dark black bars in FIGS. 4C-4D indicate editing events <0.5%.

FIGS. 5A-5C depicts homology directed repair (HDR) in Tregs. FIG. 5A depicts the gene targeting strategy. A calcineurin resistant gene co-expressed with GFP was designed such that it could be targeted to exon 2 of the NR3C1 gene resulting in a loss of 21 amino acids. The donor was encapsulated in AAV-6 particles and screening was performed using an inside/out PCR with primers (indicated by horizontal arrows) within the donor and outside of the donor at the target locus. FIG. 5B depicts gene targeting optimization. Activated Tregs were electroporated with NR3C1 Cas9 RNPs and the different indicated amounts of AAV-6 donor were added. Inside/out PCR results are shown with Sanger sequencing confirmation of the junction between the donor and the adjacent locus sequence shown in FIG. 5C.

FIGS. 6A-6D depicts HDR in Tregs using GR2-Cas9 and AAV under optimal Treg expansion conditions rescues survival of glucocorticoid disrupted Tregs by insertion of calcineurin variant (CnB mut). FIG. 6A depicts a schematic illustrating the culture process. FIG. 6B (p≤0.07) depicts the fold expansion of control and calcineurin variant (CnB mut) AAV transduced Tregs over a 2 day period. FIG. 6C depicts the percent GFP expression under no or Dexamethasone conditions as listed for control (black) or calcineurin variant (CnB mut; gray).

FIG. 6D depicts the relative survival of Tregs that were mock transduced or exposed to the indicated Dexamethasone concentrations. P values are as indicated and represent aggregate data from four separate cultures.

FIG. 7A depicts a schematic illustrating the culture process used to obtain data for FIG. 7B. FIG. 7B depicts data showing the percent survival of Tregs that were cultured without drug (control) or with CsA or tacrolimus (FK506) (p=not significant for all comparisons). The percent survival relative to the control Tregs without drugs is shown. IL-2 concentration of 300 U/mL was used. FIG. 7C depicts a schematic illustrating the culture process used to obtain data for FIG. 7D. FIG. 7D depicts data showing the percent relative survival of Tregs without drug at IL-2 300 U/mL as compared to those cultured with the indicated concentrations of drug in the presence of IL-2 at 30, 100, or 300 U/mL as indicated. Mean values are shown±standard error of the mean for three (FIG. 7B) or four (FIG. 7D) separate cultures.

FIG. 10 depicts steroid based GVHD therapy in allogeneic BMT recipients. n=15 (BM-Circles), 16 (Vehicle-Squares) and 25 (Prednisolone-Triangles). BALB/c mice were lethally irradiated, given B6 BM+1.5 M T cells and steroids at 10 mg/kg/day day 3-28. Day 3 treatment was found to be significantly better than vehicle control (p=0.0016).

FIGS. 11A-11D depicts the monitoring of GVHD in mice. Human PBMC ($15 \times 10^6$) were injected into irradiated (50 rad) NSG mice±methylprednisolone (15 mg/kg), and signs of GVHD were monitored. FIG. 11A depicts a schematic illustration of the experiments indicating cohorts (n=7 mice each), dosing schedule, and analysis points. FIG. 11B depicts Kaplan-Meier survival curves for mice receiving PBMC only, or PBMC+prednisolone (p=0.104). FIG. 11C depicts disease progression monitored by weight loss (p=not significant). FIG. 11D depicts disease progression monitored by quantitating the number of PBMC-derived CD45+, CD4+, CD8+, and CD4+Foxp3+ T cells (p<0.03, <0.05, <0.03, and not significant, respectively). Animals were bled on day 19 for assessment.

FIGS. 12A-12D depicts the monitoring of GVHD in mice. Human PBMC ($15 \times 10^6$) were injected into irradiated (50 rad) NSG mice±FK506 (36 or 12 mg/kg) or CsA (80 mg/kg), and signs of GVHD were monitored. FIG. 12A depicts a schematic illustration of the experiments indicating cohorts (n=7 mice each for all groups, except CsA n=5), dosing schedule, and analysis points. FIG. 12B depicts Kaplan-Meier survival curves for mice receiving PBMC only, or PBMC+CNI (PBMC only vs. FK506 (36 mg/kg), p≤0.04). FIG. 12C depicts disease progression monitored by weight loss (p=not significant). FIG. 12D depicts disease progression monitored by quantitating the number of PBMC-derived CD45+, CD4+, CD8+, and CD4+Foxp3+ T cells (p<0.03, <0.05, <0.02, and not significant, respectively). Animals were bled on day 18 for assessment.

FIGS. 14A-14C depicts the effect on expansion after the various manipulations as indicated were performed.

DETAILED DESCRIPTION

Figure 3A:
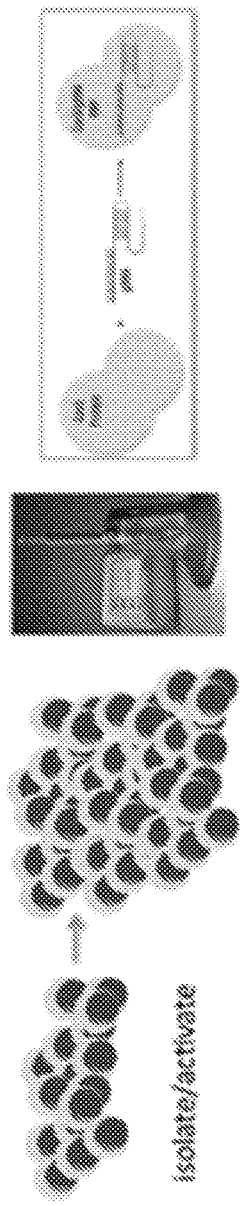
FIGS. 3A-3D depicts the process of gene editing of NR3C1 glucocorticoid receptor by CRISPR guide RNA and Cas9.

The present invention provides compositions and methods for modified hematopoietic cells or precursors thereof (e.g., modified Tregs) that are steroid and/or calcineurin inhibitor resistant. In some embodiments, the modified cells are genetically edited to disrupt one or more endogenous genes that are responsible for steroid-mediated reduction of cell persistence and survival. In some embodiments, the modified cells are genetically edited to introduce a calcineurin inhibitor resistance gene. In certain embodiments, modified cells of the present disclosure comprise one or more indels in the NR3C1 gene locus. In certain embodiments, modified cells of the present disclosure comprise one or more indels in the NR3C1 gene locus, and further comprise a calcineurin inhibitor resistance gene inserted into the one or more indels in the NR3C1 gene locus.

In some embodiments, the provided cells, compositions and methods provide for increased persistence and/or survival. For example, Tregs of the invention exhibit increased persistence and/or survival. In clinical settings, the administration of steroids and calcineurin inhibitors represent standard of care prophylaxis treatments for individuals that have undergone, e.g., allogeneic cell transplantation. Adoptive transfer of regulatory T cells is an approach to reduce the negative effects after allogeneic cell transplantation. It was found herein that steroids and/or calcineurin inhibitors negatively affect the persistence and survival of Tregs. As such, modified cells of the present disclosure are more persistent and long-lived in the presence of standard of care prophylaxis treatment.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, to "alleviate" a disease means reducing the severity of one or more symptoms of the disease.

As used herein, the term "autologous" is meant to refer to any material derived from the same individual to which it is later to be re-introduced into the individual.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of cells (e.g., Tregs). In one embodiment, the cells that are expanded ex vivo increase in number relative to the number originally present in the culture. In another embodiment, the cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the terms "genetically engineered" and "genetically modified" are used interchangeably and refer to a cell that has been modified to comprise a non-naturally occurring nucleic acid molecule that has been created or modified by the hand of man (e.g., using recombinant or gene editing DNA technology) or is derived from such a molecule (e.g., by transcription, translation, etc.). A cell that contains an exogenous, recombinant, synthetic, and/or otherwise modified polynucleotide is considered to be a genetically modified cell and, thus, non-naturally occurring relative to any naturally occurring counterpart. In some cases, genetically modified cells contain one or more recombinant nucleic acids. In other cases, genetically modified cells contain one or more synthetic or genetically engineered nucleic acids (e.g., a nucleic acid containing at least one artificially created insertion, deletion, inversion, or substitution relative to the sequence found in its naturally occurring counterpart).

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" or "immune suppressive" is used herein to refer to reducing overall immune response.

"Insertion/deletion", commonly abbreviated "indel," is a type of genetic polymorphism in which a specific nucleotide sequence is present (insertion) or absent (deletion) in a genome.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids. In certain embodiments, a modified cell may be "genetically modified" or "genetically edited", wherein one or more nucleic acids in the cell are altered.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "pluripotency" means a cell's ability to differentiate into form all lineages of the body or soma (i.e., the embryo proper), including cells of all three germ layers (the ectoderm, endoderm, and mesoderm).

As used herein, the term "pluripotent stem cell" refers to a cell capable of continued self-renewal and of capable, under appropriate conditions, of differentiating into cells of all three germ layers. Examples of pluripotent stem cells (PSCs) include embryonic stem cells (ESCs) and induced pluripotent stem cells (iPSCs). As used herein, "embryonic stem cells" or "ESCs" mean a pluripotent cell or population of pluripotent cells derived from an inner cell mass of a blastocyst. See, e.g., Thomson et al., *Science* 282:1145-1147 (1998). These cells express Oct-4, SSEA-3, SSEA-4, TRA-1-60, and TRA-1-81, and appear in vitro as compact colonies having a high nucleus to cytoplasm ratio and prominent nucleolus. As used herein, the term "iPS cell" or "iPSC" refers to a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007). IPSCs are substantially genetically identical to their respective differentiated somatic cell of origin, display characteristics similar to higher potency cells, such as ES cells, and cells are obtained by reprogramming non-pluripotent cells (e.g., multipotent cells, oligopotent cells, unipotent cells, and terminally differentiated cells) such as somatic cells. ESCs and iPSCs are available from various commercial suppliers.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Modified Cells

The present invention provides a modified cell (e.g., a modified pluripotent stem cell, a modified immune cell, a modified regulatory T cell, an immune cell derived from a modified pluripotent stem cell) that is resistant to the effects of steroids (e.g., glucocorticoids). The present invention provides a modified cell (e.g., an immune cell, a regulatory T cell) that is resistant to the effects of calcineurin inhibitors (e.g., CsA, FK506). In certain embodiments, the present invention provides a modified cell (e.g., an immune cell, a regulatory T cell) that is resistant to the effects of both steroids (e.g., glucorticoids) and calcineurin inhibitors (e.g., CsA, FK506). Also provided is a modified cell that is resistant to the effects of other immunosuppressor drugs (e.g., mTOR inhibitors, mycophenolic acid, methotrexate, fludarabine, pentostatin, cyclophosphamide, etc.). Also provided is a modified effector T cell (Teff) that is sensitive to the effects of steroids and/or calcineurin inhibitors.

Steroid-Resistant Cells

As described herein, steroids (e.g., glucocorticoids) represent standard of care prophylaxis when treating subjects with graft versus host disease (GVHD) and may reduce effector T cell (Teff) function as well as directly inhibit Treg persistence and function. Steroids may directly impact the survival of cells, for example, the survival of Tregs in the presence of the steroid dexamethasone is greatly diminished.

The present disclosure provides a steroid-resistant cell (e.g., a gene edited steroid-resistant pluripotent stem cell, a steroid-resistant regulatory T cell (Treg), steroid-resistant hematopoietic cell or precursor cell thereof). As used herein, a "steroid-resistant" cell refers to a cell that is resistant to the effects of a steroid (e.g., a glucocorticoid). As used herein, a cell which is "resistant or tolerant" to an agent means a cell which has been genetically modified so that the cell proliferates in the presence of an amount of an agent that inhibits or prevents proliferation of a cell without the modification.

A steroid-resistant cell of the present disclosure, when contacted with a steroid, exhibits minimal to no physiological changes. Effectively, a steroid-resistant cell does not interact with (e.g., bind) a steroid. Various methods of assessing whether a steroid-resistant cell is resistant to the effect of a steroid are known in the art. For example, the survival of cells in the presence of a steroid can be measured using cell counting technology, or with reporter-based technology. The skilled person will be able to determine the effect of a steroid on a steroid-resistant cell using the various methods known in the art.

In some embodiments, steroid resistance is achieved by gene editing of one or more endogenously expressed genes. As such, the present disclosure provides a gene edited steroid-resistant cell (e.g., a gene edited steroid-resistant pluripotent stem cell, a gene edited steroid-resistant Treg, a modified hematopoietic cell or precursor cell thereof). In some embodiments, a cell is genetically edited to disrupt the expression of one or more endogenously expressed genes, wherein the disruption results in a reduction, deletion, elimination, knockout or disruption in expression of one or more endogenously expressed genes, thereby conferring steroid resistance to the cell.

In some embodiments, a steroid-resistant cell of the present disclosure is genetically edited to disrupt the expression of one or more endogenous genes that encode for one or more nuclear receptors. Nuclear receptors are a class of proteins found within cells that are responsible for sensing steroid and thyroid hormones, and other molecules. These receptors work with other proteins to regulate the expression of specific genes. Various nuclear receptors are known in the art, and are broadly categorized into subfamilies, for example: subfamily 1, thyroid hormone receptor-like; subfamily 2, retinoid X receptor-like; subfamily 3, estrogen receptor-like; subfamily 4, nerve growth factor IB-like; and subfamily 5, steroidogenic factor-like, subfamily 6, germ cell nuclear factor-like. Each subfamily of nuclear receptors can be further categorized into groups. For example, nuclear receptors belonging to subfamily 3 can be further categorized into, for example: class A, estrogen receptor; class B, estrogen related receptor; and class C, 3-ketosteroid receptors. Several members of the nuclear receptors belonging to subfamily 3, class C, are known. For example, the NR3C1 gene (NCBI Reference Sequence NG_009062.1) encodes for the glucocorticoid receptor, the NR3C2 gene (NCBI Reference Sequence NG_013350.1) encodes for the mineralocorticoid receptor, the NR3C3 gene (NCBI Reference Sequence NG_016475.1) encodes for the progesterone receptor, and the NR3C4 gene (NCBI Reference Sequence NG_009014.2) encodes for the androgen receptor.

In certain embodiments, a steroid-resistant cell of the present disclosure is genetically edited to disrupt the expression of NR3C1. NR3C1 encodes for the glucocorticoid receptor (GR, or GCR). Glucocorticoids are a class of corticosteroids that bind to the glucocorticoid receptor, traditionally known for its role in regulating glucose metabolism, and synthesis in the adrenal cortex. As used herein, the terms "glucocorticoid" and "glucocorticosteroid" are used interchangeably. Glucocorticoids include, without limitation, progesterone-type glucocorticoids, hydrocortisone-type glucocorticoids, methasone-type glucocorticoids, and acetonide-type glucorticoids. Glucocorticoids include, without limitation, betamethasone, budesonide, cortisone, deflazacort, deoxycorticosterone, dexamethasone, fludrocortisone, hydrocortisone (cortisol), loteprednol, methylprednisolone, prednisolone, prednisone, and triamcinolone, and derivatives and analogs thereof.

As such, in some embodiments, a steroid-resistant cell (e.g., a gene edited steroid-resistant pluripotent stem cell, a steroid-resistant hematopoietic cell or precursor cell thereof) of the present disclosure is genetically edited (as defined by one or more DNA or RNA base alterations, insertions, deletions, substitutions, or conversions via a nucleotide binding reagent such as CRISPR/Cas9, CRISPR/Cas12a (Cpf1), Cas9 orthologues, paralogs, Cas related family members, zinc fingers, TALENs, or meganuclease candidates that are targeted to the NR3C1 locus leading to disruption or perturbation of expression of NR3C1 (e.g., via introduction of indels and/or substitution(s) into the NR3C1 locus (to include regulatory regions, exon(s), and intron(s)), wherein the steroid-resistant cell is resistant to one or more glucocorticoids selected from the group consisting of a progesterone-type glucocorticoid, a hydrocortisone-type glucocorticoid, a methasone-type glucocorticoid, and an acetonide-type glucorticoid. In some embodiments, a steroid-resistant cell of the present disclosure is genetically edited to disrupt the expression of NR3C1, wherein the steroid-resistant cell is resistant to one or more glucocorticoids selected from the group consisting of betamethasone, budesonide, cortisone, deflazacort, deoxycorticosterone, dexamethasone, fludrocortisone, hydrocortisone (cortisol), loteprednol, methylprednisolone, prednisolone, prednisone, and triamcinolone, and derivatives and analogs thereof. In certain embodiments, a steroid-resistant cell of the present disclosure is genetically edited to disrupt the expression of NR3C1, wherein the steroid-resistant cell is resistant to dexamethasone.

In some embodiments, a steroid-resistant cell (e.g., a gene edited steroid-resistant pluripotent stem cell, a steroid-resistant hematopoietic cell or precursor cell thereof) of the present disclosure exhibits increased cell survival in the presence of a steroid (e.g., dexamethasone). In some embodiments, a steroid-resistant cell genetically edited to disrupt the expression of NR3C1 (e.g., via introduction of indels and/or substitution(s) into the NR3C1 locus (to include regulatory regions, exon(s), and intron(s)) exhibits increased cell survival in the presence of a steroid. In certain embodiments, a steroid-resistant cell genetically edited to disrupt the expression of NR3C1 exhibits increased cell survival in the presence of dexamethasone. In some embodiments, the increase in cell survival is at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 205%, at least 210%, at least 215%, at least 220%, at least 225%, at least 230%, at least 235%, at least 240%, at least 245%, at least 250%, at least 255%, at least 260%, at least 265%, at least 270%, at least 275%, at least 280%, at least 285%, at least 290%, at least 295%, at least 300%, at least 350%, at least 400%, or more.

Calcineurin Inhibitor-Resistant Cells

As described herein, calcineurin inhibitors (CNIs) represent standard of care prophylaxis when treating subjects with graft versus host disease (GVHD) and may reduce effector T cell (Teff) function as well as directly inhibit Treg persistence and function. Calcineurin inhibitors may directly impact the survival of cells, for example, the survival of Tregs in the presence of the steroid dexamethasone is greatly diminished.

The present disclosure provides a CNI-resistant cell (e.g., a CNI-resistant pluripotent stem cell, a CNI-resistant regulatory T cell (Treg), a CNI-resistant hematopoietic cell or precursor cell thereof). As used herein, a "calcineurin inhibitor-resistant" cell refers to a cell that is resistant to the effects of a CNI (e.g., cyclosporin). A CNI-resistant cell of the present disclosure, when contacted with a CNI, exhibits minimal to no physiological changes. Effectively, a CNI-resistant cell does not interact with (e.g., bind) a CNI. Various methods of assessing whether a CNI-resistant cell is resistant to the effect of a CNI are known in the art. For example, the survival of cells in the presence of a CNI can be measured using cell counting technology, or with reporter-based technology. The skilled person will be able to determine the effect of a CNI on a CNI-resistant cell using the various methods known in the art.

Calcineurin is a heterodimeric calcium and calmodulin dependent serine-threonine phosphatase which is central to T cell activation. After engagement of the T cell receptor, calcineurin dephosphorylates the transcription factor NFAT (nuclear factor of activated T cell), allowing it to translocate to the nucleus and activate key target genes such as IL-2 (interleukin 2). FK506 (tacrolimus; fujimycin) in complex with FKBP12 (FK506 binding protein), or CsA (cyclosporin A) in complex with CyPA (cyclophilin A), block NFAT access to calcineurin's active site, preventing its dephosphorylation, and thereby inhibiting T cell activation. Calcineurin is formed by two subunits: A, which is a catalytic subunit (CnA) responsible for its phosphatase activity, and B, a regulatory subunit (CnB) that is particularly responsive to intracellular calcium and regulates CnA activation.

Calcineurin is the target of a class of drugs called calcineurin inhibitors, which includes without limitation, cyclosporin, voclosporin, pimecrolimus, and tacrolimus, and derivatives and analogs thereof. Calcineurin inhibitors (CNIs) bind intracellular proteins called immunophilins: cyclophilins in the case of cyclosporin A (CsA; also known in the art as clyclosporin), and the FK-binding proteins in the case of tacrolimus (also known as FK506). This complex then binds to calcineurin, leading to an inhibition of its activity, and hence inhibiting T cell activation. Cyclosporin is a cyclic endecapeptide with N-methylated amino acids that make the molecule resistant to inactivation by the gastrointestinal tract and hence usable as an oral immunosuppressive drug. Voclosporin is an analog of cyclosporine with enhanced action against calcineurin and greater metabolic stability. Tacrolimus (FK506; fujimycin) is a macrolide antibiotic. Pimecrolimus and tacrolimus belong to the ascomycin class of macrolactam immunosuppressives, acting by the inhibition of T cell activation via the calcineurin pathway and inhibition of the release of numerous inflammatory cytokines.

In some embodiments, as described herein, CNI resistance can be achieved by introducing into the cell a calcineurin inhibitor resistance gene. As such, the present disclosure provides a modified cell that is resistant to a CNI (e.g., a CNI-resistant pluripotent stem cell, a modified CNI-resistant Treg). In some embodiments, a cell is modified to express a calcineurin inhibitor resistance gene. Where a cell is modified to express a CNI resistance gene, the cell may be further modified to disrupt the expression of an endogenous calcineurin gene.

In some embodiments, a calcineurin inhibitor resistance gene includes a variant of calcineurin that has been modified at key amino acid residues to disrupt docking of either or both FK506-FKBP12 and CsA-CyPA to produce calcineurin mutants resistant to FK506 and/or CsA. The calcineurin inhibitor resistant gene of the present invention can be a nucleic acid sequence encoding a variant of calcineurin that resistant to calcineurin inhibitor such as FK506 and/or CsA.

In some embodiments, the calcineurin variant binds FK506 but not calcineurin, resulting in sequestration of the drug and prevention of calcineurin inhibition.

In some embodiments, the calcineurin variant can comprise one or more substitutions of the wild type calcineurin heterodimer A at one or more positions selected from the group consisting of V314, Y341, M347, T351, W352, L354, and K360. In some embodiments, the calcineurin variant can comprise a double substitution of the wild type calcineurin heterodimer A, for example, at positions T351 and L354, or V314 and Y341. In some embodiments, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue of SEQ ID NO:1. Correspondence of amino acid positions described herein is frequently expressed in terms of the positions of the amino acids of the form of the wild-type human calcineurin heterodimer A polypeptide set forth in SEQ ID NO:1 (GenBank: ACX34092.1). In some embodiments, the calcineurin variant can comprise one or more substitutions of the wild type calcineurin heterodimer B at one or more positions selected from the group consisting of V120, N123, L124, or K125. In some embodiments, the calcineurin variant can comprise a double substitution of the wild type calcineurin heterodimer B, for example, at positions L124 and K125. In some embodiments, the valine at position 120 can be replaced with a serine, an aspartic acid, phenylalanine or leucine residue; the asparagines at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence SEQ ID NO:2. Correspondence of amino acid positions described herein is frequently expressed in terms of the positions of the amino acids of the form of wild-type human calcineurin heterodimer B polypeptide set forth in SEQ ID NO:2 (GenBank: ACX34095.1). Calcineurin variants are described in Brewin et al., 2009, Blood, 114 (23): 4792-4803, which is incorporated by reference herein in its entirety.

In certain embodiments, a CNI-resistant cell (e.g., a CNI-resistant pluripotent stem cell, a CNI-resistant hematopoietic cell or precursor cell thereof) of the present disclosure is modified to express a variant of calcineurin. In certain embodiments, the calcineurin variant is selected from the group consisting of CNa12 (SEQ ID NO:3; GenBank: GQ463594.1), CNa22 (SEQ ID NO: 4; GenBank: GQ463595.1), and CNb30 (SEQ ID NO:5; GenBank: GQ463597.1).

A target of calcineurin, and thus calcineurin inhibitors, is the transcription factor NFAT, which is activated downstream of CD28 and is required for Treg development. In some embodiments, a CNI resistant may be achieved by gene editing of one or more endogenously expressed NFAT genes. Accordingly, the present disclosure provides a gene edited CNI-resistant cell (e.g., a gene edited steroid-resistant Treg). In some embodiments, a cell is genetically edited to disrupt the expression of one or more NFAT genes, wherein the disruption results in a reduction, deletion, elimination, knockout or disruption in expression of one or more endogenously expressed genes, thereby conferring CNI resistance to the cell.

In some embodiments, a CNI-resistant cell (e.g., a CNI-resistant pluripotent stem cell, a CNI-resistant hematopoietic cell or precursor cell thereof) of the present disclosure is genetically edited to disrupt the expression of one or more NFAT genes. The NFAT transcription factor family comprises five members: NFATc1, NFATc2, NFATc3, NFATc4, and NFAT5. NFATs c1-c4 are regulated by calcium signaling, and are known as the classical members of the NFAT family. Activated calcineurin rapidly dephosphorylates the serine-rich region and SP-repeats in the amino termini of NFAT proteins, resulting in a conformational change that exposes a nuclear localization signal, resulting in NFAT nuclear import. In some embodiments, a CNI-resistant cell of the present disclosure is genetically edited to disrupt one or more endogenously expressed genes selected from the group consisting of NFATc1, NFATc2, NFATc3, NFATc4, and NFAT5. In certain embodiments, a CNI-resistant cell of the present disclosure is genetically edited to disrupt one or more endogenously expressed genes selected from the group consisting of NFATc1, NFATc2, and NFATc4.

In some embodiments, a CNI-resistant cell (e.g., a CNI-resistant pluripotent stem cell, a CNI-resistant hematopoietic cell or precursor cell thereof) of the present disclosure is modified to express an NFAT inhibitor that blocks activity of all NFAT isoforms. In some embodiments, a CNI-resistant cell is modified to express an NFAT inhibitor comprising the VIVIT peptide (SEQ ID NO: 6). Various VIVIT peptide containing agents capable of inhibiting NFAT activity are known in the art. In some embodiments, for example, the VIVIT peptide containing agent is an inhibitor of calcineurin-mediated NFAT activation comprising the sequence set forth in SEQ ID NO: 67 (available at tocris.com/products/nfat-inhibitor_3930 on the World Wide Web).

In some embodiments, a CNI-resistant cell (e.g., a CNI-resistant pluripotent stem cell, a CNI-resistant hematopoietic cell or precursor cell thereof) of the present disclosure exhibits increased cell survival in the presence of a CNI (e.g., CsA). In some embodiments, a CNI-resistant cell is modified to express a calcineurin inhibitor resistance gene and the CNI-resistant cell exhibits increased cell survival in the presence of a CNI. In some embodiments, a CNI-resistant cell of the present disclosure exhibits increased cell survival in the presence of a CNI selected from the group consisting of cyclosporin, voclosporin, pimecrolimus, and tacrolimus, and derivatives and analogs thereof. In certain embodiments, a CNI-resistant cell modified to express a calcineurin inhibitor resistance gene exhibits increased cell survival in the presence of CsA and/or tacrolimus (FK506), and derivatives and analogs thereof. In some embodiments, the increase in cell survival is at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 205%, at least 210%, at least 215%, at least 220%, at least 225%, at least 230%, at least 235%, at least 240%, at least 245%, at least 250%, at least 255%, at least 260%, at least 265%, at least 270%, at least 275%, at least 280%, at least 285%, at least 290%, at least 295%, at least 300%, at least 350%, at least 400%, or more.

Glucocorticoid and Calcineurin Inhibitor-Resistant Cells

As described herein, glucocorticoid resistance can be achieved by disrupting the endogenously expressed NR3C1 gene. Calcineurin inhibitor resistance can be achieved by introducing into the cell a calcineurin inhibitor resistance gene (e.g., a variant of calcineurin).

The present disclosure provides glucocorticoid and calcineurin inhibitor-resistant cells (e.g., a glucocorticoid and calcineurin inhibitor-resistant pluripotent stem cell, a glucocorticoid and calcineurin inhibitor-resistant hematopoietic cell or precursor cell thereof). Such cells are modified to disrupt expression of NR3C1 (e.g., via introduction of indels and/or substitution(s) into the NR3C1 locus (to include regulatory regions, exon(s), and intron(s)), as well as to express a CNI resistance gene. In some embodiments, a glucocorticoid and CNI-resistant cell of the present disclosure is a cell modified to disrupt NR3C1 expression, and further modified to express a CNI resistance gene (e.g., a calcineurin variant). In some embodiments, the CNI resistance gene may be integrated into the genome of the cell via targeted or random integration. Various methods of targeted and random integration are known in the art and described herein. In certain embodiments, the CNI resistance gene is integrated into the genome of the cell into a targeted site within the NR3C1 locus. In some embodiments, the CNI resistance gene is integrated into the genome of the cell outside of the NR3C1 locus. Where the CNI resistance gene is integrated into the genome of the cell outside of the NR3C1 locus, it may be desired to choose an introduction method that does not integrate the CNI resistance gene into a coding region of the genome (e.g., the CNI resistance gene may be desired to integrate into a non-coding region of the genome).

In certain embodiments, a glucocorticoid and CNI-resistant cell (e.g., a glucocorticoid and calcineurin inhibitor-resistant pluripotent stem cell, a glucocorticoid and calcineurin inhibitor-resistant hematopoietic cell or precursor cell thereof) of the present disclosure is a cell modified to disrupt NR3C1 expression (e.g., via introduction of indels and/or substitution(s) into the NR3C1 locus (to include regulatory regions, exon(s), and intron(s)), and further modified to express a CNI resistance gene (e.g., a calcineurin variant) within the NR3C1 locus. Such cells are rendered resistant to glucocorticoids (e.g., dexamethasone) and calcineurin inhibitors (e.g., CsA and/or FK506). In some embodiments, a glucocorticoid and CNI-resistant cell modified to disrupt expression of NR3C1 and to express a CNI resistance gene (e.g., a calcineurin variant) exhibits increased cell survival in the presence of glucorticoids and calcineurin inhibitors, and derivatives and analogs thereof. In some embodiments, the increase in cell survival in the presence of a glucocorticoid (e.g., dexamethasone) or a derivative and analog thereof, is at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 205%, at least 210%, at least 215%, at least 220%, at least 225%, at least 230%, at least 235%, at least 240%, at least 245%, at least 250%, at least 255%, at least 260%, at least 265%, at least 270%, at least 275%, at least 280%, at least 285%, at least 290%, at least 295%, at least 300%, at least 350%, at least 400%, or more. In some embodiments, the increase in cell survival in the presence of a CNI (e.g., FK506, CsA) or a derivative and analog thereof, is at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 205%, at least 210%, at least 215%, at least 220%, at least 225%, at least 230%, at least 235%, at least 240%, at least 245%, at least 250%, at least 255%, at least 260%, at least 265%, at least 270%, at least 275%, at least 280%, at least 285%, at least 290%, at least 295%, at least 300%, at least 350%, at least 400%, or more.

Other Immunosuppressor Drug-Resistant Cells

Other immunosuppressor drugs may be used during treatment and management of GVHD in afflicted subjects. Like glucocorticoids and CNIs, these immunosuppressor drugs may also reduce Treg persistence and function.

For example, sirolimus (rapamycin), everolimus, and analogs and derivatives thereof (also known as rapalogs) belong to the rapamycin family and may be used in immunosuppressive therapy for, e.g., solid organ transplantation and hematopoietic stem cell transplantation. These rapamycin family immunosuppressants inhibit the mammalian target of rapamycin (mTOR) by associating with intracellular receptor FKBP12. The FKBP12-rapamycin complex binds directly to the FKBP12-Rapamycin Binding (FRB) domain of mTOR, inhibiting its activity. In some embodiments, an immunosuppresor drug-resistant cell of the present disclosure is resistant to mTOR inhibition (e.g., an mTOR inhibitor-resistant Treg). mTOR inhibitor-resistant cells of the present disclosure may include, without limitation, cells modified to prevent the formation of the FKBP12-rapamycin complex (e.g., specific mutations in FKBP12), and cells modified to prevent the binding of the FKBP12-rapamycin complex to the FRB domain (e.g., specific mutations in the FRB domain). As the mTOR pathway is a well-studied biological pathway, various methods of achieving resistance to mTOR inhibition are known to those of skill in the art.

Another example of an immunosuppressor drug is mycophenolic acid (also known as mycophenolate). Mycophenolic acid is a potent, reversible, non-competitive inhibitor of Inosine-5'-monophosphate dehydrogenase (IMPDH), an enzyme essential to the de novo synthesis of guanosine-5'-monophosphate (GMP) from inosine-5'-monophosphate (IMP). Another immunosuppressor drug is methotrexate (formerly known as amethopterin). Methotrexate is an antimetabolite of the antifolate type, and can inhibit dihydrofolate reductase (DHFR), an enzyme that participates in the tetrahydrofolate synthesis. Accordingly, in some embodiments, an immunosuppresor drug-resistant cell of the present disclosure is resistant to mycophenolic acid and/or methotrexate, and analogs and derivatives thereof (e.g., a mycophenolic acid and/or methotrexate-resistant Treg). A mycophenolic acid and/or methotrexate-resistant cell of the present disclosure may include, for example, cells modified to express a variant of human DHFR containing the substitutions L22F and F31S, and/or to express a variant of inosine monophosphate dehydrogenase II (IMPDH2) containing the substitutions T3331 and S351Y.

Other examples of immunosuppressor drugs include without limitation, fludarabine, pentostatin (deoxycoformycin), and cyclophosphamide (cytophosphane). Fludarabine is a purine analog and inhibits DNA synthesis by interfering with ribonucleotide reductase and DNA polymerase. Pentostatin is a purine analog and mimics the nucleoside adenosine and inhibits adenosine deaminase, interfering with the cell's ability to process DNA. Cyclophosphamide is converted by mixed-function oxidase enzymes (e.g., of the cytochrome P450 system) into active metabolites, including without limitation, 4-hydroxycyclophosphamide, and phosphoramide mustard. Phosphoramide mustard forms DNA crosslinks both between and within DNA strands at guanine N-7 positions (known as interstrand and intrastrand crosslinkages, respectively). Mechanisms of resistance to these drugs are known in the art and can be used to produce immunosuppressor drug-resistant cells of the present disclosure, e.g., modified cells (e.g., modified hematopoietic cells or precursor cells thereof) that are resistant to fludarabine, pentostatin, and/or cyclophosphamide.

C. Methods of Producing Modified Cells

Cells of the present invention are genetically edited to disrupt the expression of any of the endogenous genes described herein. Accordingly, in some embodiments, a modified cell (e.g., a modified cell comprising a calcineurin inhibitor resistance gene) of the present invention is genetically edited to disrupt the expression of one or more of the endogenous genes described herein.

Various gene editing technologies are known to those skilled in the art. Gene editing technologies include, without limitation, homing endonucleases, zinc-finger nucleases (ZFNs), transcription activator-like effector (TALE) nucleases (TALENs), clustered regularly interspaced short palindromic repeats (CRISPR)-CRISPR-associated protein 9 (Cas9) genome editing systems, and CRISPR-Cpf1 genome editing systems. Homing endonucleases generally cleave their DNA substrates as dimers, and do not have distinct binding and cleavage domains. ZFNs recognize target sites that consist of two zinc-finger binding sites that flank a 5- to 7-base pair (bp) spacer sequence recognized by the FokI cleavage domain. TALENs recognize target sites that consist of two TALE DNA-binding sites that flank a 12- to 20-bp spacer sequence recognized by the FokI cleavage domain. The Cas9 nuclease is targeted to DNA sequences complementary to the targeting sequence within the single guide RNA (gRNA) located immediately upstream of a compatible protospacer adjacent motif (PAM) that may exist on either strand of the DNA helix. Accordingly, one of skill in the art would be able to select the appropriate gene editing technology for the present invention.

In some aspects, the disruption is carried out by gene editing using an RNA-guided nuclease such as a CRISPR-Cas system, such as CRISPR-Cas9 system or CRISPR-Cpf1 system specific for the gene (e.g., NR3C1) that is disrupted. In some embodiments, an agent comprising Cas9 and a guide RNA (gRNA) comprising a targeting domain, which targets a region of the genetic locus, is introduced into the cell. In some embodiments, the agent is or comprises a ribonucleoprotein (RNP) complex of a Cas9 polypeptide and a gRNA (Cas9/gRNA RNP). In some embodiments, the introduction includes contacting the agent or portion thereof with the cells, in vitro, which can include cultivating or incubating the cell and agent for up to 24, 36 or 48 hours or 3, 4, 5, 6, 7, or 8 days. In some embodiments, the introduction further can include effecting delivery of the agent into the cells. In various embodiments, the methods, compositions and cells according to the present disclosure utilize direct delivery of ribonucleoprotein (RNP) complexes of Cas9 and gRNA to cells, for example by electroporation. In some embodiments, the RNP complexes include a gRNA that has been modified to include a 3' poly-A tail and a 5' Anti-Reverse Cap Analog (ARCA) cap.

The CRISPR/Cas9 system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/Cas9 system can thereby be engineered to cleave virtually any DNA sequence by redesigning the gRNA cells. The CRISPR/Cas9 system can simultaneously target multiple genomic loci by co-expressing a single Cas9 protein with two or more gRNAs, making this system suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNH, and RuvC. The REC I domain binds the guide RNA, while the Bridge helix binds to target DNA. The HNH and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence. A PAM is a two or three nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HNH nuclease domains cut the target DNA after the third nucleotide base upstream of the PAM.

One non-limiting example of a CRISPR/Cas system used to inhibit gene expression, CRISPR interference (CRISPRi), is described in U.S. Patent Appl. Publ. No. US20140068797. CRISPRi utilizes a catalytically dead Cas9 which lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, a pAd5F35-CRISPR vector. In other embodiments, the Cas expression vector induces expression of Cas9 endonuclease. Other endonucleases may also be used, including but not limited to, Cas12a (Cpf1), T7, Cas3, Cas8a, Cas8b, Cas10d, Cse1, Csy1, Csn2, Cas4, Cas10, Csm2, Cmr5, Fok1, other nucleases known in the art, and any combinations thereof.

In certain embodiments, the CRISPR/Cas system may comprise a variant of Cas9 with altered activity. Exemplary variant Cas9 nucleases include, but are not limited to, a Cas9 nickase (nCas9), a catalytically dead Cas9 (dCas9), a hyper accurate Cas9 (HypaCas9) (Chen et al. Nature, 550 (7676), 407-410 (2017)), a high fidelity Cas9 (Cas9-HF) (Kleinstiver et al. Nature 529 (7587), 490-495 (2016)), an enhanced specificity Cas9 (eCas9) (Slaymaker et al. Science 351 (6268), 84-88 (2016)), and an expanded PAM Cas9 (xCas9) (Hu et al. Nature doi: 10.1038/nature26155 (2018)).

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). Other inducible promoters known by those of skill in the art can also be used. The inducing agent can be a selective condition (e.g., exposure to an agent, for example an antibiotic) that results in induction of the inducible promoter. This results in expression of the Cas expression vector.

As used herein, the term "guide RNA" or "gRNA" refer to any nucleic acid that promotes the specific association (or "targeting") of an RNA-guided nuclease such as a Cas9 to a target sequence (e.g., a genomic or episomal sequence) in a cell. It will be understood by those of skill in the art that gRNA sequences may be recited with a uracil or "U" nucleotide in place of a thymine or "T" nucleotide.

As used herein, a "modular" or "dual RNA" guide comprises more than one, and typically two, separate RNA molecules, such as a CRISPR RNA (crRNA) and a trans-activating crRNA (tracrRNA), which are usually associated with one another, for example by duplexing. gRNAs and their component parts are described throughout the literature (see, e.g., Briner et al. Mol. Cell, 56 (2), 333-339 (2014), which is incorporated by reference).

As used herein, a "unimolecular gRNA," "chimeric gRNA," or "single guide RNA (sgRNA)" comprises a single RNA molecule. The sgRNA may be a crRNA and tracrRNA linked together. For example, the 3' end of the crRNA may be linked to the 5' end of the tracrRNA. A crRNA and a tracrRNA may be joined into a single unimolecular or chimeric gRNA, for example, by means of a four nucleotide (e.g., GAAA) "tetraloop" or "linker" sequence bridging complementary regions of the crRNA (at its 3' end) and the tracrRNA (at its 5' end).

As used herein, a "repeat" sequence or region is a nucleotide sequence at or near the 3' end of the crRNA which is complementary to an anti-repeat sequence of a tracrRNA.

As used herein, an "anti-repeat" sequence or region is a nucleotide sequence at or near the 5' end of the tracrRNA which is complementary to the repeat sequence of a crRNA.

Additional details regarding guide RNA structure and function, including the gRNA/Cas9 complex for genome editing may be found in, at least, Mali et al. Science, 339 (6121), 823-826 (2013); Jiang et al. Nat. Biotechnol. 31 (3). 233-239 (2013); and Jinek et al. Science, 337 (6096), 816-821 (2012); which are incorporated by reference herein.

As used herein, a "guide sequence" or "targeting sequence" refers to the nucleotide sequence of a gRNA, whether unimolecular or modular, that is fully or partially complementary to a target domain or target polynucleotide within a DNA sequence in the genome of a cell where editing is desired. Guide sequences are typically 10-30 nucleotides in length, preferably 16-24 nucleotides in length (for example, 16, 17, 18, 19, 20, 21, 22, 23 or 24 nucleotides in length), and are at or near the 5' terminus of a Cas9 gRNA.

As used herein, a "target domain" or "target polynucleotide sequence" or "target sequence" is the DNA sequence in a genome of a cell that is complementary to the guide sequence of the gRNA.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of a CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell (e.g., pluripotent stem cell), such that expression of the elements of the CRISPR system direct formation of a CRISPR complex at one or more target sites. For example, a Cas nuclease, a crRNA, and a tracrRNA could each be operably linked to separate regulatory elements on separate vectors. As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter).

Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in U.S. Patent Appl. Publ. No. US20110059502, incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells (e.g., human pluripotent stem cells) or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In some embodiments, the CRISPR/Cas is derived from a type II CRISPR/Cas system. In other embodiments, the CRISPR/Cas system is derived from a Cas9 nuclease. Exemplary Cas9 nucleases that may be used in the present invention include, but are not limited to, *S. pyogenes* Cas9 (SpCas9), *S. aureus* Cas9 (SaCas9), *S. thermophilus* Cas9 (StCas9), *N. meningitidis* Cas9 (NmCas9), *C. jejuni* Cas9 (CjCas9), and *Geobacillus* Cas9 (GeoCas9).

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

As used herein, a "base editor" is a protein or fusion protein that comprises a CRISPR deactivated or nicking DNA binding domain that is capable of binding a guide RNA, which in turn binds a target nucleic acid sequence via strand hybridization, and further comprises a base-editing domain capable of editing a base of the target nucleic acid sequence. In certain embodiments, the CRISPR system comprises a base editor and a guide RNA.

The term "base editor" encompasses "next generation" base editors such as third-generation base editors (BE3 systems), fourth-generation base editors (BE4 systems), and adenine base editors. Third-generation base editors (BE3 systems), in which base excision repair inhibitor UGI is fused to the Cas9 nickase, nick the unmodified DNA strand so that the cell is encouraged to use the edited strand as a template for mismatch repair. As a result, the cell repairs the DNA using a U-containing strand (introduced by cytidine deamination) as a template, copying the base edit. Fourth generation base editors (BE4 systems) employ two copies of base excision repair inhibitor UGI. Adenine base editors (ABEs) have been developed that efficiently convert targeted A•T base pairs to G•C (0-100% efficiency in human cells) in genomic DNA with high product purity (typically at least 99.9%) and low rates of indels (typically no more than 0.1%). See, for example, Gaudelli et al., Nature 551:464-471 (2017). It will be understood that other base editors, including those that introduce null mutations at ATG "start" codons to disrupt expression of the targeted gene, are suitable for use according to the methods described herein.

The base editor may comprise any suitable CRISPR deactivated or nicking DNA binding domain that can bind a guide RNA. In some embodiments, the CRISPR deactivated or nicking DNA binding domain is a Cas9 nuclease that has one of two DNA cleavage domains inactivated, i.e., the Cas9 is a nickase. A nuclease-inactivated Cas9 protein may be referred to as a "dCas9" protein (for nuclease-"dead" Cas9). Methods for generating a Cas9 protein (or a fragment thereof) having an inactive DNA cleavage domain are known (See, e.g., Jinek et al., Science. 337:816-821 (2012); Qi et al., "Repurposing CRISPR as an RNA-Guided Platform for Sequence-Specific Control of Gene Expression" (2013) Cell. 28; 152 (5): 1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of S. pyogenes Cas9 (Jinek et al., Science. 337:816-821 (2012); Qi et al., Cell. 28; 152 (5): 1173-83 (2013)). Suitable CRISPR deactivated or nicking DNA binding domains include, without limitation, nuclease-inactive variant Cas9 domains that include D10A, D10A/D839A/H840A, and D10A/D839A/H840A/N863A mutant domains as described in WO2015089406A1 which is incorporated herein by reference.

Once introduced to a target cell or genome, the CRISPR deactivated or nicking DNA binding domain (e.g., nuclease-inactivated Cas9) searches for target DNA by binding to sequences that match its protospacer adjacent motif (PAM) sequence. In some embodiments, the CRISPR deactivated or nicking DNA binding domain may recognize a non-canonical PAM sequence (e.g., a non-NGG PAM sequence). Such PAM sequences are known in the art, including, for example, without limitation: 5'-NGA-3'; 5'-NGCG-3'; 5'-NGAG-3'; 5'-NNGRRT-3'; and 5'-NNNRRT-3'. The skilled person armed with knowledge in the art would be able to determine the appropriate PAM sequence that is recognized by a given CRISPR nuclease.

The term "base-editing domain" refers to an agent comprising a polypeptide that is capable of making a modification to a base (e.g., A, T, C, G, or U) within a nucleic acid sequence (e.g., DNA or RNA) (e.g., a base substitution). In some embodiments, the base-editing domain is a DNA-editing domain. In some embodiments, the base-editing domain is capable of deaminating a base within a nucleic acid. In some embodiments, the base editor is capable of deaminating a base within a DNA molecule. In some embodiments, the base-editing domain is a deaminase domain.

In some embodiments, the deaminase is an adenosine deaminase. In some embodiments, the adenosine deaminases are capable of deaminating adenine. In some embodiments, the adenosine deaminases are capable of deaminating adenine in a deoxyadenosine residue of DNA. The adenosine deaminase may be derived from any suitable organism (e.g., E. coli). In some embodiments, the adenine deaminase is a naturally-occurring adenosine deaminase that includes one or more mutations corresponding to any of the mutations provided herein (e.g., mutations in ecTadA). In some embodiments, the adenosine deaminase is from a prokaryote. In some embodiments, the adenosine deaminase is from a bacterium. In some embodiments, the adenosine deaminase is from *Escherichia coli, Staphylococcus aureus, Salmonella typhi, Shewanella putrefaciens, Haemophilus influenzae, Caulobacter crescentus*, or *Bacillus subtilis*. In some embodiments, the adenosine deaminase is from *E. coli*. In some embodiments the deaminase is rationally engineered and/or evolved to acquire or enhance activity.

In certain exemplary embodiments, the deaminase is a cytidine deaminase. In some embodiments, the deaminase is an apolipoprotein B mRNA-editing complex (APOBEC) family deaminase. In some embodiments, the deaminase is an APOBEC1 family deaminase. In some embodiments, the deaminase is an activation-induced cytidine deaminase (AID). In some embodiments, the deaminase is an ACF1/ASE deaminase. In some embodiments, the deaminase is an adenosine deaminase. In some embodiments, the deaminase is an ADAT family deaminase. In some embodiments, the base-editing domain is fused to the N-terminus of the Cas9 domain. In some embodiments, the base-editing domain is fused to the C-terminus of the Cas9 domain. In some embodiments, the Cas9 domain and the base-editing domain are fused via a linker.

Various CRISPR deactivated or nicking DNA binding domains and base-editing domains of base editor proteins are described in U.S. Patent Publication Nos. US20150166985A1, US20150166980A1, US20150166984A1, US20170121693A1, and US20180073012A1; and U.S. Pat. Nos. 9,068,179 and 9,840,699, all of which are incorporated herein by reference.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4th Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

In some embodiments, guide RNA(s) and Cas9 or a base editor can be delivered to a cell as a ribonucleoprotein (RNP) complex (e.g., a Cas9/RNA-protein complex). RNPs are comprised of purified Cas9 protein or purified base editor complexed with gRNA and are well known in the art to be efficiently delivered to multiple types of cells, including but not limited to stem cells and immune cells (Addgene, Cambridge, MA, Mirus Bio LLC, Madison, WI). In some embodiments, the Cas9 or base editor/RNA-protein complex is delivered into a cell by electroporation.

In some embodiments, a gene edited cell of the present disclosure is edited using CRISPR/Cas9 to disrupt one or more endogenous genes in a cell (e.g., a Treg). In some embodiments, CRISPR/Cas9 is used to disrupt endogenous NR3C1, thereby resulting in the downregulation of NR3C1 expression. In some embodiments, a gene edited cell of the present disclosure is base edited (e.g., a substitution is introduced into the cell) using a base editor to disrupt one or more endogenous genes in a cell (e.g., a Treg). In some embodiments, the base editor is used to disrupt endogenous NR3C1, thereby resulting in the downregulation of NR3C1 expression.

As described herein, downregulation of NR3C1 results in resistance to steroids, e.g., glucocorticoids. Accordingly, in some embodiments, the present disclosure provides a steroid-resistant cell (e.g., a glucocorticoid-resistant Treg), wherein CRISPR/Cas9 is used to disrupt endogenous NR3C1, thereby resulting in the downregulation of NR3C1 expression. Accordingly, a steroid-resistant CRISPR-modified cell of the present disclosure comprises a CRISPR-mediated insertion(s) and/or deletion(s) (indel(s)) in a gene locus encoding for NR3C1, wherein the indel is capable of downregulating gene expression of NR3C1. Accordingly, a steroid-resistant CRISPR-modified cell of the present disclosure comprises a base edit (e.g., targeted base substitution) in a gene locus encoding for NR3C1, wherein the base edit is capable of ablation/downregulating gene expression of NR3C1.

According to NCBI Reference Sequence: NM_001018074.1, the NR3C1 locus contains 9 exons. In some embodiments, the CRISPR-mediated indel in a gene locus encoding for NR3C1 is located in exon 1, exon 2, exon 3, exon 4, exon 5, exon 6, exon 7, exon 8, or exon 9 of NR3C1. As such, in some embodiments, the gRNA comprises a guide sequence that is sufficiently complementary with a target sequence within exon 1, exon 2, exon 3, exon 4, exon 5, exon 6, exon 7, exon 8, or exon 9 of NR3C1. In certain embodiments, the indel in a gene locus encoding for NR3C1 is located in exon 2 of NR3C1. In certain embodiments, the guide RNA comprises a guide sequence that is sufficiently complementary with a target sequence in exon 2 of NR3C1. Suitable gRNAs for use in disrupting endogenous NR3C1 is set forth in Table 1. In certain embodiments, the guide sequence is sufficiently complementary to the target sequence in the NR3C1 gene and comprises a nucleic acid sequence set forth in any one of SEQ ID NOs: 7-10.

TABLE 1

| gRNA name | gRNA sequence | SEQ ID NO: |
|---|---|---|
| GR1 | AACCAAAAGTCTTCGCTGCT (anti-sense) | 7 |
| GR2 | TTGAGAAGCGACAGCCAGTG (anti-sense) | 8 |
| GR3 | ACCAGGAGTTAATGATTCTT (anti-sense) | 9 |
| GR4 | TCCTGAGCAAGCACACTGCT (anti-sense) | 10 |

In some embodiments, the *S. pyogenes* CRISPR/Cas9 base editor-mediated substitution in a gene locus encoding for NR3C1 introduces a premature stop codon. As such, in some embodiments, the gRNA comprises a guide sequence that is sufficiently complementary with a target sequence within which one or more base pair substitutions will convert the normal wild-type codon into a stop codon. In certain embodiments, the substitution in a gene locus encoding for NR3C1 is located in an exon of NR3C1. In certain embodiments, the guide RNA comprises a guide sequence that is sufficiently complementary with a target sequence in an exon of NR3C1. Suitable gRNAs for use in mediating a substitution that leads to the introduction of a premature stop codon in endogenous NR3C1 is set forth in Table 2. In certain embodiments, the guide sequence is sufficiently complementary to the target sequence in the NR3C1 gene and comprises a nucleic acid sequence set forth in any one of SEQ ID NOs: 17-54.

TABLE 2

| gRNA name | gRNA sequence* | SEQ ID NO: |
|---|---|---|
| BE1 | UGCUcAGGAGAGGGGAGAUG | 17 |
| BE2 | CUUGCUcAGGAGAGGGGAGA | 18 |
| BE3 | UUCUcAAUCAGACUCCAAGC | 19 |
| BE4 | GGGCcAAAUCAGCCUUUCCU | 20 |
| BE5 | UCAGAAcAGCAACAUUUGAA | 21 |
| BE6 | AAGGGCcAGACUGGCACCAA | 22 |
| BE7 | CCCcAAGUGAAAACAGAAAA | 23 |
| BE8 | UACUGUcAGGCAAGCUUUCC | 24 |
| BE9 | ACUGUcAGGCAAGCUUUCCU | 25 |
| BE10 | GGAGGAcAGAUGUACCACUA | 26 |
| BE11 | CCUUUCUcAACAGCAGGAUC | 27 |
| BE12 | AUUcCAAUUUUCGGAACCAA | 28 |
| BE13 | UUCcAAUUUUCGGAACCAAC | 29 |
| BE14 | AGGUGCcAAGGAUCUGGAGA | 30 |
| BE15 | GGUcGAACAGUUUUUUCUAA | 31 |
| BE16 | UAUcGAAAAUGUCUUCAGGC | 32 |
| BE17 | UCUUcAGGCUGGAAUGAACC | 33 |
| BE18 | CUUcAGGCUGGAAUGAACCU | 34 |
| BE19 | ACAGCUcGAAAAACAAAGAA | 35 |

TABLE 2-continued

| gRNA name | gRNA sequence* | SEQ ID NO: |
|---|---|---|
| BE20 | GGAAUUcAGCAGGCCACUAC | 36 |
| BE21 | GAAUUcAGCAGGCCACUACA | 37 |
| BE22 | ACCAcAACUCACCCCUACCC | 38 |
| BE23 | UUACCAcAACUCACCCCUAC | 39 |
| BE24 | UGAUCCUcCAAGUUGAGUCU | 40 |
| BE25 | CUCcAAGUUGAGUCUGGAAC | 41 |
| BE26 | GGAUGACcAAAUGACCCUAC | 42 |
| BE27 | ACAUCcAGGAGUACUGCAGU | 43 |
| BE28 | AACAUCcAGGAGUACUGCAG | 44 |
| BE29 | AGGCUUcAGGUAUCUUAUGA | 45 |
| BE30 | CAGGCUUcAGGUAUCUUAUG | 46 |
| BE31 | AAGAGCcAAGAGCUAUUUGA | 47 |
| BE32 | UUAUcAACUGACAAAACUCU | 48 |
| BE33 | UAUcAACUGACAAAACUCUU | 49 |
| BE34 | UUUAUcAACUGACAAAACUC | 50 |
| BE35 | CUUCcAAACAUUUUGGAUA | 51 |
| BE36 | CCAAUcAGAUACCAAAAUAU | 52 |
| BE37 | AACcACAUAACAUUCUAUAA | 53 |
| BE38 | GUUUCAUcAAAAGUGACUGC | 54 |

*lower case residue denotes site of deamination (substitution).

In some embodiments, the CRISPR-mediated substitution in a gene locus encoding for NR3C1 is located in a splice acceptor or a splice donor of NR3C1. As such, in some embodiments, the gRNA comprises a guide sequence that is sufficiently complementary with a target sequence comprising a splice acceptor or a splice donor of NR3C1. In certain embodiments, the substitution in a gene locus encoding for NR3C1 is located at or near a splice acceptor or a splice donor of NR3C1, wherein the substitution is capable of disrupting the normal splicing of NR3C1, thereby downregulating/ablating the expression of NR3C1. In certain embodiments, the guide RNA comprises a guide sequence that is sufficiently complementary with a target sequence comprising a splice acceptor of NR3C1. In certain embodiments, the guide RNA comprises a guide sequence that is sufficiently complementary with a target sequence comprising a splice donor of NR3C1. Suitable gRNAs for use in mediating a substitution at or near a splice acceptor or a splice donor of NR3C1 is set forth in Table 3. In certain embodiments, the guide sequence is sufficiently complementary to the target sequence in the NR3C1 gene and comprises a nucleic acid sequence set forth in any one of SEQ ID NOs: 55-56.

TABLE 3

| gRNA name | gRNA sequence* | SEQ ID NO: |
|---|---|---|
| BE-SA1 | GCUGUCcUaUaUggaaUaaa (anti-sense) | 55 |

TABLE 3-continued

| gRNA name | gRNA sequence* | SEQ ID NO: |
|---|---|---|
| BE-SD1 | UacUCAUUAAUAAUCAGAUC (anti-sense) | 56 |

*lower case residue denotes site of deamination (substitution).

Accordingly, a method for generating a steroid-resistant modified cell (e.g., modified pluripotent stem cell, modified Treg) of the present disclosure comprises introducing into a cell a CRISPR system that produces an indel in exon 2 of NR3C1, wherein the indel is capable of downregulating gene expression of NR3C1. In some embodiments, a method for generating a steroid-resistant modified cell (e.g., modified pluripotent stem cell, modified Treg) of the present disclosure comprises introducing into a cell a CRISPR system that produces an indel in exon 2 of NR3C1, wherein the indel is capable of downregulating gene expression of NR3C1, wherein the CRISPR system comprises a guide RNA comprising the nucleic acid sequence set forth in SEQ ID NO:7. In some embodiments, a method for generating a steroid-resistant modified cell (e.g., modified pluripotent stem cell, modified Treg) of the present disclosure comprises introducing into a cell a CRISPR system that produces an indel in exon 2 of NR3C1, wherein the indel is capable of downregulating gene expression of NR3C1, wherein the CRISPR system comprises a guide RNA comprising the nucleic acid sequence set forth in SEQ ID NO:8. In some embodiments, a method for generating a steroid-resistant modified cell (e.g., modified pluripotent stem cell, modified Treg) of the present disclosure comprises introducing into a cell a CRISPR system that produces an indel in exon 2 of NR3C1, wherein the indel is capable of downregulating gene expression of NR3C1, wherein the CRISPR system comprises a guide RNA comprising the nucleic acid sequence set forth in SEQ ID NO:9. In some embodiments, a method for generating a steroid-resistant modified cell (e.g., modified pluripotent stem cell, modified Treg) of the present disclosure comprises introducing into a cell a CRISPR system that produces an indel in exon 2 of NR3C1, wherein the indel is capable of downregulating gene expression of NR3C1, wherein the CRISPR system comprises a guide RNA comprising the nucleic acid sequence set forth in SEQ ID NO:10.

Accordingly, a method for generating a steroid-resistant modified cell (e.g., modified pluripotent stem cell, modified Treg) of the present disclosure comprises introducing into a cell a CRISPR system that produces a substitution in an exon of NR3C1, wherein the substitution is capable of downregulating gene expression of NR3C1. In some embodiments, a method for generating a steroid-resistant modified cell (e.g., modified pluripotent stem cell, modified Treg) of the present disclosure comprises introducing into a cell a CRISPR system that produces a substitution an exon of NR3C1, wherein the substitution is capable of downregulating gene expression of NR3C1, wherein the CRISPR system comprises a guide RNA comprising the nucleic acid sequence set forth in any one of SEQ ID NOs: 17-54. In some embodiments, a method for generating a steroid-resistant modified cell (e.g., Treg) of the present disclosure comprises introducing into the cell a CRISPR system that produces a substitution in an exon of NR3C1, wherein the substitution is capable of downregulating gene expression of NR3C1, wherein the CRISPR system comprises a guide RNA comprising the nucleic acid sequence set forth in SEQ ID NOs:

20 or 21. In some embodiments, a method for generating a steroid-resistant modified cell (e.g., Treg) of the present disclosure comprises introducing into the cell a CRISPR system that produces a substitution in an exon of NR3C1, wherein the substitution is capable of downregulating gene expression of NR3C1, wherein the CRISPR system comprises a guide RNA comprising the nucleic acid sequence set forth in SEQ ID NO:20. In some embodiments, a method for generating a steroid-resistant modified cell (e.g., Treg) of the present disclosure comprises introducing into the cell a CRISPR system that produces a substitution in an exon of NR3C1, wherein the substitution is capable of downregulating gene expression of NR3C1, wherein the CRISPR system comprises a guide RNA comprising the nucleic acid sequence set forth in SEQ ID NOs: 21.

Accordingly, a method for generating a steroid-resistant modified cell (e.g., modified pluripotent stem cell, modified Treg) of the present disclosure comprises introducing into the cell a CRISPR system that produces a substitution in a splice acceptor, or a splice donor of NR3C1, wherein the substitution is capable of disrupting normal splicing of NR3C1, thereby downregulating gene expression of NR3C1. In some embodiments, a method for generating a steroid-resistant modified cell (e.g., modified pluripotent stem cell, modified Treg) of the present disclosure comprises introducing into the cell a CRISPR system that produces a substitution in a splice acceptor, or a splice donor of NR3C1, wherein the substitution is capable of disrupting normal splicing of NR3C1, thereby downregulating gene expression of NR3C1, wherein the CRISPR system comprises a guide RNA comprising the nucleic acid sequence set forth in SEQ ID NO 55 or 56. In some embodiments, a method for generating a steroid-resistant modified cell (e.g., Treg) of the present disclosure comprises introducing into the cell a CRISPR system that produces a substitution in a splice acceptor, or a splice donor of NR3C1, wherein the substitution is capable of disrupting normal splicing of NR3C1, thereby downregulating gene expression of NR3C1, wherein the CRISPR system comprises a guide RNA comprising the nucleic acid sequence set forth in SEQ ID NO: 55. In some embodiments, a method for generating a steroid-resistant modified cell (e.g., Treg) of the present disclosure comprises introducing into the cell a CRISPR system that produces a substitution in a splice acceptor, or a splice donor of NR3C1, wherein the substitution is capable of disrupting normal splicing of NR3C1, thereby downregulating gene expression of NR3C1, wherein the CRISPR system comprises a guide RNA comprising the nucleic acid sequence set forth in SEQ ID NO: 56.

In some embodiments, a method for generating a steroid- and calcineurin inhibitor-resistant modified cell (e.g., Treg) of the present disclosure comprises introducing into the cell a CRISPR system that produces an indel in NR3C1, wherein the indel is capable of downregulating gene expression of NR3C1, and further comprises an insertion of an exogenous calcineurin inhibitor resistance gene into the genome of the cell. In some embodiments, the insertion of the CNI resistance gene occurs at the site of the indel in NR3C1. In some embodiments, the indel in NR3C1 is in exon 2 of NR3C1. In some embodiments, the CNI resistance gene encodes for a calcineurin variant, wherein the calcineurin variant is a mutant form of a calcineurin A (CNa) gene selected from the group consisting of PPP3Ca, PPP3Cb, and PPP3Cc (three isoforms of the catalytic subunit), or a mutant form of a calcineurin B (CNb) gene selected from the group consisting of PPP3R1 and PPP3R2 (two isoforms of the regulatory subunit). In some embodiments, the calcineurin variant is selected from the group consisting of CNa12 (SEQ ID NO:3), CNa22 (SEQ ID NO:4), and CNb30 (SEQ ID NOs: 5).

In some embodiments, a method for generating a steroid- and calcineurin inhibitor-resistant modified cell (e.g., Treg) of the present disclosure comprises introducing into the cell a CRISPR system that produces a substitution in NR3C1, wherein the substitution is capable of downregulating gene expression of NR3C1, and further comprises an insertion of an exogenous calcineurin inhibitor resistance gene into the genome of the cell. In some embodiments, the substitution in NR3C1 is in an exon of NR3C1. In some embodiments, the substitution in NR3C1 is in exon 2 of NR3C1. In some embodiments, the substitution in NR3C1 is in a splice acceptor of NR3C1. In some embodiments, the substitution in NR3C1 is in a splice donor of NR3C1. In some embodiments, the insertion of the CNI resistance gene occurs at, near, or downstream of the site of the substitution in NR3C1 (e.g., within the NR3C1 locus). In some embodiments, the insertion of the CNI resistance gene occurs outside the NR3C1 locus). In some embodiments, the CNI resistance gene encodes for a calcineurin variant, wherein the calcineurin variant is a mutant form of a calcineurin A (CNa) gene selected from the group consisting of PPP3Ca, PPP3Cb, and PPP3Cc, or a mutant form of a calcineurin B (CNb) gene selected from the group consisting of PPP3R1 and PPP3R2. In some embodiments, the calcineurin variant is selected from the group consisting of CNa12 (SEQ ID NO:3), CNa22 (SEQ ID NO: 4), and CNb30 (SEQ ID NOs: 5).

Accordingly, a method for generating a steroid- and calcineurin inhibitor-resistant modified cell (e.g., Treg) comprises introducing into the cell a CRISPR system that produces an indel in exon 2 of NR3C1, wherein the indel is capable of downregulating gene expression of NR3C1, and further comprises an insertion of an exogenous CNI resistance gene into the site of the indel in NR3C1, wherein the exogenous CNI resistance gene encodes for a calcineurin variant comprising the amino acid sequence set forth in SEQ ID NO:3. Accordingly, a method for generating a steroid- and calcineurin inhibitor-resistant modified cell (e.g., Treg) comprises introducing into the cell a CRISPR system that produces an indel in exon 2 of NR3C1, wherein the indel is capable of downregulating gene expression of NR3C1, and further comprises an insertion of an exogenous CNI resistance gene into the site of the indel in NR3C1, wherein the exogenous CNI resistance gene encodes for a calcineurin variant comprising the amino acid sequence set forth in SEQ ID NO:4. Accordingly, a method for generating a steroid- and calcineurin inhibitor-resistant modified cell (e.g., Treg) comprises introducing into the cell a CRISPR system that produces an indel in exon 2 of NR3C1, wherein the indel is capable of downregulating gene expression of NR3C1, and further comprises an insertion of an exogenous CNI resistance gene into the site of the indel in NR3C1, wherein the exogenous CNI resistance gene encodes for a calcineurin variant comprising the amino acid sequence set forth in SEQ ID NO: 5.

In some cases, the modified cell is a modified pluripotent stem cell, either embryonic or induced. In such cases, the methods provided herein further comprise differentiating modified pluripotent stem cells under conditions that promote differentiation of the modified pluripotent stem cells into hematopoietic precursor cells or hematopoietic cells. In some cases, the method comprises culturing modified pluripotent stem cells in the presence of differentiation factors necessary and sufficient to obtain modified hematopoietic precursors and differentiated hematopoietic cell types. Modified pluripotent stem cells can be then differentiated according to any appropriate differentiation methods, such as those described in, for example, U.S. Pat. Nos. 9,574,179, 8,093,049, thus producing modified pluripotent stem cell-derived hematopoietic cells or precursors thereof.

Accordingly, in some cases, a method for generating a steroid- and/or calcineurin inhibitor-resistant modified cell (e.g., Treg) comprises introducing into a pluripotent stem cell a CRISPR system that produces a substitution in a gene locus encoding for NR3C1 as described herein, wherein the substitution is capable of downregulating gene expression of NR3C1, and, in some cases, further comprises introducing an insertion of an exogenous calcineurin inhibitor resistance gene into the genome of the pluripotent cell.

In some aspects, the provided compositions and methods include those in which at least or greater than about 25%, 30%, 35%, 40%, 45%, 50%, 55%, 60%, 65%, 70%, 75%, 80%, 85%, 90% or 95% of cells in a composition of cells contain the desired genetic modification. For example, about 25%, 30%, 35%, 40%, 45%, 50%, 55%, 60%, 65%, 70%, 75%, 80%, 85%, 90% or 95% of cells in a composition of cells into which an agent (e.g., gRNA/Cas nuclease) for knockout or genetic disruption (e.g., indel and/or substitution) of endogenous gene (e.g., NR3C1) was introduced contain the genetic disruption; do not express the targeted endogenous polypeptide, do not contain a contiguous and/or functional copy of the targeted gene. In some embodiments, the methods, compositions and cells according to the present disclosure include those in which at least or greater than about 25%, 30%, 35%, 40%, 45%, 50%, 55%, 60%, 65%, 70%, 75%, 80%, 85%, 90% or 95% of cells in a composition of cells into which an agent (e.g., gRNA/Cas nuclease) for knockout or genetic disruption (e.g., indel and/or substitution) of a targeted gene was introduced do not express the targeted polypeptide. In some embodiments, at least or greater than about 25%, 30%, 35%, 40%, 45%, 50%, 55%, 60%, 65%, 70%, 75%, 80%, 85%, 90% or 95% of cells in a composition of cells into which an agent (e.g. gRNA/Cas9) for knockout or genetic disruption (e.g., indel and/or substitution) of the targeted gene was introduced are knocked out in both alleles, i.e. comprise a biallelic deletion, in such percentage of cells.

In some embodiments, provided are compositions and methods in which the Cas9-mediated cleavage efficiency (e.g., % indel, % substitution) in or near the targeted gene (e.g. within or about within 100 base pairs, within or about within 50 base pairs, or within or about within 25 base pairs or within or about within 10 base pairs upstream or downstream of the cut site) is at least or greater than about 25%, 30%, 35%, 40%, 45%, 50%, 55%, 60%, 65%, 70%, 75%, 80%, 85%, 90% or 95% in cells of a composition of cells into which an agent (e.g. gRNA/Cas9) for knockout or genetic disruption of a targeted gene has been introduced.

In some embodiments, the provided cells, compositions and methods results in a reduction or disruption of signals delivered via the endogenous in at least or greater than about 25%, 30%, 35%, 40%, 45%, 50%, 55%, 60%, 65%, 70%, 75%, 80%, 85%, 90% or 95% of cells in a composition of cells into which an agent (e.g., gRNA/Cas nuclease) for knockout or genetic disruption of a targeted gene was introduced.

In some embodiments, the cells in the composition retain a phenotype of the cells compared to the phenotype of cells in a corresponding or reference composition when assessed under the same conditions. In some embodiments, the cells in the composition retain a phenotype of the cells compared to the phenotype of cells in a corresponding or reference composition when assessed under the same conditions, except for the effects disrupting the target gene has on the cells.

In some embodiments, cells in the composition include without limitation, naive cells, effector memory cells, central memory cells, stem central memory cells, effector memory cells, and long-lived effector memory cells. In some embodiments, the cells include without limitation, immune suppressive cells, such as regulatory T cells (Tregs), non-Tregs modified to be directly immune suppressive (e.g., via secretion of IL-10 or TGF-β), and non-Tregs modified to be indirectly immune suppressive (e.g., cytotoxic T lymphocytes (CTLs) that kill antigen presenting cells (APCs)). In some embodiments, the cells include without limitation, dendritic cells, myeloid derived suppressor cells, immunoregulatory macrophages, mesenchymal stem cells, multipotent adult progenitor cells, embryonic stem cells, induced pluripotent stem cells, thymic progenitor cells, immune regulatory B cells, immune regulatory NK cells, immune regulatory monocytes, veto cells, innate lymphoid cells, invariant natural killer (NK) T cells. In some embodiments, the cells include hematopoietic cells and precursor cells thereof. In some embodiments, the cells include effector T cells modified as described herein. In some embodiments, the cells are in vitro-derived, pluripotent stem cell-derived cells of any of the aforementioned cell types.

In some embodiments, the percentage of cells comprising the genetic disruption of a targeted gene (e.g., NR3C1) exhibit a non-activated, long-lived memory or central memory phenotype that is the same or substantially the same as a corresponding or reference population or composition of cells not containing the genetic disruption. In some embodiments, such property, activity or phenotype can be measured in an in vitro assay, such as by assaying an immunosuppressive activity of the cells. In some embodiments, any of the assessed activities, properties or phenotypes can be assessed at various days following electroporation or other introduction of the agent, such as after or up to 3, 4, 5, 6, 7 days. In some embodiments, such activity, property or phenotype is retained by at least 80%, 85%, 90%, 95% or 100% of the cells in the composition compared to the activity of a corresponding composition containing cells not comprising the genetic disruption of the targeted gene when assessed under the same conditions.

As used herein, reference to a "corresponding composition" or a "corresponding population of cells" (also called a "reference composition" or a "reference population of cells") refers to cells (e.g., Tregs, Teffs) obtained, isolated, generated, produced and/or incubated under the same or substantially the same conditions, except that the cells or population of cells were not introduced with the agent. In some aspects, except for not containing introduction of the agent, such cells are treated identically or substantially identically as cells that have been introduced with the agent, such that any one or more conditions that can influence the activity or properties of the cell, including the upregulation or expression of the inhibitory molecule, is not varied or not substantially varied between the cells other than the introduction of the agent.

Methods and techniques for assessing the expression and/or levels of cell markers (e.g., Treg markers) are known in the art. Antibodies and reagents for detection of such markers are well known in the art, and readily available. Assays and methods for detecting such markers include, but are not limited to, flow cytometry, including intracellular flow cytometry, ELISA, ELISPOT, cytometric bead array or other multiplex methods, Western Blot and other immunoaffinity-based methods. In some embodiments, the modified cells can be detected by flow cytometry or other immunoaffinity based method for expression of a marker unique to such cells, and then such cells can be co-stained for another marker.

In some embodiments, the cells, compositions and methods provide for the deletion, knockout, disruption, or reduction in expression of the target gene in hematopoietic cells or precursor cells thereof (e.g., Tregs, Teffs) to be adoptively transferred. In some embodiments, the methods are performed ex vivo on primary cells, such as primary hematopoietic cells or precursor cells thereof (e.g., Tregs, Teffs) from a subject. In some aspects, methods of producing or generating such cells including introducing into the cells an agent or agents that is capable of disrupting, a gene that encode the endogenous gene to be targeted (e.g., NR3C1), and introducing into the cells a calcineurin inhibitor resistance gene. As used herein, the term "introducing" encompasses a variety of methods of introducing DNA into a cell, either in vitro or in vivo, such methods including transformation, transduction, transfection (e.g. electroporation), and infection. Where the introducing involves electroporation, a polynucleotide (e.g., a plasmid, a single stranded DNA, a minicircle DNA) can be electroporated. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The population of cells can be cells that have been obtained from a subject, such as obtained from a peripheral blood mononuclear cells (PBMC) sample, an umbilical cord blood sample, an unfractionated T cell sample, a lymphocyte sample, a white blood cell sample, an apheresis product, or a leukapheresis product.

In some embodiments, the step of introducing the nucleic acid encoding a calcineurin inhibitor resistance gene and the step of introducing the agent (e.g., Cas/gRNA RNP) can occur simultaneously or sequentially in any order. In some embodiments, subsequent to introduction of the calcineurin inhibitor resistance gene and one or more gene editing agents (e.g. Cas/gRNA RNP), the cells are cultured or incubated under conditions to stimulate expansion and/or proliferation of cells.

Thus, provided are cells, compositions, and methods that enhance cell, such as Treg, function in adoptive cell therapy, including those offering improved efficacy, such as by increasing activity and potency of administered modified cells, while maintaining persistence or exposure to the transferred cells over time, or such as by increasing persistence and/or survival of the administered modified cells. In some embodiments, the modified cells, exhibit increased expansion and/or persistence when administered in vivo to a subject, as compared to certain available methods. In some embodiments, the provided cells exhibit increased persistence when administered in vivo to a subject. In some embodiments, the persistence of modified cells, in the subject upon administration is greater as compared to that which would be achieved by alternative methods, such as those involving administration of cells genetically engineered by methods in which cells were not introduced with an agent that reduces expression of or disrupts a gene encoding an endogenous gene (e.g., NR3C1). In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some embodiments, quantitative PCR (qPCR) is used to assess the quantity of modified cells in the blood or serum or organ or tissue (e.g., disease site) of the subject. In some embodiments, persistence is quantified as copies of DNA or plasmid encoding, e.g., a calcineurin inhibitor resistance gene, per microgram of DNA, or as the number of CNI resistance gene-expressing cells per microliter of the sample, e.g., of blood or serum, or per total number of peripheral blood mononuclear cells (PBMCs) or white blood cells or Tregs per microliter of the sample. In some embodiments, flow cytometric assays detecting cells generally using antibodies specific for, e.g., a calcineurin inhibitor resistance gene encoded protein, also can be performed. Cell-based assays may also be used to detect the number or percentage of functional cells.

The present disclosure provides methods for producing or generating a calcineurin inhibitor-resistant modified cell (e.g., Treg) of the invention. The cells generally are engineered by introducing one or more genetically engineered nucleic acids encoding the exogenous calcineurin inhibitor resistance gene product. In some embodiments, the cells also are introduced, either simultaneously or sequentially with the nucleic acid encoding the exogenous CNI resistance gene product, with an agent (e.g. Cas9/gRNA RNP) that is capable of disrupting a targeted gene (e.g., NR3C1).

In some embodiments, the calcineurin inhibitor resistance gene (e.g., encoding a calcineurin variant) is inserted into a genome via homology directed repair (HDR). As used herein, "homology-directed repair" or "HDR" is a mechanism to repair double stranded DNA breaks in cells. HDR generally relies on the process of homologous recombination, whereby stretches of nucleic acid sequence homology are used to repair the double stranded DNA break. During HDR, a strand of the homologous sequence of a nucleic acid donor invades, or hybridizes, with a resected portion of the cut DNA. A DNA polymerase, using the resected DNA as a primer, elongates the cut DNA, using the invaded donor sequence as a template. After elongation and break repair, the new sequence at the site of the cut possess whatever sequence was present in the nucleic acid donor used in the repair process. The process of HDR is further described in Jasin et al. (Cold Spring Harb. Perspect. Biol. 2013 November; 5 (11): a012740), incorporated herein by reference.

In some embodiments, the nucleic acid donor template (e.g., for insertion of a CNI resistance gene) may be employed with gene editing complexes (e.g., CRISPR/Cas system) to enable genome engineering at specific nucleotide positions in a homologous target nucleic acid of a host cell (e.g., homologous chromosomes that are compound heterozygous at a particular allele). In some aspects, the disclosure provides a method for targeted gene editing, the method comprising delivering to a cell (e.g., a cell of a disease subject) at least one component of a recombinant gene-editing complex together with the nucleic acid donor template, under conditions such that the recombinant gene editing complex induces a genetic lesion (e.g., nick or double stranded break) in a target site in the chromosome, and the donor template of the invention mediates a repair mechanism (e.g., HDR), thereby repairing the lesion.

Figure 15:
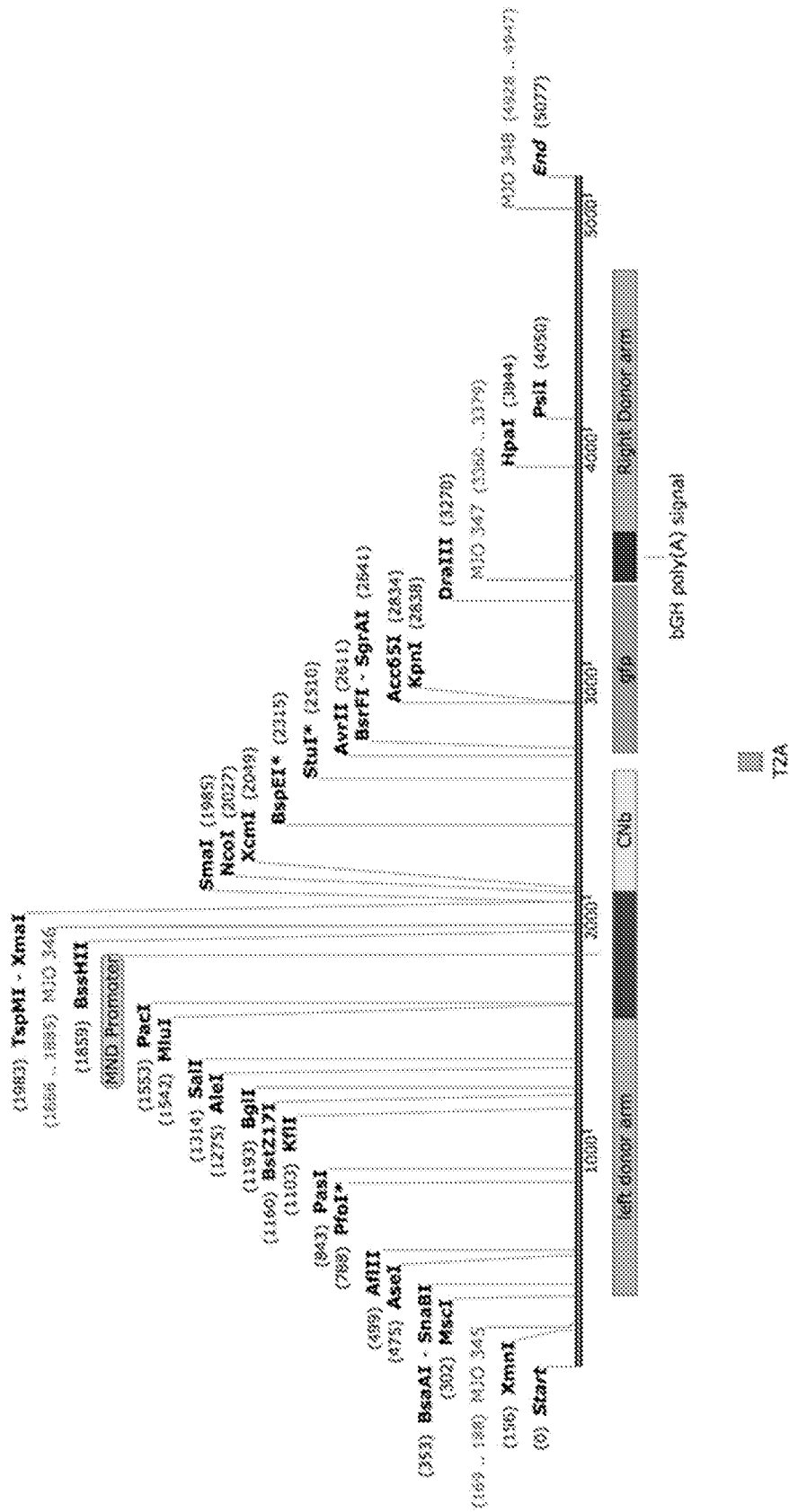
FIG. 15 depicts a schematic illustrating a nucleic acid donor insert that encodes for a calcineurin variant protein.

In certain embodiments, the nucleic acid donor template (also referred to herein as an exogenous donor DNA sequence) facilitates insertion of a calcineurin inhibitor resistance gene (e.g., mutant/variant calcineurin gene) into the NR3C1 locus via homologous recombination. Accordingly, in certain embodiments, the mutant calcineurin gene is inserted into the NR3C1 locus via homologous recombination using an exogenous donor DNA sequence comprising the nucleic acid sequence set forth in SEQ ID NO:11. A schematic of the exogenous donor DNA sequence is provided herein in FIG. 15.

In some embodiments, the donor DNA sequence can comprise transcriptional control elements such as, without limitation, a MND promoter, a CMB promoter, a EF-1alpha promoter, a PGK promoter. In some embodiments, the donor DNA sequence can comprise a reporter molecule such as, without limitation, a fluorescent marker (e.g., GFP), an epidermal growth factor receptor (EGFR), a nerve growth factor receptor (NGFR), an inducible caspase. Where the donor DNA sequence comprises both the primary insertion element (e.g., CNI resistance gene) and a secondary element (e.g., a reporter molecule), coordinated expression may be desired. Various methods of coordinated expression of one or more genes are known in the art. In some embodiments, the primary insertion element (e.g., CNI resistance gene) and the secondary insertion element (e.g., GFP) is separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. For example, a linker for use in a donor nucleic acid of the present disclosure comprising a CNI resistance gene and a reporter gene, allows for the CNI resistance gene product and the reporter gene product to be translated as a polyprotein that is dissociated into separate CNI resistance gene product and reporter gene product components.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunoglobulin heavy-chain binding protein or binding immunoglobulin protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAV), Thosea asigna virus (TaV), and porcine tescho virus-1 (PTV-1); and cardioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH-terminus of its consensus recognition sequence. Various furin consensus recognition sequences (or "furin cleavage sites") are known to those of skill in the art, including, without limitation, Arg-X-Lys-Arg (SEQ ID NO: 12) or Arg-X-Arg-Arg (SEQ ID NO:13), X1-Arg-X-X1-Arg (SEQ ID NO:14) and Arg-X-X-Arg (SEQ ID NO: 15), such as an Arg-Gln-Lys-Arg (SEQ ID NO: 16), where X is any naturally occurring amino acid, and X1 is Arg or Lys. Those of skill in the art would be able to select the appropriate Furin cleavage site for use in the present invention.

As used herein, the terms "nucleic acid donor" or "nucleic acid donor template" or "donor template" or "donor sequence" or "donor" or "nucleic acid insert" or "insert" refer to any nucleic acid sequence, e.g., deoxyribonucleic acid, that may be used as a repair template in the repair mechanism (e.g., homology-directed repair (HDR)). The nucleic acid donor may be double stranded or single stranded, e.g., double stranded DNA (dsDNA) or single stranded DNA (ssDNA). The nucleic acid donors of the disclosure may comprise varying polynucleotide lengths. In certain embodiments, the nucleic acid donor may be less than about 100 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, about 900 nucleotides in length, about 1000 nucleotides in length, or greater than about 1000 nucleotides in length. A nucleic acid donor of less than or equal to 200 nucleotides in length may also be referred to as a "short" nucleic acid donor. In certain embodiments, the nucleic acid donor is a single stranded donor oligonucleotide (ssODN). The nucleic acid donors to be inserted into the genome of a cell may be of any nucleotide length as needed by the skilled practitioner. For example, but in no way limiting, the nucleotide portion may be as short as a single nucleotide or greater than ten kilobases.

In some embodiments, the nucleic acid donors of the disclosure comprise a nucleotide sequence to be inserted into the genome of a cell, for example, an exogenous sequence to be inserted into the genome of a cell. The exogenous sequence may comprise a gene (e.g., a calcineurin inhibitor resistance gene). The gene may encode for a protein, such as a therapeutic protein or a selectable marker protein (e.g., a calcineurin variant). In certain embodiments, the selectable marker may encode for a selectable marker protein that confers resistance to an agent that reduces cell growth or causes cell death. Examples of such agents, included, but not limited to, ampicillin, blasticidin, bleomycin, chloramphenicol, gentamycin, hygromycin, kanamycin, lincomycin, methotrexate, neomycin, phosphinothricin, puromycin, tetracyclin, and zeocin. In other embodiments, the selectable marker may encode a fluorescent or luminescent protein (e.g., luciferase or GFP). The gene may be derived from the same species organism of the cell in which the gene is to be inserted. The gene may be derived from a different species organism of the cell in which the gene is to be inserted. The gene may be a chimeric sequence comprising sequences of multiple species. The nucleic acid donor may comprise a sequence that encodes for a non-coding RNA. Examples of non-coding RNAs include, but are not limited to, transfer RNAs (tRNAs), ribosomal RNAs (rRNAs), small RNAs such as siRNA, miRNA, piRNA, snoRNA, snRNA, exosomal RNA (exRNA). The nucleic acid donor may comprise a sequence that is not expressed. The nucleic acid donor may comprise a sequence that reduces or eliminates the expression of an endogenous gene in the cell.

In the case of HDR-mediated gene editing, the nucleic acid donors of the disclosure further comprise homology arms at the 5' end and 3' end, for example, a first and second homology arm. The homology arms are nucleic acid sequences that share sufficient homology with a target site in the genome of a cell to mediate HDR. Each homology arm may comprise varying polynucleotide lengths. It will be understood to those of skill in the art that homology arm nucleic acid sequences are an extension of the existing nucleic acid donor sequence as described above.

In certain embodiments the first homology arm may be about 20 nucleotides in length to about 1000 nucleotides in length. In certain embodiments the first homology arm may be less than about 20 nucleotides in length, about 20 nucleotides in length, about 30 nucleotides in length, about 40 nucleotides in length, about 50 nucleotides in length, about 60 nucleotides in length, about 70 nucleotides in length, about 80 nucleotides in length, about 90 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, about 900 nucleotides in length, about 1000 nucleotides in length, or greater than about 1000 nucleotides in length.

In certain embodiments the second homology arm may be about 20 nucleotides in length to about 1000 nucleotides in length. In certain embodiments the second homology arm may be less than about 20 nucleotides in length, about 20 nucleotides in length, about 30 nucleotides in length, about 40 nucleotides in length, about 50 nucleotides in length, about 60 nucleotides in length, about 70 nucleotides in length, about 80 nucleotides in length, about 90 nucleotides in length, about 100 nucleotides in length, about 200 nucleotides in length, about 300 nucleotides in length, about 400 nucleotides in length, about 500 nucleotides in length, about 600 nucleotides in length, about 700 nucleotides in length, about 800 nucleotides in length, about 900 nucleotides in length, about 1000 nucleotides in length, or greater than about 1000 nucleotides in length.

In certain embodiments, the first and second homology arm of the nucleic acid donor may comprise different nucleotide lengths. As an example for illustrative purposes, but in no way limiting, the homology arm at the 5' end of the nucleic acid donor (the first homology arm) may be 100 nucleotides in length and the homology arm at the 3' end of the nucleic acid donor (the second homology arm) may be 150 nucleotides in length.

In some embodiments, the calcineurin inhibitor resistance gene (e.g., encoding a calcineurin variant) is introduced into a cell by an expression vector. Expression vectors comprising a nucleic acid sequence encoding a calcineurin variant of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybac, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the calcineurin variant in the host cell. In some embodiments, the adenovirus genome is a 36 kb, linear, double stranded DNA, where a foreign DNA sequence (e.g., a nucleic acid encoding a calcineurin variant) may be inserted to substitute large pieces of adenoviral DNA in order to make the expression vector of the present invention (see, e.g., Danthinne and Imperiale, Gene Therapy (2000) 7 (20): 1707-1714).

Another expression vector is based on an adeno associated virus, which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Various AAV vectors are known in the art, including without limitation those derived from AAV1, AAV2, AAV3, AAV4, AAV5, AAV6, AAV7, AAV8, AAV9, or AAVrh10. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding a calcineurin variant) into the viral genome at certain locations to produce a virus that is replication defective. Though the retrovirus vectors are able to infect a broad variety of cell types, integration and stable expression of the calcineurin variant requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a calcineurin variant (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell is a hematopoietic cell or precursor thereof, e.g., a Treg, a T cell, an NK cell, or an NKT cell.

The present invention also provides genetically engineered cells which include and stably express a calcineurin variant of the present disclosure. In some embodiments, the genetically engineered cells are genetically engineered regulatory T cells (Tregs), T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Modified cells (e.g., comprising a calcineurin variant) may be produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a calcineurin variant of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5:505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a calcineurin variant of the present disclosure will be RNA, e.g., in vitro synthesized RNA. Methods for in vitro synthesis of RNA are known in the art; any known method can be used to synthesize RNA comprising a sequence encoding a calcineurin variant. Methods for introducing RNA into a host cell are known in the art. See, e.g., Zhao et al. Cancer Res. (2010) 15:9053. Introducing RNA comprising a nucleotide sequence encoding a calcineurin variant into a host cell can be carried out in vitro or ex vivo or in vivo. For example, a host cell (e.g., a Treg, an NK cell, a cytotoxic T lymphocyte, etc.) can be electroporated in vitro or ex vivo with RNA comprising a nucleotide sequence encoding a calcineurin variant.

The disclosed methods can be applied to the modulation of T cell activity in basic research and therapy, in the fields of cancer, stem cells, acute and chronic infections, autoimmune diseases, cell therapy, and gene therapy, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the cells (e.g., pluripotent stem cells, Tregs) can be incubated or cultivated prior to, during and/or subsequent to introducing the nucleic acid molecule encoding the exogenous calcineurin variant and the gene editing agent (e.g. Cas9/gRNA RNP). In some embodiments, the cells (e.g., pluripotent stem cells, Tregs) can be incubated or cultivated prior to, during or subsequent to the introduction of the nucleic acid molecule encoding the exogenous receptor, such as prior to, during or subsequent to the transduction of the cells with a viral vector (e.g., lentiviral vector) encoding the exogenous receptor. In some embodiments, the cells (e.g., T cells) can be incubated or cultivated prior to, during or subsequent to the introduction of the gene editing agent (e.g. Cas9/gRNA RNP), such as prior to, during or subsequent to contacting the cells with the agent or prior to, during or subsequent to delivering the agent into the cells, e.g. via electroporation. In some embodiments, the incubation can be both in the context of introducing the nucleic acid molecule encoding the exogenous receptor and introducing the gene editing agent, e.g. Cas9/gRNA RNP.

In some embodiments, introducing the gene editing agent, e.g. Cas9/gRNA RNP, is after introducing the nucleic acid molecule encoding the calcineurin variant. In some embodiments, prior to the introducing of the agent, the cells are rested, e.g. by removal of any stimulating or activating agent. In some embodiments, prior to introducing the agent, the stimulating or activating agent and/or cytokines are not removed. Those of skill in the art will be able to determine the order in which each of the one or more nucleic acid sequences are introduced into the host cell.

Accordingly, a method for generating a modified hematopoietic cell or precursor cell thereof is provided, comprising introducing into the cell a CRISPR system that produces an indel in exon 2 of NR3C1, wherein the indel is capable of downregulating gene expression of NR3C1. In an exemplary embodiment, the method further comprises an insertion of an exogenous calcineurin inhibitor resistance gene into the genome of the cell, wherein the insertion occurs at the site of the indel NR3C1.

D. Nucleic Acids and Expression Vectors

The present disclosure provides a nucleic acid encoding an exogenous calcineurin variant. In some embodiments, a nucleic acid of the present disclosure may be operably linked to a transcriptional control element, e.g., a promoter, and enhancer, etc. Suitable promoter and enhancer elements are known to those of skill in the art.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an Ncrl (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173 (1): 86-93; Alpuche-Aranda et al., Proc. Natl. Acad. Sci. USA (1992) 89 (21): 10079-83), a nirB promoter (Harborne et al. Mol. Micro. (1992) 6:2805-2813), and the like (see, e.g., Dunstan et al., Infect. Immun. (1999) 67:5133-5141; Mckelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28: e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35:2543-2549; Borras et al., Gene Ther. (1999) 6:515-524; Li and Davidson, Proc. Natl. Acad. Sci. USA (1995) 92:7700-7704; Sakamoto et al., H. Gene Ther. (1999) 5:1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9:81-86, Flannery et al., Proc. Natl. Acad. Sci. USA (1997) 94:6916-6921; Bennett et al., Invest. Opthalmol. Vis. Sci. (1997) 38:2857-2863; Jomary et al., Gene Ther. (1997) 4:683 690, Rolling et al., Hum. Gene Ther. (1999) 10: 641-648; Ali et al., Hum. Mol. Genet. (1996) 5:591-594; Srivastava in WO 93/09239, Samulski et al., J. Vir. (1989) 63:3822-3828; Mendelson et al., Virol. (1988) 166:154-165; and Flotte et al., Proc. Natl. Acad. Sci. USA (1993) 90:10613-10617); SV40; herpes simplex virus; human immunodeficiency virus (see, e.g., Miyoshi et al., Proc. Natl. Acad. Sci. USA (1997) 94:10319-23; Takahashi et al., J. Virol. (1999) 73:7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a calcineurin variant of the present disclosure. Methods for introducing RNA into a host cell are known in the art. See, e.g., Zhao et al. Cancer Res. (2010) 15:9053. Introducing RNA comprising a nucleotide sequence encoding a calcineurin variant of the present disclosure into a host cell can be carried out in vitro or ex vivo or in vivo. For example, a host cell (e.g., a Treg, an NK cell, a cytotoxic T lymphocyte, etc.) can be electroporated in vitro or ex vivo with RNA comprising a nucleotide sequence encoding a calcineurin variant of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479:79-82).

E. Sources of Cells

Cells suitable for the present invention include without limitation, naive cells, effector memory cells, central memory cells, stem central memory cells, effector memory cells, and long-lived effector memory cells. In some embodiments, the cells include without limitation, immune suppressive cells, such as regulatory T cells (Tregs), non-Tregs modified to be directly immune suppressive (e.g., via secretion of IL-10 or TGF-β), and non-Tregs modified to be indirectly immune suppressive (e.g., cytotoxic T lymphocytes (CTLs) that kill antigen presenting cells (APCs)). In some embodiments, the cells include without limitation, dendritic cells, myeloid derived suppressor cells, immunoregulatory macrophages, mesenchymal stem cells, multipotent adult progenitor cells, embryonic stem cells, induced pluripotent stem cells, innate lymphoid cells, invariant natural killer (NK) T cells. In some embodiments, the cells include hematopoietic cells and precursor cells thereof.

Prior to expansion, a source of immune cells is obtained from a subject for ex vivo manipulation. Sources of target cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including embryonic stem cells (ESCs) and induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune cells are obtained from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker-) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO-, CD45RA+, CD62L+, CD4+ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CDl1b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

F. Expansion of Cells

Whether prior to or after modification of cells, the cells, e.g., immune cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005.

Examples of methods for expanding Treg cells are well known to the skilled artisan, and include, but are not limited to: use of stimulatory antibodies, commonly anti-CD3 and anti-CD28, absorbed on magnetic beads or nanoparticles and use of stimulatory cytokines (commonly from the group of IL-2, IL-15 and IL-4); use of stimulatory antibodies, commonly anti-CD3 and anti-CD28, and use of ligands specific for the stimulatory antibodies absorbed on magnetic beads or nanoparticles and use of stimulatory cytokines (commonly from the group of IL-2, IL-15 and IL-4); use of stimulatory antibodies, commonly anti-CD3 and anti-CD28, coated on a surface of a cell culture vessel and use of stimulatory cytokines (commonly from the group of IL-2, IL-15 and IL-4); and use of feeder cells, as described in WO2006/108882, which is incorporated herein by reference. Examples of methods for differentiating T cells into regulatory T cells are well known in the art and include, without limitation, exposure to rapamycin, dexamethasone, IL-10, IFN-alpha, tolerogenic antigen presenting cells such as dendritic cells and the like.

In some embodiments, regulatory T cells may be obtained by the method described in Wakkach et al (Immunity 2003 May; 18 (5): 605-17), and comprising the steps of: a) isolating a progenitor cell population from a subject; b) obtaining a population of dendritic cells by culturing the progenitor cell population in the presence of IL-10 (in a concentration ranging from 50 to 250 U/ml, preferably at 100 U/ml in the culture medium); c) contacting cells of step b) with a CD4+ T lymphocyte population isolated from the subject in the presence of a specific antigen, to allow differentiation of CD4+ T cells directed to the antigen into the regulatory T cell population; and d) recovering the regulatory T cell population from the step c). The method may also be carried out using Dexamethasone and Vitamin D3, or tolerogenised or immature DCs instead of the DCs of step b).

In some embodiments, regulatory T cells may be obtained by the method described in the patent U.S. Pat. No. 6,746,670 and comprising the steps of: a) culturing a CD4+ T cell population directed to a specific antigen, isolated from a subject in a medium with an appropriate amount of IFN-alpha (preferably at 5 ng/ml of culture medium); and b) recovering the regulatory T cell population. In step a), the medium may further comprise an appropriate amount of IL-10, preferably at 100 U/ml. In step b), the regulatory T cell population may be cultured in a medium comprising IL-15 to allow proliferation, IL-15 being preferably at 5 ng/ml in the medium.

In some embodiments, regulatory T cells may be obtained by the method described in the patent application WO02/092793 and comprising the steps of: a) in vitro activating a CD4+ T cell population in presence of a specific antigen, presented by artificial antigen presenting cells; and b) recovering an activated CD4+ T cells comprising at least 10% of regulatory T cells. In some embodiments, the artificial antigen presenting cells express a HLA II system molecule and a human LFA-3 molecule and do not express the co-stimulation molecules B7-1, B7-2, B7-H1, CD40, CD23 and ICAM-I.

In some embodiments, regulatory T cells may be obtained by the method described in Groux et al. (Nature 1997, 389 (6652): 737-42), and comprising the steps of: a) in vitro activating a CD4+ T cell population in presence of a specific antigen and an appropriate amount of IL-10 (preferably at 100 U/ml of culture medium); and b) recovering the regulatory T cell population. Preferably, IL-10 is present in the medium.

In some embodiments, regulatory T cells may be obtained by the method described in the patent application WO2007/010406, comprising the steps of: a) stimulating a leukocyte population or a peripheral blood mononuclear cell (PBMC) population with a specific antigen; b) recovering the antigen-specific Treg cell population from the stimulated population; and c) optionally expanding the antigen-specific Treg cell population.

Other methods of obtaining regulatory T cells are known in the art, including, for example, inducing the generation of Tregs from non-Treg populations as described in U.S. Pat. No. 9,228,172 and U.S. Publication No. US201601571471A1.

In some embodiments, ex vivo culture-expanded regulatory T cells may be obtained by the methods described in U.S. Pat. Nos. 7,651,855, 8,129,185, and 9,181,526. In some embodiments, regulatory T cells may be isolated from a population of cells obtained from cord blood, as described in U.S. Pat. Nos. 9,273,282, and 9,187,727. Methods to expand regulatory T cells are also described in U.S. Publication No. 20130101567. In some embodiments, Tregs may be obtained by converting non-Tregs into Tregs according to the methods described in U.S. Pat. No. 9,228,172 and U.S. Publication No. 20160151471. In some embodiments, a regulatory T cell can be obtained by converting T cells into Tregs, according to the methods described in U.S. Pat. No. 9,644,179 and U.S. Publication No. 20170211042.

Leukocytes encompass several types of cells, which are characterized by their importance, their distribution, their number, their lifetime and their potentiality. These types are the following: the polynuclear or granular leukocytes, among which one finds the eosinophilic, the neutrophilic and the basophilic leukocytes, and the mononuclear cells, or peripheral blood mononuclear cells (PBMCs), which are large white blood cells and consist in the major cell types of the immune system (lymphocytes and monocytes). The leukocytes or the PBMCs can be separated from the peripheral blood by any method known to those skilled in the art. Advantageously, for the separation of the PBMCs, centrifugation may be used, preferably density gradient centrifugation, preferably discontinuous density gradient centrifugation. An alternative is the use of specific monoclonal antibodies. In certain embodiments PBMC are typically isolated from the whole blood product by means of Ficoll-Hypaque, using standard procedures. In other embodiments the PBMCs are recovered by means of leukapheresis.

In some embodiments, regulatory T cells may be obtained by: a) culturing a leukocyte population or a peripheral blood mononuclear cell (PBMC) population with mesenchymal stem cells in the presence of a specific antigen; and b) recovering the Treg cell population. Such a method can also be carried out with naive or memory T cells instead of PBMC or leukocytes.

In some embodiments, Treg cells can be obtained by culturing T cells in the presence of IL-2 and TGF-beta (Davidson et al. The Journal of Immunology, 2007, 178: 4022-4026). In another embodiment, Treg cells can be obtained by culturing T cells in the presence of TGF-beta.

Expanding cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween.

Following culturing, the cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The cell medium may be replaced during the culture of the cells at any time. Preferably, the cell medium is replaced about every 2 to 3 days. The cells are then harvested from the culture apparatus whereupon cells can be used immediately or cryopreserved to be stored for use at a later time. In one embodiment, the invention includes cryopreserving the expanded cells. The cryopreserved cells are thawed prior to introducing nucleic acids into the cell.

In some embodiments, the method comprises isolating cells and expanding the cells. In another embodiment, the invention further comprises cryopreserving the cells prior to expansion. In yet another embodiment, the cryopreserved cells are thawed for electroporation with the RNA encoding the chimeric membrane protein.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

In one embodiment, the cells may be cultured for several hours (about 3 hours) to about 14 days or any hourly integer value in between. Conditions appropriate for Treg cell culture include an appropriate media that may contain factors necessary for proliferation and viability, and/or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of Tregs. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the Tregs expand in the range of about 20 fold to about 50 fold, or more. In one embodiment, human T regulatory cells are expanded via anti-CD3 antibody coated KT64.86 artificial antigen presenting cells (aAPCs). Methods for expanding and activating Tregs are described herein.

In one embodiment, the method of expanding the Tregs can further comprise isolating the expanded Tregs for further applications. In another embodiment, the method of expanding can further comprise a subsequent electroporation of the expanded Tregs followed by culturing. The subsequent electroporation may include introducing a nucleic acid encoding an agent, such as transducing the expanded Tregs, transfecting the expanded Tregs, or electroporating the expanded Tregs with a nucleic acid, into the expanded population of Tregs, wherein the agent further stimulates the Treg. The agent may stimulate the Tregs, such as by stimulating further expansion, or function.

G. Methods of Treatment

The modified cells (e.g., Tregs) described herein may be included in a composition for immunotherapy, in particular suppression immunotherapy. The composition may include a pharmaceutical composition and further include a pharmaceutically acceptable carrier. A therapeutically effective amount of the pharmaceutical composition comprising the modified cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells.

Also included is a method of treating a disease or condition in a subject in need thereof comprising administering to the subject a genetically edited modified cell (e.g., genetically edited modified Treg, genetically edited modified Teff). In one embodiment, the method of treating a disease or condition in a subject in need thereof comprises administering to the subject a steroid and/or calcineurin inhibitor and/or immunosuppressant drug-resistant cell of the present disclosure.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8 (10): 577-85). See, e.g., Themeli et al. (2013) Nat Biotechnol. 31 (10): 928-933; Tsukahara et al. (2013) Biochem Biophys Res Commun 438 (1): 84-9; Davila et al. (2013) PLOS ONE 8 (4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g., GVHD, prior to administration of the cells or composition containing the cells. In some embodiments, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy. In some embodiments the subject has been treated with a standard of care prophylaxis for GVHD, such as a steroid (e.g., glucocorticoid) and/or calcineurin inhibitor (e.g., FK506, CsA).

In some cases, the cells are genetically edited Teffs as described herein. In some embodiments, the method comprises administering genetically edited Teffs to a subject to a hematopoietic stem cell transplant patient treated with glucocorticoids or CaNI. Without being bound to any particular theory or mode of action, administration of modified Teffs, in which the glucocorticoid receptor locus has been modified to increase sensitivity to steroids and/or calcineurin inhibitors, is believed to increase or maintain Teff survival in such patients. In some cases, the modified Teffs are tumor specific or enriched for a particular tumor type. In some cases, the modified Teffs are pathogen-specific (e.g., specific to cytomegalovirus or BK virus).

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject has received a stem cell transplant, or is a candidate for stem cell transplantation. In some embodiments, the subject has received a solid organ transplant, or is a candidate for solid organ transplantation. In some embodiments, the subject is suffering from an autoimmune disorder. In some embodiments, the subject is suffering from graft versus host disease (GVHD). In some embodiments, the subject is suffering from type 1 diabetes.

In one embodiment, the method of treating a disease or condition in a subject in need thereof comprises administering to the subject a therapeutically effective amount of a steroid and/or calcineurin inhibitor-resistant cell of the invention. In one embodiment, the method of treating a disease or condition in a subject in need thereof comprises administering to the subject a therapeutically effect amount of a steroid and/or calcineurin inhibitor-resistant Treg.

The steroid and/or calcineurin inhibitor-resistant cells of the invention are able to engraft, survive, persist, and/or proliferate during the conditions of conventional standard(s) of care of immunotherapies such as administration of glucocorticoids and calcineurin inhibitors that serve to suppress and/or induce senescence and/or cytotoxicity in cells of the lymphohematopoetic system. As such, the cells of the invention are able to exert their therapeutic effect for longer and sustained periods.

When a steroid and/or calcineurin inhibitor-resistant cell of the invention is administered, the transplanted tissue is protected from rejection. In one embodiment, a steroid and/or calcineurin inhibitor-resistant cell can mediate persistent immunosuppression. In one embodiment, a steroid and/or calcineurin inhibitor-resistant cell can suppress T cell proliferation in response to allogeneic antigens. In some embodiments, upon cell, tissue, and/or organ transplantation, allogeneic antigens may be ubiquitously expressed on the transplanted cells, tissues, and/or organs. In such cases, substantial immune cell infiltration into the transplanted cells, tissues, and/or organs may occur, resulting in destruction of the transplanted cells, tissues, and/or organs. Accordingly, in some embodiments, a steroid and/or calcineurin inhibitor-resistant cell of the invention is capable of reducing infiltration of immune cells, and thus protecting the transplanted cells, tissues, and/or organs from destruction. In some cases, the transplanted cells, tissues, and/or organs may mediate toxicity. Accordingly, in some embodiments, a steroid and/or calcineurin inhibitor-resistant cell of the invention is able to reduce transplanted cells, tissues, and/or organ-mediated toxicity.

Accordingly, the present invention provides a method for achieving a preventative therapeutic effect in a subject in need thereof, and/or a method for achieving an immunosuppressive effect in a subject in need thereof e.g. one who is experiencing an alloresponse or autoimmune response. In some embodiments, a method for achieving a preventative therapeutic effect in a subject in need thereof, and/or a method for achieving an immunosuppressive effect in a subject in need thereof with an alloresponse or autoimmune response, comprises administering to the subject a steroid and/or calcineurin inhibitor-resistant cell of the invention.

The methods of the present invention should be construed to include protection from rejection of any type of transplanted organ, tissue, or cells, including but not limited to lungs, hearts (e.g., cardiomyocytes), heart valves, skin (e.g., fibroblasts), liver (e.g., hepatocytes), hand, kidneys, pancreas, intestines, stomach, thymus, bones, tendons, cornea, testes, nerves, veins, blood (e.g., whole blood, white blood cells, red blood cells, platelets, plasma, serum), bone marrow (e.g., monocytes, macrophages, mesenchymal stem cells), stem cells (e.g., mesenchymal stem cells (MSCs), hematopoietic stem cells (HSCs)), islets of Langerhans cells, neural cells (e.g., neurons, macroglia, microglia), immune cells (e.g., T cells, Natural Killer (NK) cells, or NKT (Natural Killer T) cells), and hematopoietic cells, and components thereof. Other tissues and cell types for which the methods can provide protection from rejection include, without limitation, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islet of Langerhans cells, pancreatic insulin secreting cells, pancreatic alpha-2 cells, pancreatic beta cells, pancreatic alpha-1 cells, bone cells, bone precursor cells, neuronal stem cells, primordial stem cells, hepatocytes, aortic endothelial cells, microvascular endothelial cells, umbilical vein endothelial cells, fibroblasts, liver stellate cells, aortic smooth muscle cells, cardiac myocytes, neurons, Kupffer cells, smooth muscle cells, Schwann cells, erythrocytes, platelets, neutrophils, lymphocytes, monocytes, eosinophils, basophils, adipocytes, chondrocytes, pancreatic islet cells, thyroid cells, parathyroid cells, parotid cells, glial cells, astrocytes, red blood cells, white blood cells, macrophages, somatic cells, pituitary cells, adrenal cells, hair cells, bladder cells, kidney cells, retinal cells, rod cells, cone cells, heart cells, liver cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopaminergic cells, squamous epithelial cells, osteocytes, osteoblasts, osteoclasts, embryonic stem cells, fibroblasts and fibroblasts. The methods of the invention also include protection against graft versus host disease (GVHD).

In certain embodiments, the subject can be administered, in addition to the steroid and/or calcineurin inhibitor-resistant cell, a secondary treatment, such as an immunosuppressive drug. Examples of immunosuppressive drugs include but are not limited to prednisone, azathioprine, tacrolimus, and cyclosporine A. In some embodiments, the secondary treatment is a steroid and/or a calcineurin inhibitor. In some embodiments, the steroid is a corticosteroid. In some embodiments, the steroid is a glucocorticoid selected from the group consisting of a progesterone-type glucocorticoid, a hydrocortisone-type glucocorticoid, a methasone-type glucocorticoid, and an acetonide-type glucocorticoid. In some embodiments, the glucocorticoid is selected from the group consisting of dexamethasone, betamethasone, hydrocortisone (cortisol), prednisone, prednisolone, loteprednol, deflazacort, methylprednisolone, triamcinolone, fludrocortisone, and deoxycorticosterone, and derivatives and analogs thereof. In some embodiments, the calcineurin inhibitor is selected from the group consisting of cyclosporin, voclosporin, pimecrolimus, and tacrolimus, and derivatives and analogs thereof.

In some embodiments, the subject is provided a secondary treatment. Secondary treatments include but are not limited to chemotherapy, radiation, surgery, and medications.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio, e.g., within a certain tolerated difference or error of such a ratio.

In some embodiments, the cells are administered at or within a tolerated difference of a desired dose of one or more of the individual populations or sub-types of cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ cells. In some embodiments, the cells are administered at or within a certain range of error of between about $10^8$ and $10^{12}$ or between about $10^{10}$ and $10^{11}$ T cells, between about $10^5$ and $10^{12}$ or between about $10^{10}$ and $10^{11}$ cells.

In some embodiments, the cells are administered at or within a tolerated range of a desired output ratio of multiple cell populations or sub-types. In some aspects, the desired ratio can be a specific ratio or can be a range of ratios, for example, in some embodiments, the desired ratio is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells are in some embodiments co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells is measured by assaying expression and/or secretion of one or more cytokines. In some aspects the biological activity is measured by assessing clinical outcome, such as reduction in tumor burden or load.

H. Pharmaceutical Compositions and Formulations

Also provided are populations of hematopoietic cells or precursor cells thereof of the invention, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

J. Animal Models

The present invention provides an in vivo animal model of a disease or condition following the transplantation (e.g., of a cell or tissue). In some embodiments, the animal model is of a disease or condition following an allogeneic transplantation (e.g., of a cell or tissue). In some embodiments, the animal model is of a disease or condition following a xenogeneic transplantation (e.g., of a cell or tissue). In certain embodiments, the present invention provides an in vivo animal model of graft versus host disease (GVHD) following an allogeneic transplantation (e.g., of a cell or tissue). In certain embodiments the present invention provides an in vivo animal model of graft versus host disease (GVHD) following a xenogeneic transplantation (e.g., of a cell or tissue). The present invention also provides methods of making such animal models.

In some embodiments, an in vivo animal model of GVHD following an allogeneic or xenogeneic transplantation comprises an animal comprising a population of allogeneic cells. As used herein, the term "allogeneic" refers to a material that is genetically dissimilar but of the same species, which may be immunologically incompatible. For example, an allogeneic cell or tissue is a cell or tissue derived from a genetically dissimilar source that is from the same species. As used herein, the term "xenogeneic" refers to a material that belongs to a different species. For example, a xenogeneic cell or tissue is a cell or tissue derived from a different species.

As provided herein, an in vivo animal model of GVHD is a murine model of GVHD. In some embodiments, the allogeneic cells are allogeneic plasma blood mononuclear cells (PBMCs). In some embodiments, the xenogeneic cells are xenogeneic PBMCs. In some embodiments, the murine GVHD model comprises an immunodeficient mouse comprising a population of allogeneic (i.e., derived from a genetically dissimilar mouse) or xenogeneic (i.e., derived from a different species) PBMCs.

Various immunodeficient mouse strains are known in the art, including without limitation, immunodeficient mouse strains of the "nude," "scid," "rag-deficient," and "higher-order, multigenic" varieties. Nude mice are homozygous for the Foxn1$^{nu}$ mutation. Foxn1 encodes a transcription factor required for both hair follicle and thymic development. In its absence, mice are both hairless and athymic. Because the thymus fails to form, there is no place for CD4+ and CD8+ T cells to differentiate and mature, making nude homozygotes T cell-deficient. Scid mice are homozygous for the Prkdc$^{scid}$ mutation. The gene Prkdc encodes the catalytic subunit of DNA-dependent protein kinase that is required for DNA repair and for sealing the double-stranded DNA breaks that occur during somatic recombination of T cell receptor (TCR) and immunoglobulin (Ig) genes. In the absence of Prkdc protein, TCR and Ig genes cannot rearrange, resulting in mice that are both T and B cell deficient. Rag-deficient mice are mice that fail to express functional Rag1 or Rag2 proteins. Like the Prkdc gene, both Rag1 and Rag2 are required for somatic recombination of TCR and Ig genes, and the absence of either gene results in T and B cell deficiency. Mice that carry either the Rag1$^{tm1Mom}$ or Rag2$^{tm1.1Cgn}$ mutations have very similar, if not identical, phenotypes. Higher-order, multigenic immunodeficient mice are constructed from either Prkdc$^{scid}$ or Rag-deficient mice, and carry additional immunodeficiency-enhancing mutations. Among these mice are our NSG and NRG mice, which carry a specific mutation in the interleukin 2 receptor gamma subunit gene (Il2rg$^{tm1Wjl}$) in combination with the Prkdc$^{scid}$ and Rag1$^{tm1Mom}$, respectively. These mice are B, T and NK cell deficient. Additionally, because they both have NOD/ShiLtJ genetic backgrounds, they are hemolytic complement-deficient and carry alleles that adversely affect macrophage and dendritic cell functions. In certain embodiments, the immunodeficient mouse is a BALB/c mouse. In certain embodiments, the immunodeficient mouse is a NOD/Scid/IL-2Rg–/–(NSG) mouse.

In some embodiments, a population of allogeneic PBMCs can be derived from a donor mouse that is genetically dissimilar. In certain embodiments, the donor mouse is a C57BL/6 mouse. In certain embodiments, the population of allogeneic PBMCs is derived from the bone marrow of a C57BL/6 mouse. Accordingly, an allogeneic GVHD murine model of the present invention comprises an immunodeficient BALB/c mouse comprising a population of allogeneic PBMCs derived from the bone marrow of a donor C57BL/6 mouse.

In some embodiments, a population of xenogeneic PBMCs can be derived from a human. Accordingly, a xenogeneic GVHD murine model of the present invention comprises an immunodeficient NSG mouse comprising a population of xenogeneic PBMCs derived from a human.

In some embodiments, a method of making a GVHD animal model of the present disclosure comprises injecting/administering a population of allogeneic or xenogeneic PBMCs into a host animal (e.g., mouse). In some embodiments, a method of making a GVHD murine model of the present disclosure comprises injecting/administering a population of allogeneic or xenogeneic PBMCs into an immunodeficient mouse. In some embodiments, a method of making an allogeneic GVHD murine model of the present disclosure comprises injecting/administering a population of allogeneic PBMCs into an immunodeficient mouse. In some embodiments, a method of making a xenogeneic GVHD murine model of the present disclosure comprises injecting/administering a population of xenogeneic PBMCs into an immunodeficient mouse.

In some embodiments, the immunodeficient mouse is non-lethally irradiated prior to injection with allogeneic or xenogeneic PBMCs. In certain embodiments, non-lethally irradiating the immunodeficient mouse comprises subjecting the mouse to a dose of radiation that is about 50 rad to about 200 rad. In some embodiments, non-lethally irradiating the immunodeficient mouse comprises subjecting the mouse to a dose of radiation that is about 35, about 40, about 45, about 50, about 55, about 60, about 65, about 70, about 80, about 90, about 100, about 110, about 120, about 130, about 140, about 150, about 160, about 170, about 175, about 180, about 185, about 190, about 195, about 200, about 205, about 210, about 215, about 220, about 225 rad, or any value inbetween. Those of skill in the art will be able to determine the appropriate non-lethal dosage of radiation to administer to a mouse.

In certain embodiments, the immunodeficient mouse is injected/administered with about $1 \times 10^6$ to about $20 \times 10^6$ allogeneic or xenogeneic PBMCs. In some embodiments, the immunodeficient mouse is injected/administered with about $0.5 \times 10^6$, $0.6 \times 10^6$, $0.7 \times 10^6$, $0.8 \times 10^6$, $0.9 \times 10^6$, $1 \times 10^6$, $1.1 \times 10^6$, $1.2 \times 10^6$, $1.3 \times 10^6$, $1.4 \times 10^6$, $1.5 \times 10^6$, $2 \times 10^6$, $3 \times 10^6$, $4 \times 10^6$, $5 \times 10^6$, $10 \times 10^6$, $15 \times 10^6$, $16 \times 10^6$, $17 \times 10^6$, $18 \times 10^6$, $19 \times 10^6$, $19.5 \times 10^6$, $19.6 \times 10^6$, $19.7 \times 10^6$, $19.8 \times 10^6$, $19.9 \times 10^6$, $20 \times 10^6$, $20.1 \times 10^6$, $20.2 \times 10^6$, $20.3 \times 10^6$, $20.4 \times 10^6$, $20.5 \times 10^6$, $21 \times 10^6$, $22 \times 10^6$, $23 \times 10^6$, $24 \times 10^6$, $25 \times 10^6$ allogeneic or xenogeneic PBMCs, or any value inbetween. Those of skill in the art will be able to determine the appropriate number of PBMCs to inject into the immunodeficient mouse.

In some embodiments, the survival of a GVHD animal model of the present invention is reduced when treated with steroids and/or calcineurin inhibitors, as compared to a wild-type animal. In certain embodiments, the survival of a GVHD murine model of the present invention is reduced when treated with steroids and/or calcineurin inhibitors, as compared to a wild-type mouse.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The following experimental examples are not intended to be limiting, and relate to compositions and methods for generating steroid and/or calcineurin inhibitor resistant immune cells.

Materials and Methods

GMP Compliant Tregs

Tregs were purified from human apheresis products in a two step procedure whereby CD25+ cells (including Tregs) were positively selected using GMP grade mAb-conjugated magnetic beads and then sorted for naïve and memory Treg PB (CD4+25++127-45RA+ and CD4+25++127-45RA−, respectively) (FIG. 1). Purified cells were stimulated with GMP-quality artificial antigen presenting cells (aAPC) and cultured for 14 days in high dose IL-2 (300 U/ml). Expanded Tregs were banked (frozen) on day 14. For the experiments described herein, Tregs were thawed and re-stimulated with GMP-compliant anti-CD3/28 beads for 7-10 days. Treg purity and in vitro suppressive function were assessed at the end of the culture. Cultures of naïve and memory Tregs showed similar numbers of Foxp3+ cells, and all cultures were suppressive in vitro.

Example 1: Dexamethasone Effects on Treg Survival and Expansion

To determine whether Tregs are sensitive to the immunosuppressive effects of glucocorticoid receptor activation, a source of banked Tregs was generated. The banked Tregs were generated from magnetic bead enriched peripheral blood cells (4+25++127lo and variations of CD45RA+ and CD45RA− for naïve and effector memory cells, respectively). Purified Tregs were expanded in a 14 day culture using IL-2, K562-CD64/86 cells loaded with anti-CD3 mAb to provide greater consistency in replicate experiments. Banked tTregs were thawed, re-stimulated using anti-CD3/28 mAb beads, and then further expanded for 4±1 days or longer as indicated. Tregs were then split into cultures±Dexamethasone (Dex: 10, 30, 100 μg/ml), and relative survival by flow cytometry using a viability dye and counting beads was assessed after 2-3 days.

Dex decreased Treg numbers in the cultures in a dose-dependent manner (FIG. 2B). Without being bound by any theory, Treg expansion cultures contained 10-35% Foxp3− cells as a result of extended culture in the absence of rapamycin and using magnetic beads rather than flow sorting. To exclude the possibility that the reduction in cell numbers was due to a preferential loss of Tregs, the above cultures were also stained with CD127 and Foxp3 and the relative susceptibility to Dex for Treg (CD4+CD127− Foxp3+) and non-Tregs was determined (FIG. 2C). Dex treatment did not significantly impact the purity of Treg cultures, indicating that Treg viability/survival was adversely affected by Dex. The suppressive function of Tregs grown ±30 μg/ml Dex was tested (FIG. 2D). Exposure of Tregs to Dex in the re-expansion culture increased suppressive function.

Example 2: Gene Targeting Strategy

The Nuclear Receptor Subfamily 3, Group C, Member 1 (NR3C1) gene encodes the glucocorticoid receptor (GR, also known as NR3C1) which is the receptor to which cortisol and other glucocorticoids bind. The targeting strategy was to disrupt exon two via programmable nuclease gene disruption and mutagenic DNA repair through the error prone nonhomologous end-joining pathway (NHEJ). To definitively define the conditions for gene targeting application in Tregs, a comprehensive approach was taken for direct gene disruption of NR3C1 as well as a novel homology directed repair approach.

A strategy was developed to generate dual drug (steroid and calcineurin inhibitor) resistance by targeted insertion of a calcineurin inhibitor resistance gene in such a manner that it disrupted the glucocorticoid receptor locus. To accomplish this, four reagents derived from the clustered regularly interspaced palindromic repeats (CRISPR)/Cas9 system were designed for testing. Studies were performed in Jurkat cells in order to optimize the delivery and drug dosing parameters. Cas9 mRNA with guide RNAs (gRNAs) that were specially modified with nuclease resistant phosphorothioate bonds to prevent intracellular degradation were tested. In parallel, Cas9 protein complexed with a gRNA as a ribonucleoprotein (RNP) product was tested. The two delivery methods were compared for both gene disruption and homology directed repair (HDR)-based gene editing. After exhaustive dosing, timing, and electroporation condition optimization Cas9 RNP was identified as the optimal gene disruption and repair platform in Jurkat cells. This strategy did not require chemically modified gRNAs, and under some conditions may represent a more streamlined engineering, synthesis, and delivery method for research and clinical grade genome engineering and cellular manufacturing.

Figure 3B:
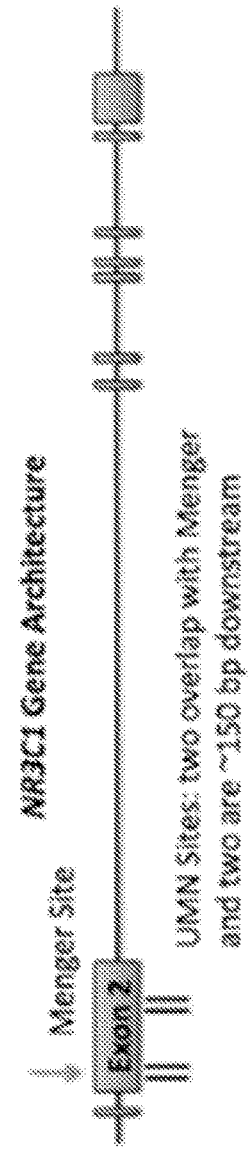
Figure 3C:
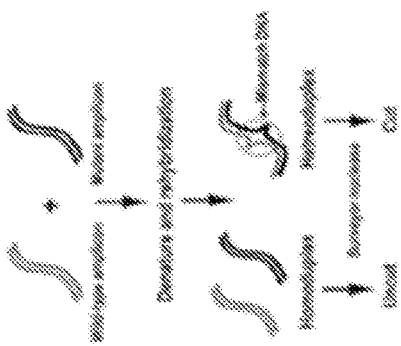
Figure 3D:
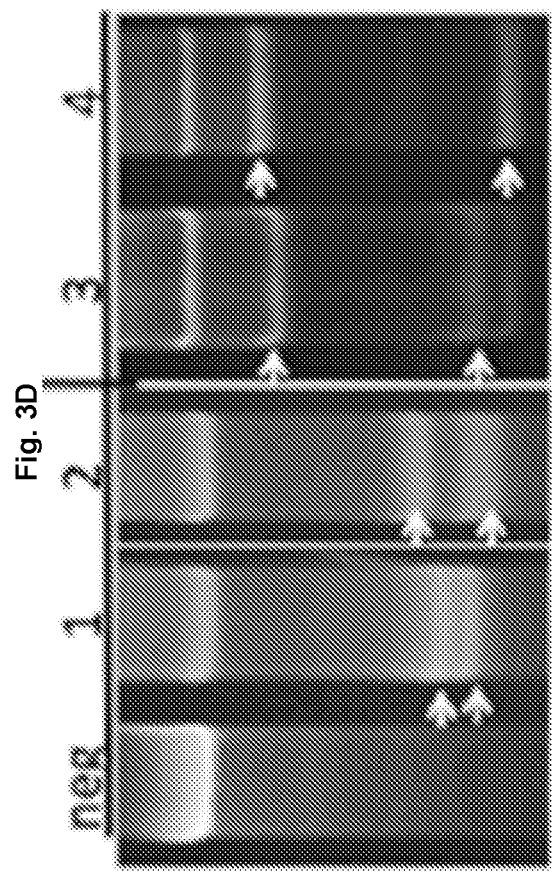

Using these parameters the use of CRISPR/Cas9 engineering of T-cells was pursued using the experimental schema as shown in FIG. 3A. Human primary T-cells were grown in the presence of IL-2 and activated with CD3/CD28 beads for 48-72 hours. The CRISPR/Cas9 reagents used a guide RNA transcript (Synthego) and recombinant Cas9 peptide (Aldevron) that were delivered using the Neon electroporation device (ThermoFisher). The individual candidates were located in exon 2 of NR3C1 and were identified through the MIT CRISPR Design Tool (FIG. 3B). Using the Surveyor nuclease assay to assess nuclease activity (FIG. 3C) all four candidates were observed to be active as evidenced by Surveyor DNA fragmentation products (FIG. 3D). The two candidates identified, termed GR1 and GR2, exhibited the highest activity levels (FIG. 3D).

Example 3: CRISPR/Cas9-Mediated NR3C1 Knockout in Tregs

To determine whether the GR1 and GR2 guides were also capable of knocking out the NR3C1 locus in cultures of clinically-relevant Tregs, banked Tregs were thawed and re-stimulated with anti-CD3/28 beads in high dose IL-2 (300 U/ml). On day 3, the Tregs were electroporated as above in the absence or presence of GR1 or GR2 GRISPR/Cas9 RNP and returned to culture in optimal expansion conditions. After 2 days, Treg cultures were harvested and were re-cultured±Dexamethasone (30 µg/ml) for an additional 48 hours (7 days total), at which time cultures were harvested, and relative survival was assessed by flow cytometry using a viability dye and counting beads. The dose of 30 µg/mL was identified by performing beta testing in Jurkat and primary T-cells that had undergone CRISPR/Cas9 gene modification and Dexamethasone dosing from 0-100 µg/mL. As shown in FIG. 4B, Tregs electroporated with GR2 CRISPR/Cas9 had significantly increased survival in the presence of Dexamethasone. CRISPR/Cas9 gene repair by non-homologous endjoining results in insertions and deletions (indel) proximal to the gRNA binding site. As such, the indel pattern using a sequence trace decomposition algorithm called TIDE (tracking of indels by decomposition) was assessed. Pre- and post-Dexamethasone exposure samples were analyzed (FIGS. 4C and 4D, respectively). The frequency of out of frame indels that are predicted to result in gene inactivation in Tregs prior to Dexamethasone addition was ~35%, which is similar to what was experimentally observed for peripheral blood T cells treated with GR2 GRISPR/Cas9 reagents (~40%). Following culture in Dexamethasone, the frequency of indels increased to 44%. Without being bound by any theory, this indicates preferential survival of gene modified Tregs. Cells that acquired Dexamethasone resistance also showed an enrichment of out of frame indels.

Example 4: Homology Directed Repair in Tregs

To achieve dual drug (steroid and calcineurin inhibitor) resistance, Jurkat and primary T-cells were used to define the conditions for optimal homology directed repair (HDR). Cas9 mRNA and Cas9 RNP approaches were compared and assessed for their ability to facilitate HDR using a reporter HDR construct at the human AAVS1 locus. In these studies, Cas9 RNP followed by immediate addition of an AAV viral donor template was observed to result in maximal (>65%) HDR rates). The HDR template was designed and is as shown in FIG. 5A, and contained the calcineurin resistance gene coexpressed with GFP and driven by the MND promoter. Flanking the calcineurin resistance gene were donor targeting arms homologous to the NR3C1 gene such that insertion disrupted exon 2 with concomitant deletion of 21 amino acids (FIG. 5A). To define the conditions for HDR in Tregs culture conditions that were optimal for AAV transduction (Treg density of $2 \times 10^6$ cells/ml) were employed. The donor was packaged in AAV-6 serotype viral particles and added to Tregs, at various multiplicities of infection (MOI) that had been electroporated with the GR2 gRNA and Cas9 protein. Using an inside-out PCR strategy with one PCR primer inside the donor and the other located outside the donor at the adjacent genomic locus HDR was observed in Tregs at each MOI (FIG. 5B). Sanger sequencing showed the junction of the donor arm with the endogenous locus (FIG. 5C).

Figure 6A:
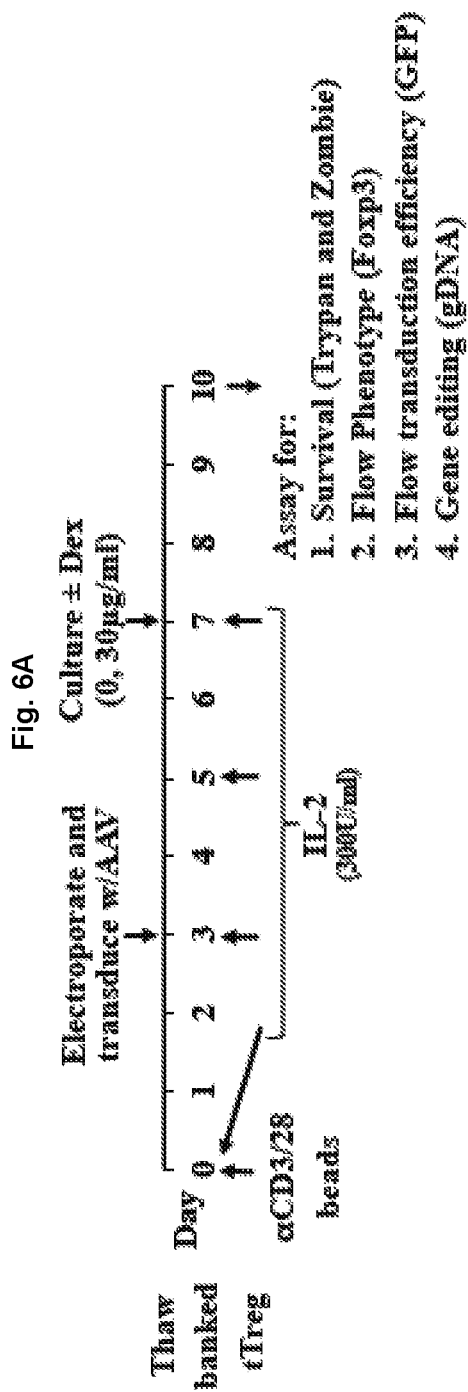
Figure 6B:
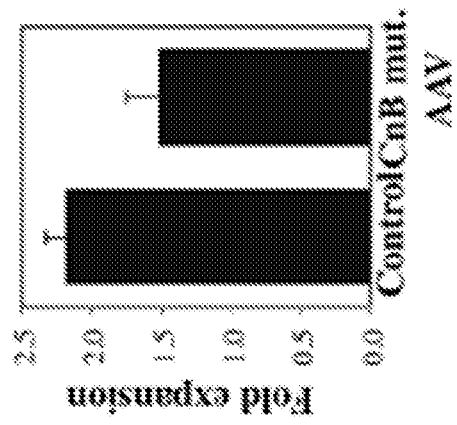
Figure 7A:
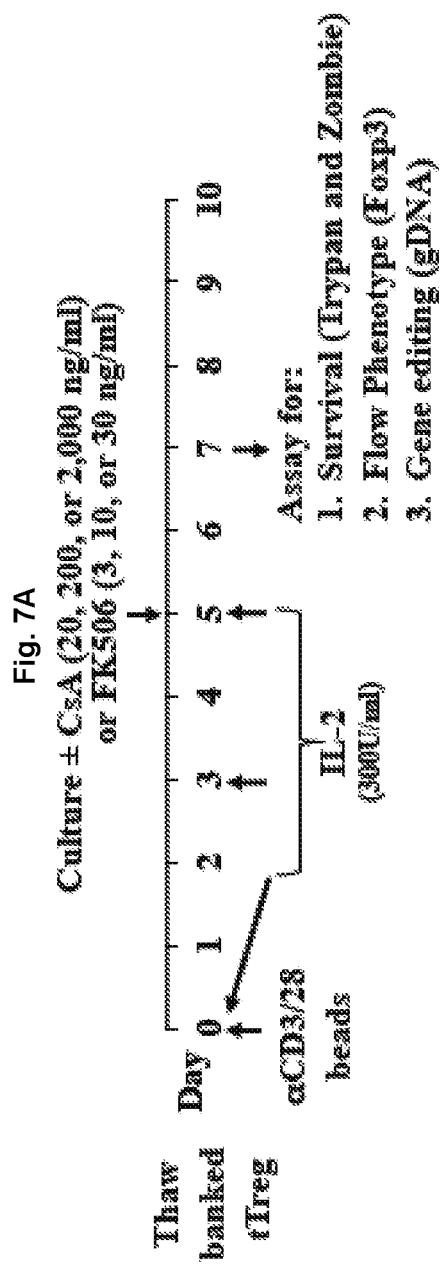
FIGS. 7A-7D depicts Treg drug susceptibility as related to IL-2 concentrations.
Figure 7B:
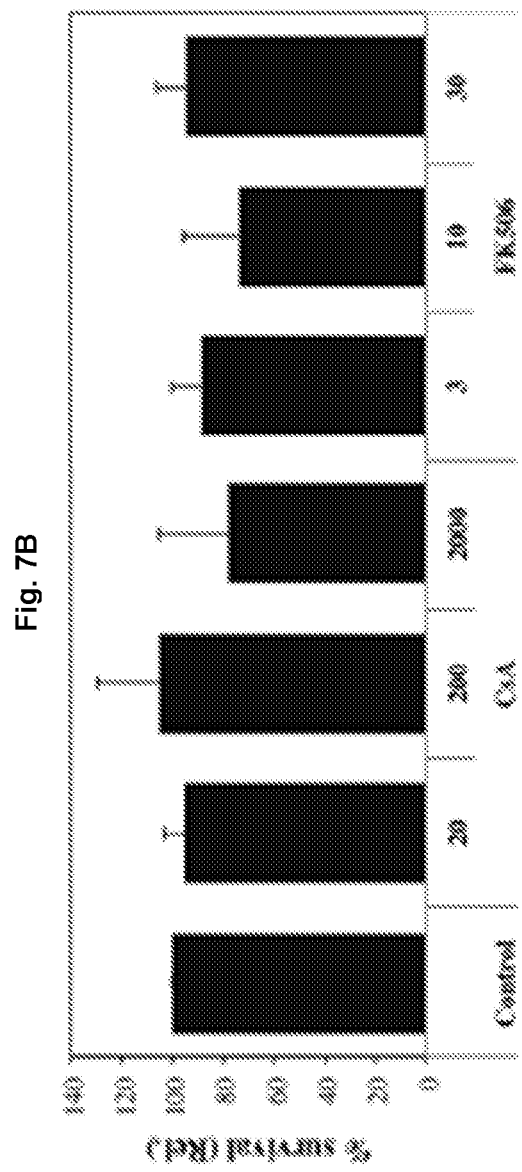
Figure 7C:
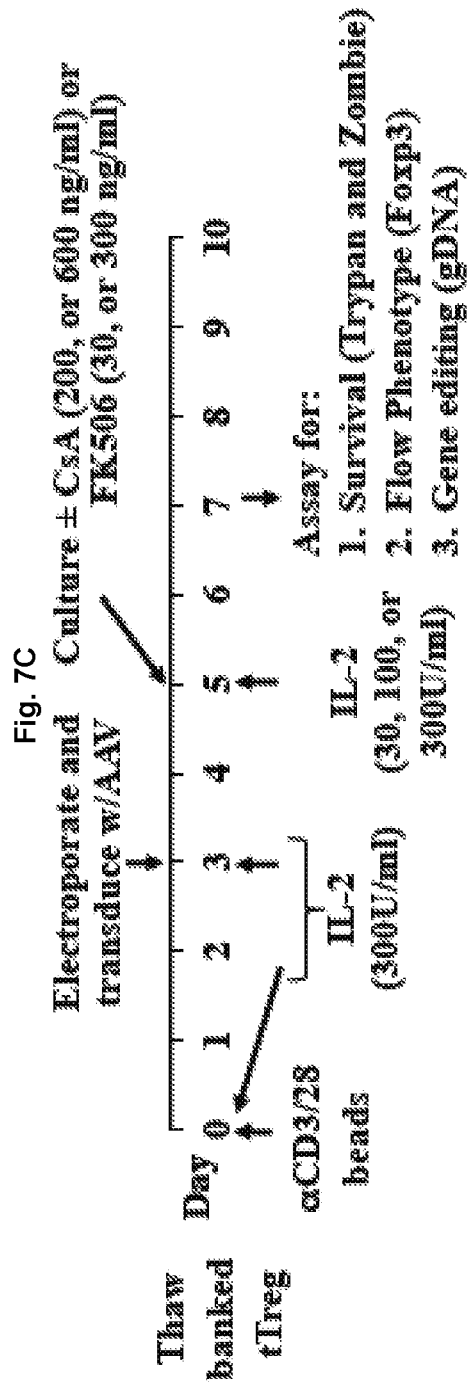
Figure 7D:
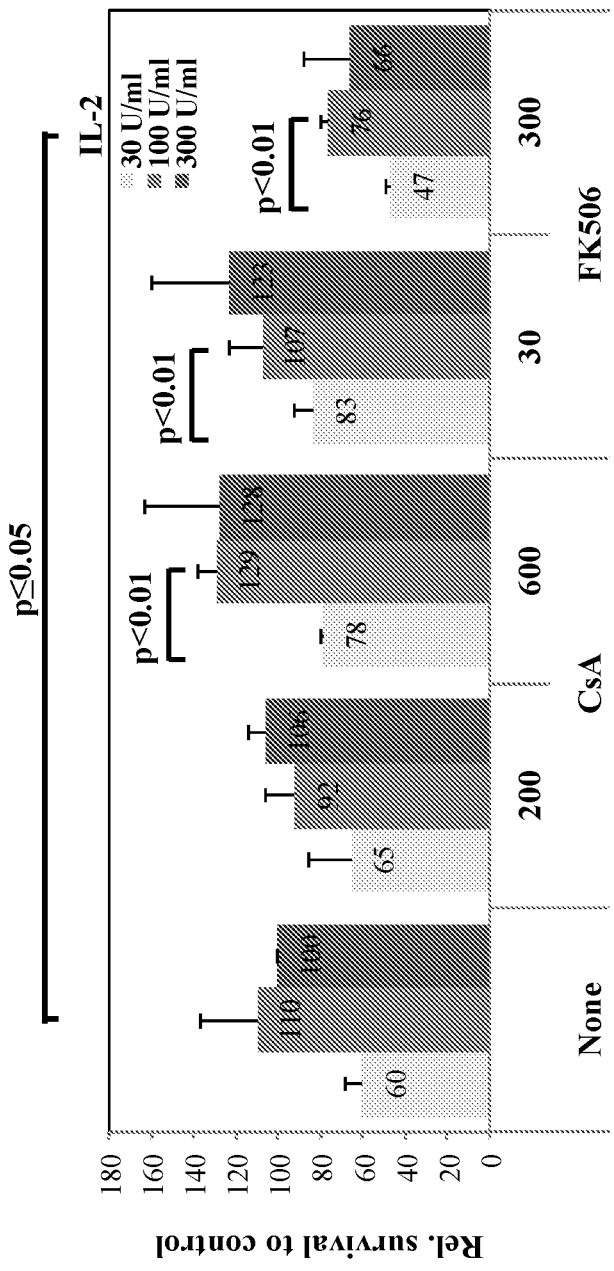

Example 5: HDR in Tregs Using GR2-Cas9 and AAV Under Optimal Treg Expansion Conditions To optimize HDR in a clinically relevant culture setting, banked Tregs were thawed, stimulated, expanded for 2 days, and then electroporated with GR2-Cas9. After electroporation, the cells were transduced with AAV at an MOI of $3 \times 10^5$, and returned to optimal Treg expansion conditions. Under these conditions, Treg expansion was not significantly affected following transduction (FIG. 6B) and GFP expression from the HDR donor was observed (FIG. 6C). The Treg population treated with GR2-Cas9 and CnB mut. AAV showed increased survival when cultured with Dexamethasone (FIG. 6D).

Example 5: Tregs of the Present Invention are not Susceptible to CsA or FK506 Toxicity at >3-Fold Peak Therapeutic Conditions To model the in vivo inhibitory effects of CNI on Treg survival and expansion, banked Tregs were thawed, re-stimulated, expanded for 4±1 days and treated with or without cyclosporine (20, 200, and 2000 ng/ml) or FK506 (3, 10, 30 ng/ml) for an additional 2-3 days and relative survival was assessed by flow cytometry. Studies were performed with non-separated Tregs, naïve Tregs and memory Tregs, to determine whether one subset was differentially sensitive to Dex and CNIs and to determine whether IL-2 dependency differences might permit lower IL-2 concentrations. No differences were found in outcome parameters the three populations.

FIG. 7 shows that, under these conditions, neither CsA or FK506 had a significant effect on Treg survival in vitro, even at concentrations >3-fold over peak therapeutic values. One of the primary targets of calcineurin, and thus CNIs, is the transcription factor NFAT, which is activated downstream of CD28 and is required for Treg development. IL-2 signaling can also activate NFAT. Without being bound by any theory, the lack of CsA and FK506 toxicity on Tregs in vitro may be due to the supra-physiological IL-2 concentrations in the culture. To test whether an effect could be revealed by decreasing the IL-2 concentration, thawed/re-stimulated Tregs were exposed to CsA or FK506 in titered concentrations of IL-2 for the final 3 days of culture and relative survival was assessed by flow cytometry.

Figure 8:
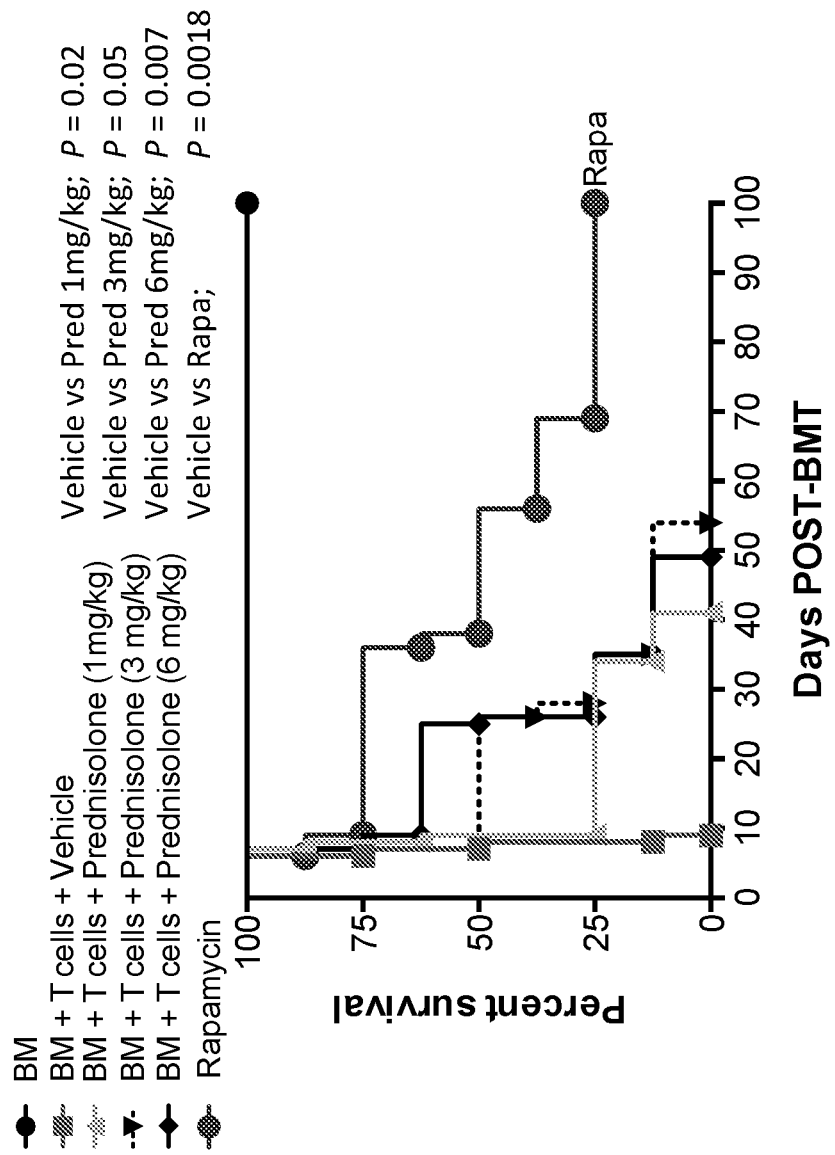
FIG. 8 depicts steroid dose responses for GVHD prophylaxis in allogeneic BMT recipients. n=8 per group. BALB/c mice were lethally irradiated, given B6 BM+2 M T cells and steroids at the indicated doses from day 1-28. A low rapamycin dose (day 0-14, 3 times a week through day 27) was used as a comparator. Each group was found to be significantly different than vehicle control.
Figure 9:
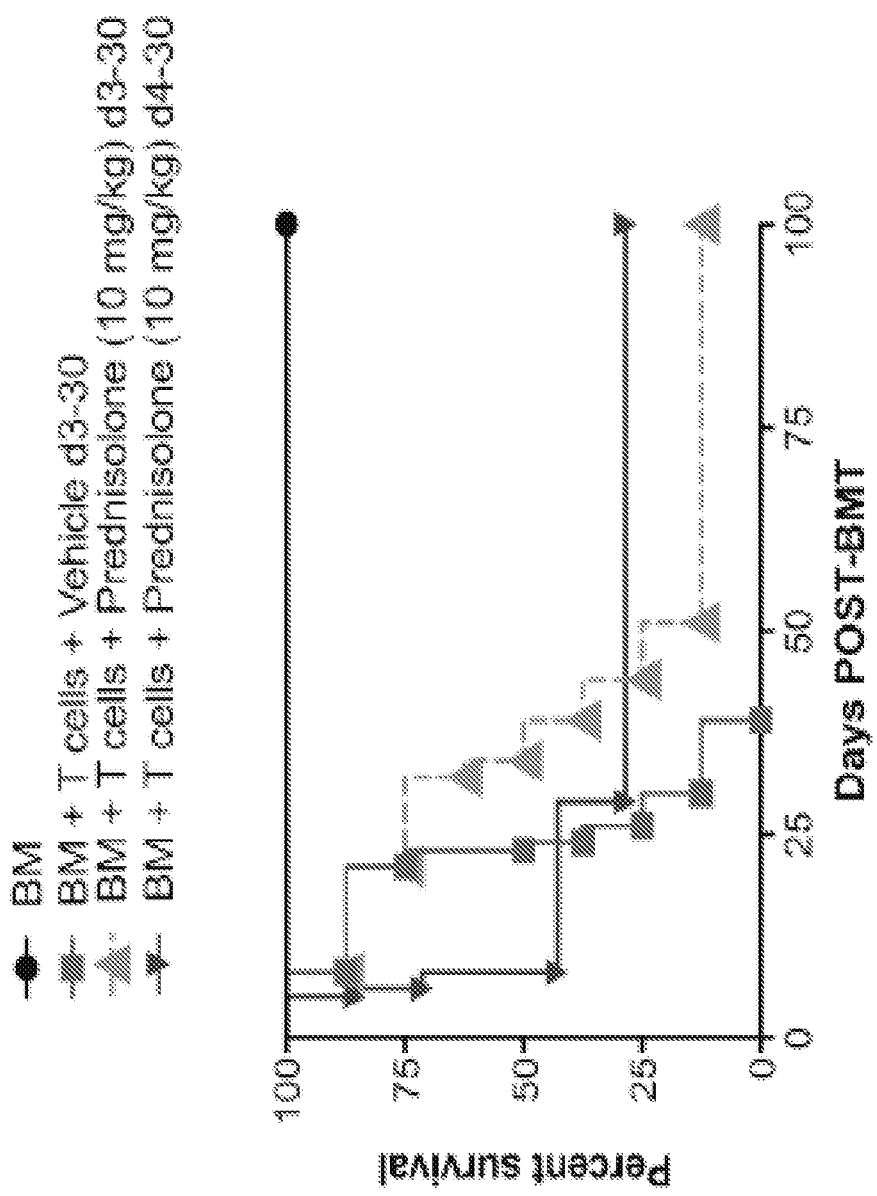
FIG. 9 depicts steroid based GVHD therapy in allogeneic BMT recipients. n=8 per group. BALB/c mice were lethally irradiated, given B6 BM+1.5 M T cells and steroids at 10 mg/kg/day day 3-28 or 4-28 as indicated. It was found that day 3 treatment was significantly better than vehicle control (p=0.03).

Example 6: Establishing Glucocorticoids and Calcineurin Inhibitor Platforms for In Vivo Models of GVHD to Verify that Gene Modification of Tregs Increases Efficacy in an Immunosuppressive Environment To test whether gene modified (GR2-CRISPR/Cas9) or gene edited (GR2-CRISPR/Cas9/AAV-CaN mut.) Tregs have increased efficacy in vivo in the presence of glucocorticoid, how glucocorticoid (methyl-prednisolone) effects GVHD in preclinical mouse models was first determined. An allogeneic GVHD model was used for several reasons: 1) optimal GVHD prophylactic doses of Csa (optimal 80 mg/kg/day vs. no benefits at 20 or 40 mg/kg/day) and FK506 [36 mg/kg/day in carboxymethylcellulose (55%-90% day 100 survival vs. 0% by day 37 with vehicle] with some toxicity at 48 mg/kg/day and poorer efficacy at 12 or 24 mg/kg/day in aqueous solution; n=16-26/group) were established; 2) optimal Treg generation and expansion protocols that lead to GVHD prevention in >90% of mice and further titered Treg doses to determine the threshold Treg: Teffector ratios that were too low to uniformly prevent GVHD (0.75:1 was deemed suboptimal; 0.5:1 provided protection at a level of <50% longterm survival) were established; and 3) allogeneic GVHD models are highly amenable to GVHD pathophysiological studies including Treg and Teffector trafficking, persistence, and function, facilitating in depth Treg and Teffector studies. For these reasons, as well as the more logistically feasible and cost effective benefits of an allogeneic GVHD model, optimized steroid use in allogeneic recipients for GVHD prevention and therapy were first tested, and then applied to a xenogeneic model to enable testing of the human Treg product. Using lethally irradiated BALB/c recipients of C57BL/6 (B6) donor bone marrow+ $2 \times 10^6$ T cells, methyl-prednisolone at doses of 1, 3, and 6 mg/kg/dose were tested days 1-28 vs. rapamycin at 0.5 mg/kg/day, days 0-14 then 3×/week through day 27. Survival and p values are shown in FIG. 8. The T cell dose was reduced to $1.5 \times 10^6$ and moved to GVHD therapy beginning on day 3 or day 4 (rather than day 1 prophylaxis) and compared no treatment to vehicle to prednisolone (n=8/group). Day 3 GVHD therapy with prednisolone improved outcome (FIG. 9).

Delaying prednisolone treatment until day 4 was ineffective. Next, an experiment was performed to determine whether prednisolone at 10 mg/kg d3-28 was reproducible, and it was observed that this was the case (FIG. 10).

These data provide a steroid treatment model of GVHD in which steroids can rescue a proportion of mice but is not curative, providing a forum for testing the addition of Tregs that are steroid resistant or sensitive.

Figure 11C:
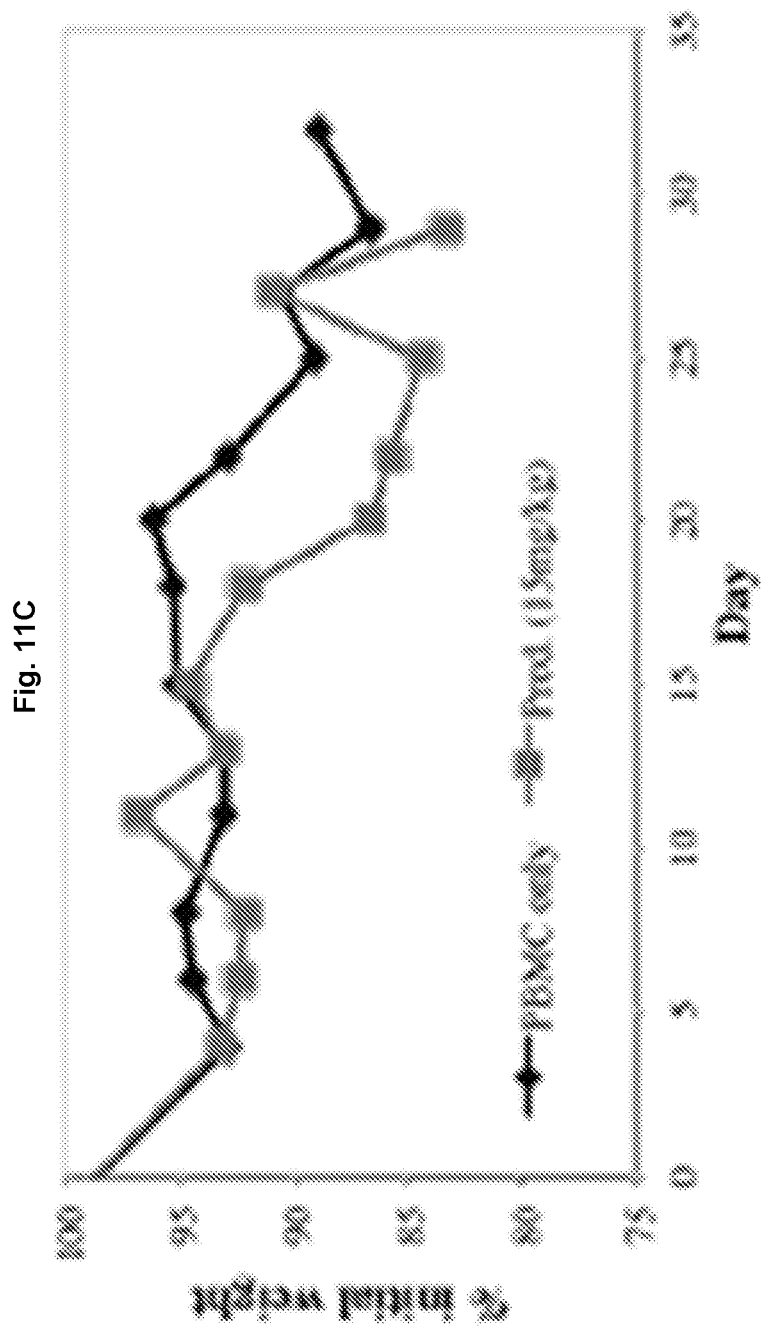
Figure 11D:
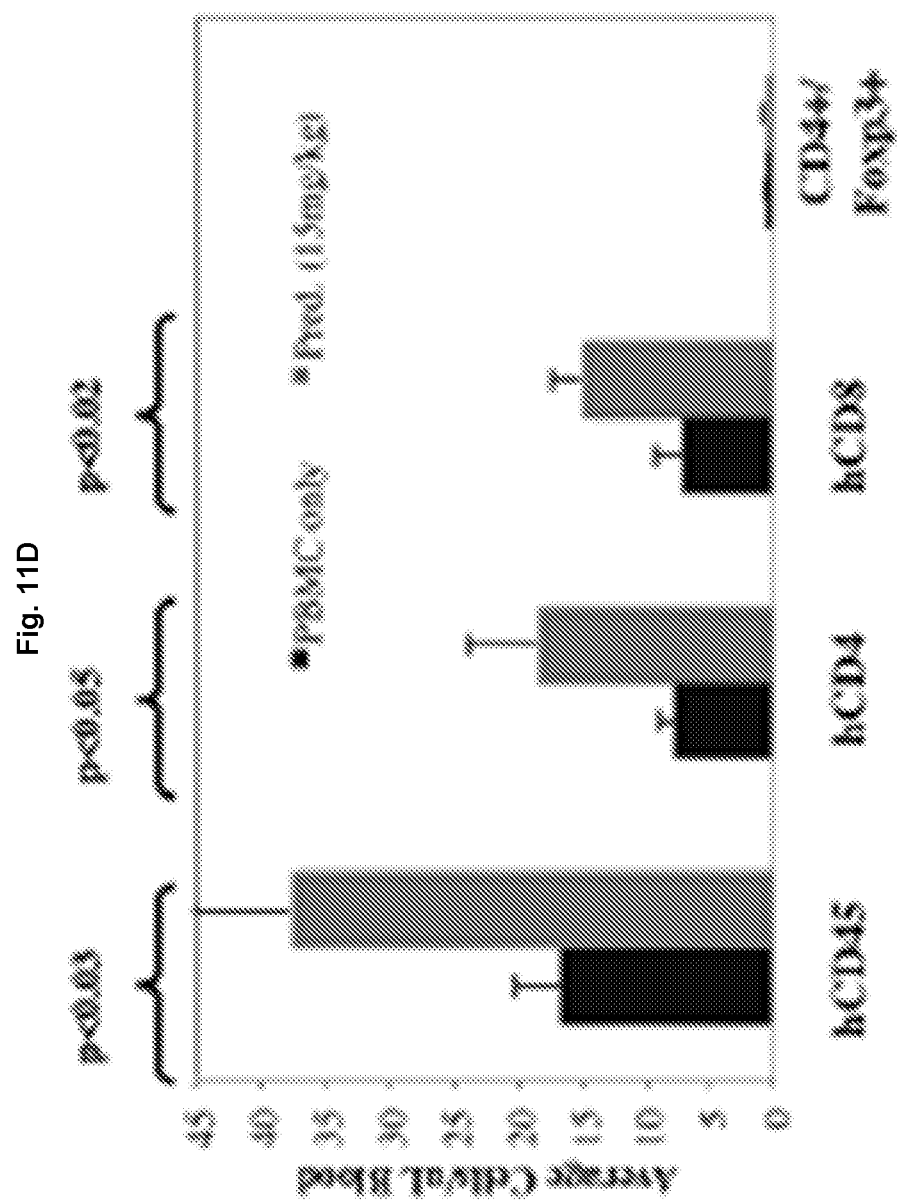

Example 7: Establishing Steroid and Calcineurin Inhibitor Based GVHD Prophylaxis and Treatment Regimens in a Xenogenic GVHD Model To determine the optimal doses of prednisolone, Csa and FK506, non-lethally irradiated (50 rad), immunodeficient NOD/Scid/IL-2Rg-/-(NSG) mice were given $15 \times 10^6$ human peripheral blood mononuclear cells (PBMCs). Outlined in FIG. 11A, mice were given a high dose of prednisolone (30 mg/kg, day 0-28) since only incomplete GVHD prevention was seen at 10 mg/kg in the allogeneic GVHD model (per FIGS. 8-10). This dose/schedule of prednisolone did not offer a survival advantage, and treated mice had a lower median survival (25 vs. 29 days), although the difference was not significant (FIG. 11B). In addition to survival, weight loss and human T cell expansion have been shown to be markers of disease severity in this xeno-GVHD model. In this experiment, the average weight of prednisolone treated were not significantly different than controls (FIG. 11C). These mice did have significantly more human CD4+ and CD8+ T cells in the blood on day 19 (FIG. 11D).

Figure 12A:
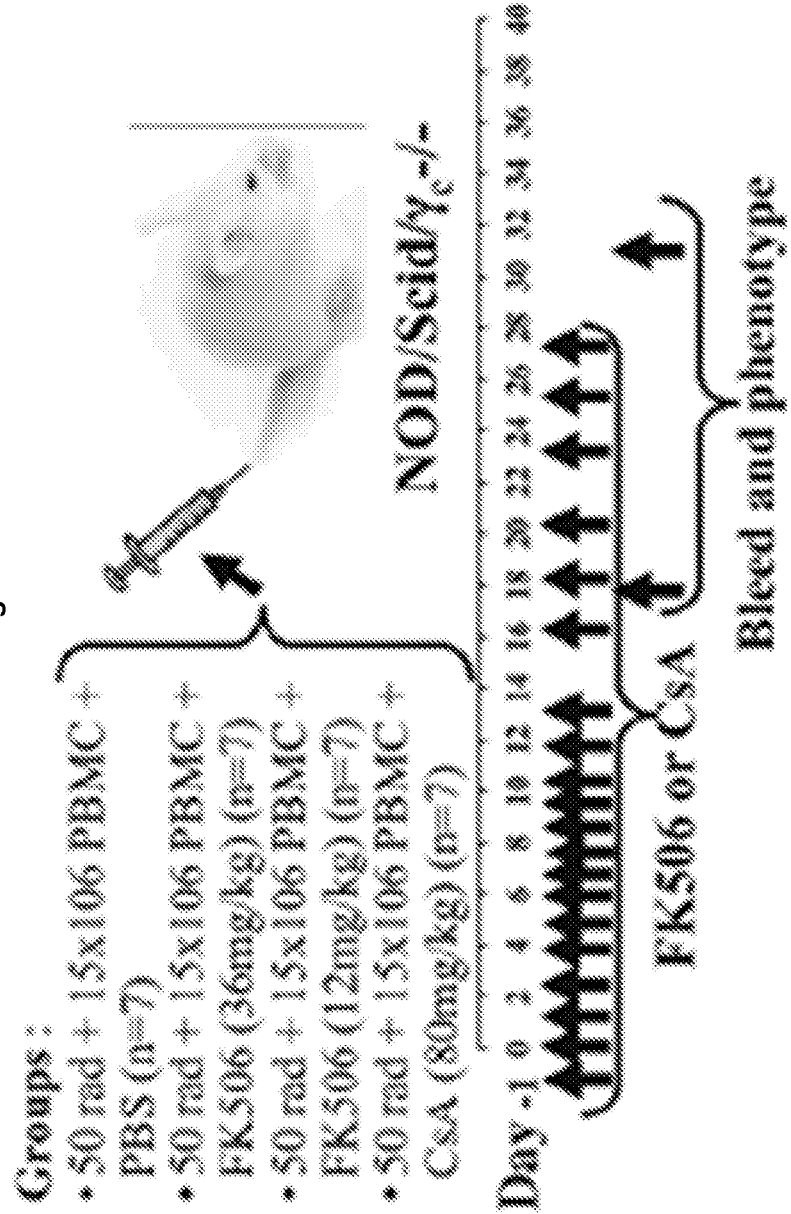
Figure 12B:
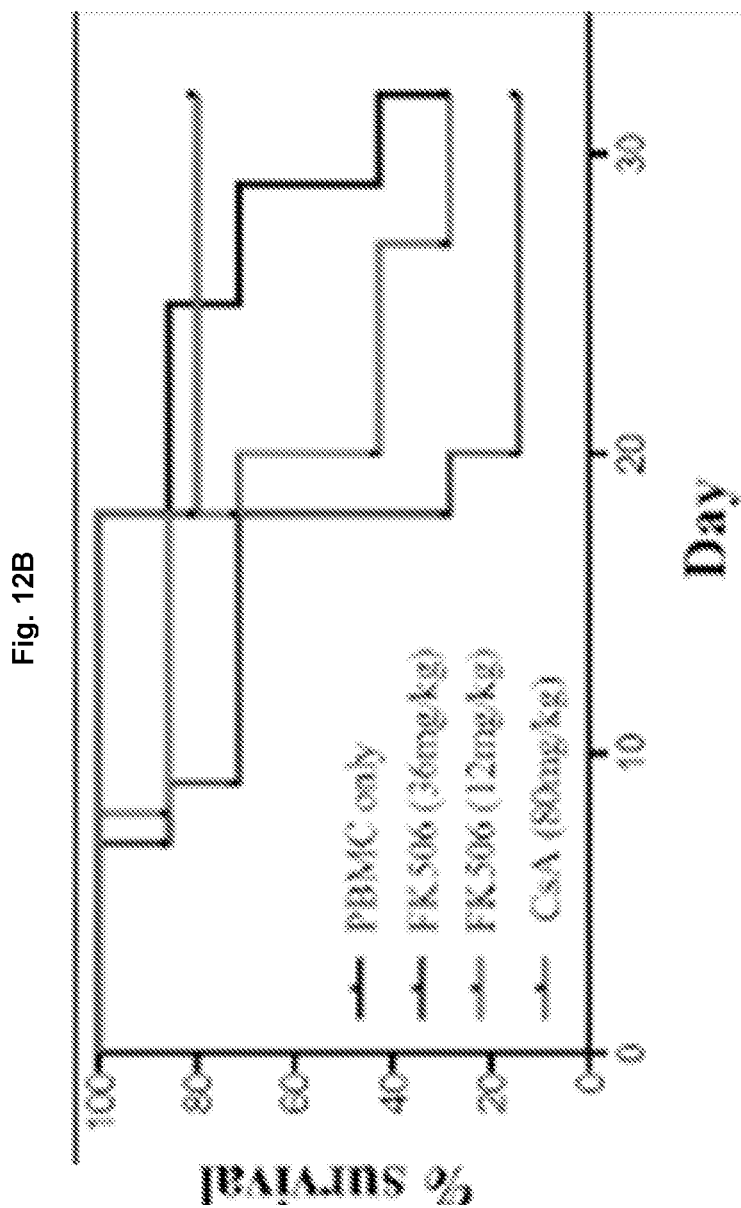
Figure 12C:
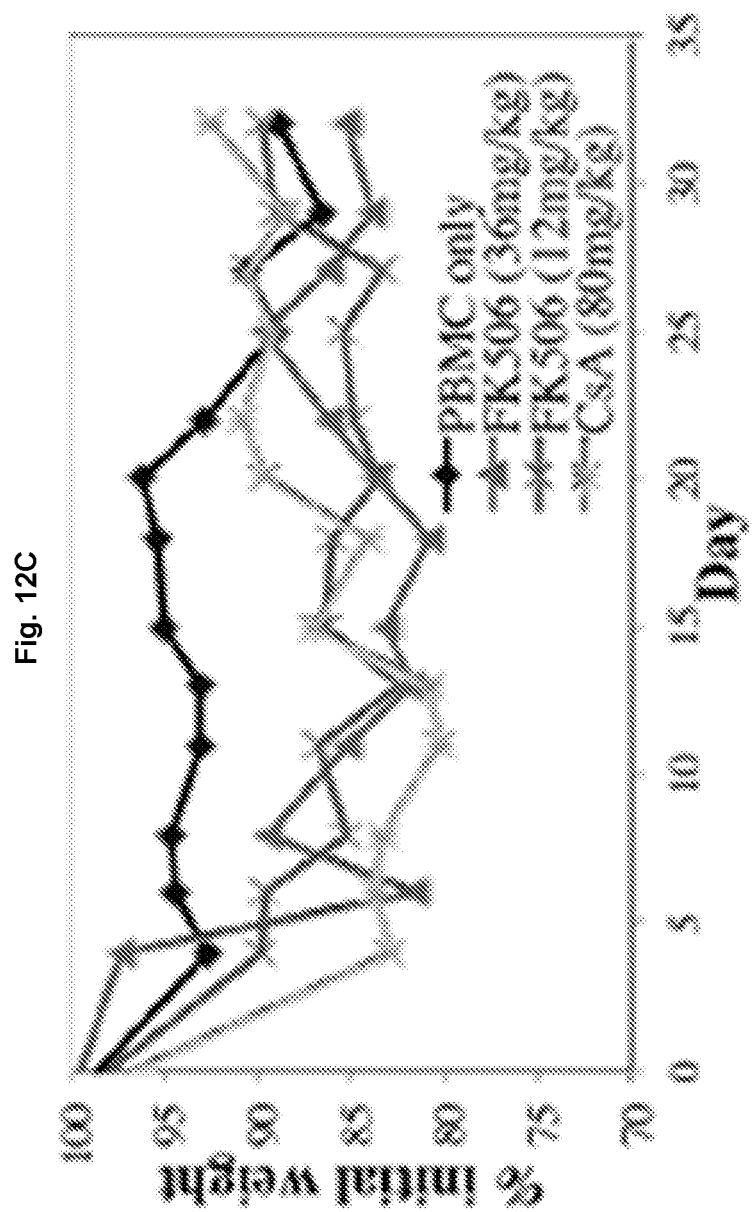
Figure 13:
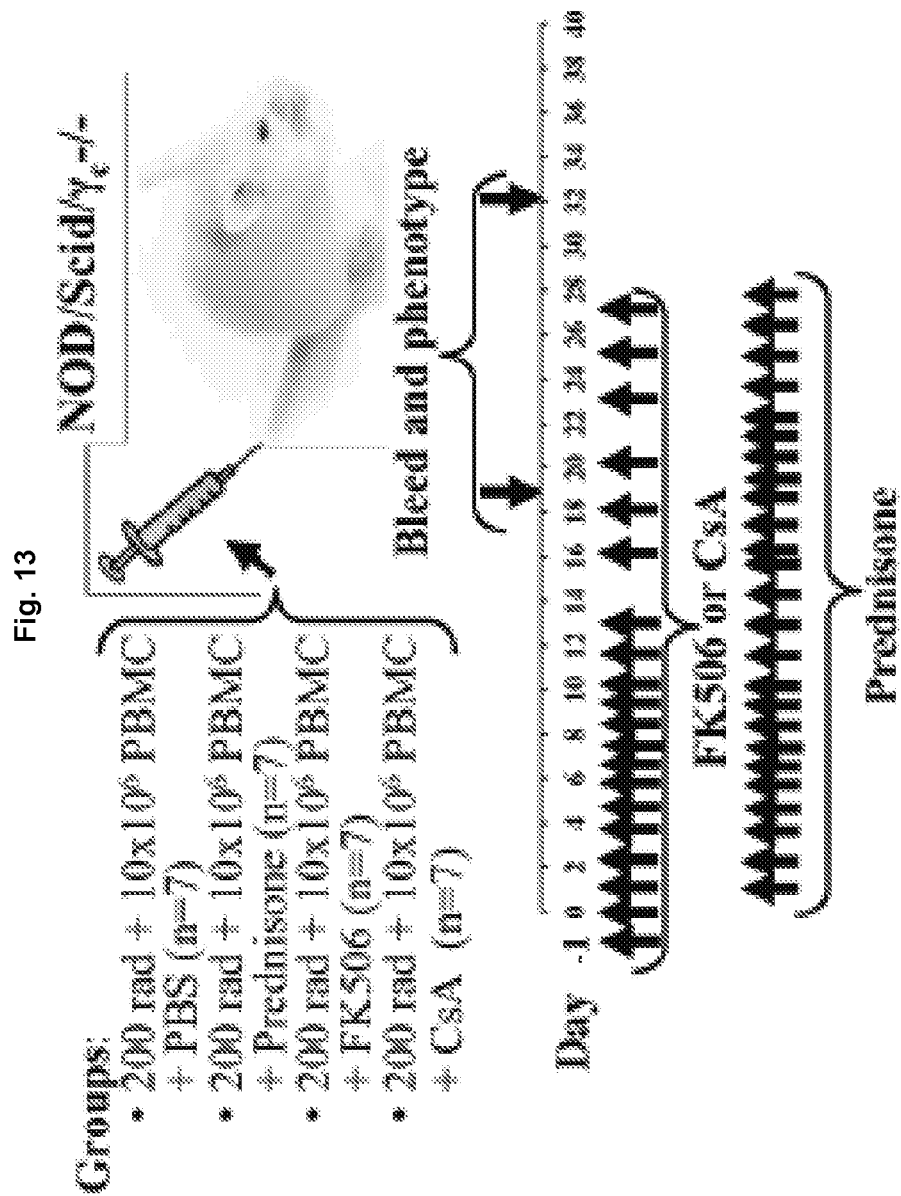
FIG. 13 depicts a schematic illustration indicating cohorts (n=7 mice), dosing schedule, and analysis points. Human PBMC ($15 \times 10^6$) were injected into irradiated (50 rad) NSG mice±prednisolone (10 mg/kg), FK506 (12 mg/kg) or CsA (20 mg/kg), and signs of GVHD (including survival, weight, clinical score, and human T cell expansion) were monitored.

To assess the effect of CNI on the xeno-GVHD model, mice were dosed with human PBMC as normal, and were given FK506 at 2 doses (36 or 12 mg/kg) or CsA (80 mg/kg) (FIG. 12A). Mice receiving high dose FK506 had significantly decreased survival (p<0.03), and while mice receiving 12 mg/kg FK506 had a lower median survival (20 vs. 29 days), the survival was not significantly different (FIG. 12B; P=0.45). The trend for mice receiving CsA was increased survival (currently P=0.15). Both FK506 and CsA resulted in significant early weight loss (FIG. 12C). Both FK506 and CsA significantly reduced the in vivo expansion of human CD45+, CD4+ and CD8+ cells (FIG. 12D; p<0.05 for each CNI cohort and each cell type vs. PBMC only control animals). A follow up study has shown that xeno-GVHD pathology induced with 200 rad+$1 \times 10^7$ human PBMC is more reproducible, and median survival is reduced from ~25 days to ~20 days. To assess the effect of a lower dose of prednisone and CNI in this modified xeno-GVHD model, mice were irradiated (200rad), injected with human PBMC (iv, $1 \times 10^7$), and were given prednisone (ip, 10 mg/kg), FK506 or CsA (ip, 2 mg/kg or 20 mg/kg, respectively) (FIG. 13).

Example 8: Characterization of Gene Edited Tregs

Since depletion of the stimulatory CD3/28 beads is required prior to electroporation, it was assessed whether this would have a negative effect on expansion. In vitro expanded, naïve Tregs were thawed and re-stimulated with CD3/28 beads (3:1 bead: Tregs), and on day 3 the sample was split and beads were depleted magnetically from one sample. Following bead depletion, Tregs were returned to culture for another 4 days (7 days total). As shown in FIG. 14, no significant effect on expansion (n=5) was found after the various manipulations as indicated.

Since Tregs are especially sensitive to extracellular DNA, and electroporation can lead to necrotic cell death and release of DNA, it was tested whether electroporation would affect Treg expansion. in vitro expanded naïve Tregs were thawed and restimulated with CD3/28 beads (3:1 bead: Tregs). On day 3, beads were depleted magnetically, and Tregs were treated electroporation, after which the cells were returned to culture for another 4 days (7 days total). Electroporation was found to have no significant effect on expansion (FIG. 14B). As a marker for electroporation efficacy, a sample of Tregs was electroporated in the presence of in vitro transcribed GFP mRNA. Not only was the mRNA well tolerated, but GFP was uniformly expressed at high levels in all cells, and expression persisted for at least 7 days after transduction (FIGS. 14C and 14D).

Example 9: Base Editing in Tregs

Treg cells were base edited by electroporation of the base editor as protein or mRNA encoding said base editor, along with a guide RNA to target bases for editing with said base editor. The genomic DNA of the edited cells was then isolated and the target locus was PCR amplified. The PCR amplified locus was then sequenced by Sanger sequencing. Base conversion was observed by identifying multiple peaks at the target site. The PCR amplicon sequence data then underwent decomposition using the EDITR method to quantify base editing frequency (see, Kluesner et al. "EditR: A novel base editing quantification software using Sanger sequencing".DOI: 10.1101/213496.2017). For FIGS. 19-22, and 24-27, the base edited sequences are marked by red open boxes.

Figure 16:
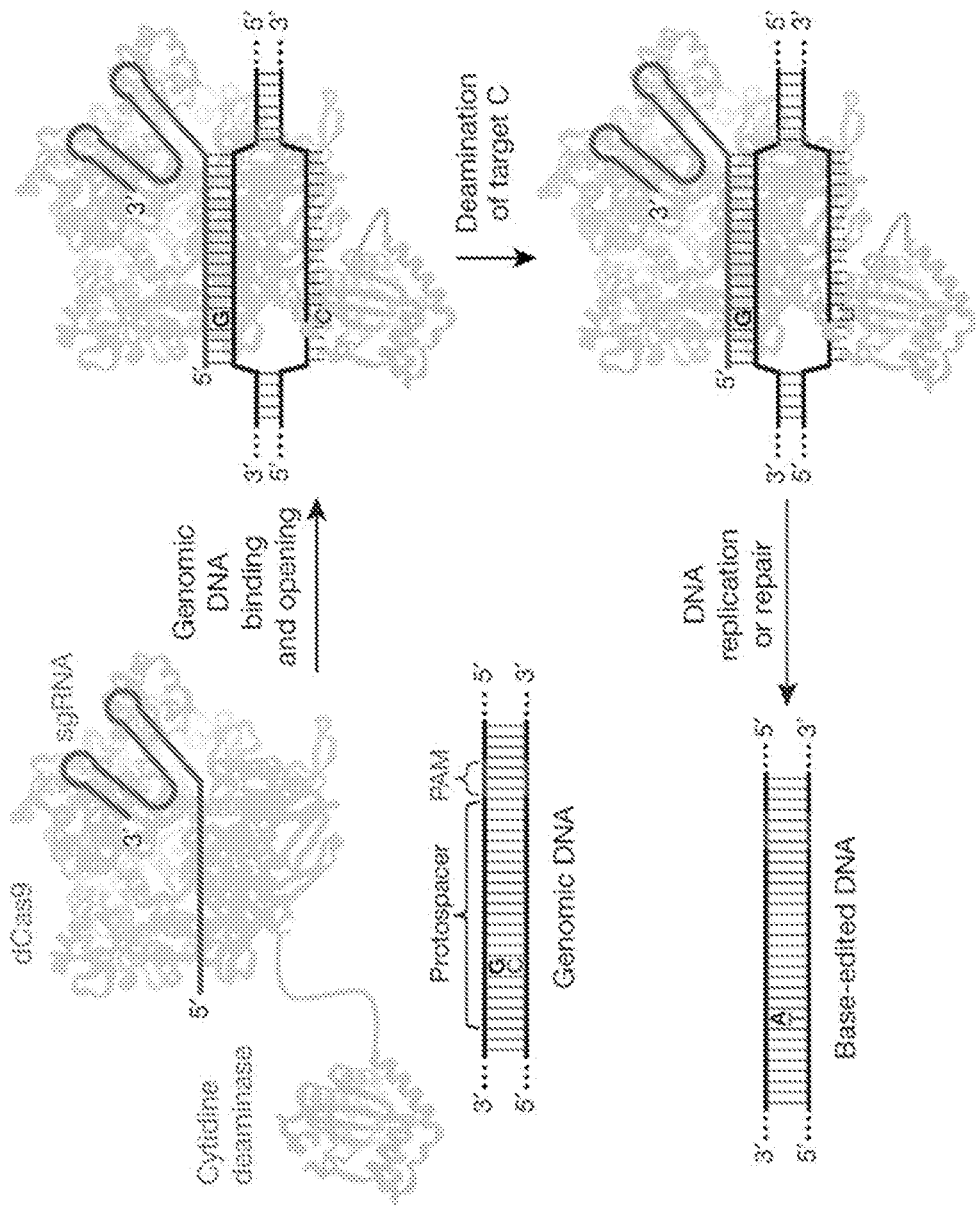
FIG. 16 depicts a schematic showing the base editor platform that is a Cas9-deaminase fusion gene/peptide capable of introduction of a substitution and a general schema of targeting strategies and molecular analysis and quantification using a method of the present disclosure.
Figure 17:
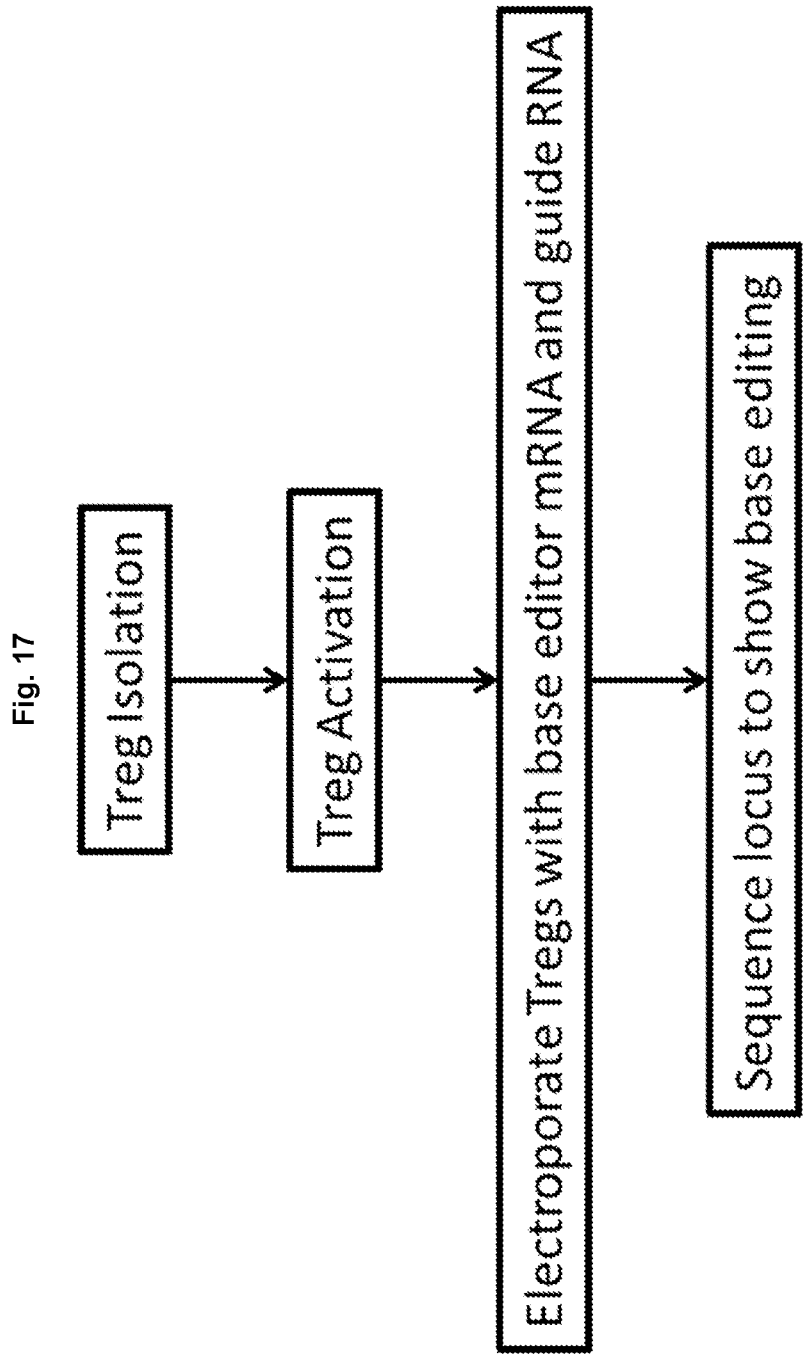
FIG. 17 depicts a flow diagram showing the general steps of achieving base-editing in Tregs.

FIG. 16 depicts a schematic showing base editing wherein the CRISPR deactivated or nicking DNA binding domain is a dCas9, and the base-editing domain is a cytidine deaminase. Base editing was performed in isolated Tregs according to the flow diagram shown in FIG. 17. Base editors can be delivered as RNP complexes whereby the guide RNA may or may not be modified with phosphorothioate bonds to prevent intracellular degradation by endogenous RNAses. For the present application the base editor was delivered as messenger RNA and the guide RNAs were synthesized to contain 5' and 3' phosphorothioate bonds to prevent intracellular degradation. The base editing targeting design was intended/designed to convert a nucleotide such that a premature stop codon was introduced. Further, the sequences at exon:intron boundaries defined as splice donors and acceptors that are required for intron excision and proper open reading frame orientation and expression were also targeted for conversion in order to disrupt splicing. Improperly spliced RNA with intron retention destabilizes the RNA leading degradation and loss of protein expression.

Figure 18:
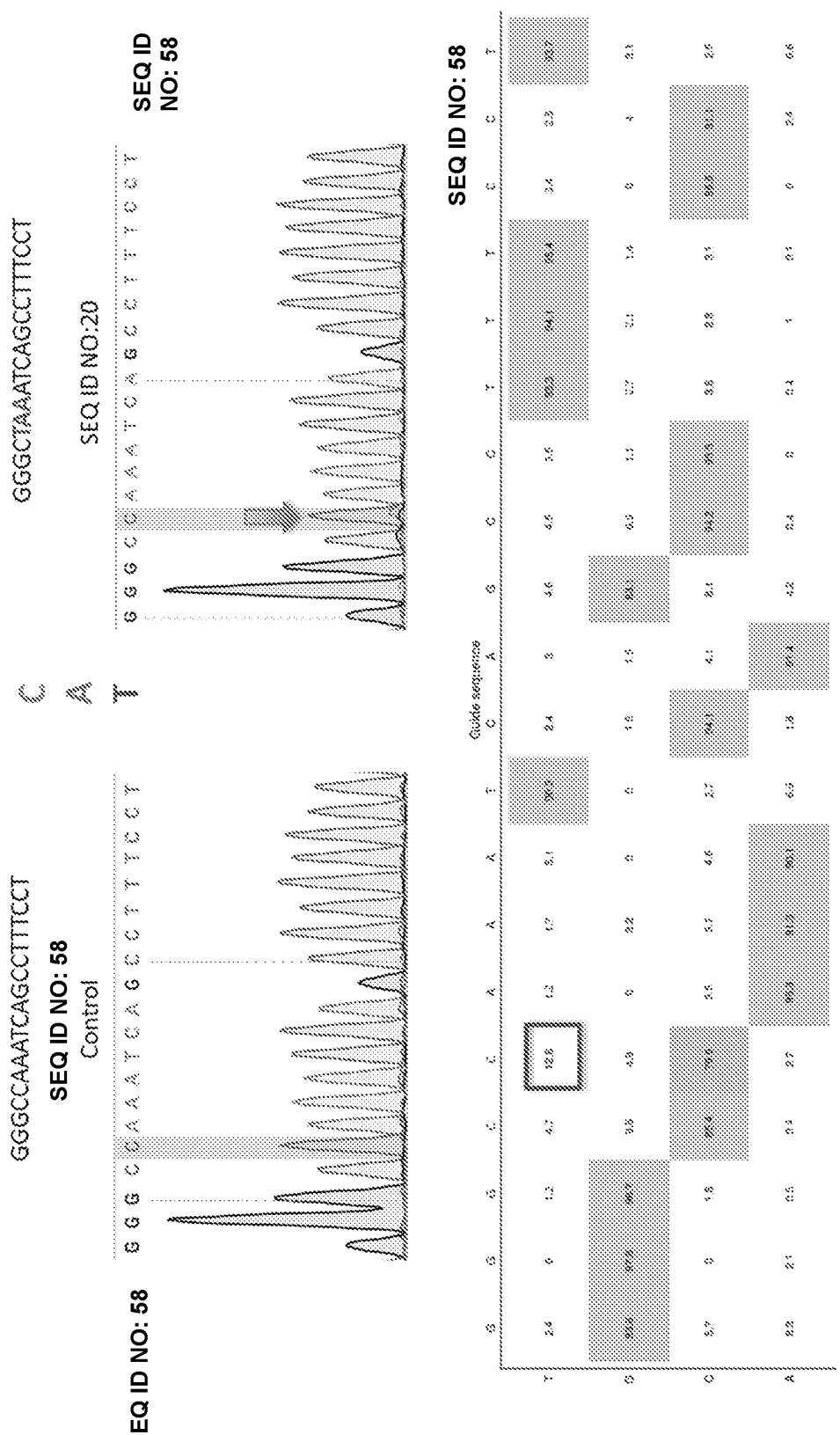
FIG. 18 depicts genomic sequencing data of control cells and cells electroporated with a gRNA (SEQ ID NO:20) designed to introduce a premature stop codon into NR3C1. The percent occurrence of a T, G, C, or A nucleotide at each position in the genome corresponding to the gRNA is shown.
Figure 19:
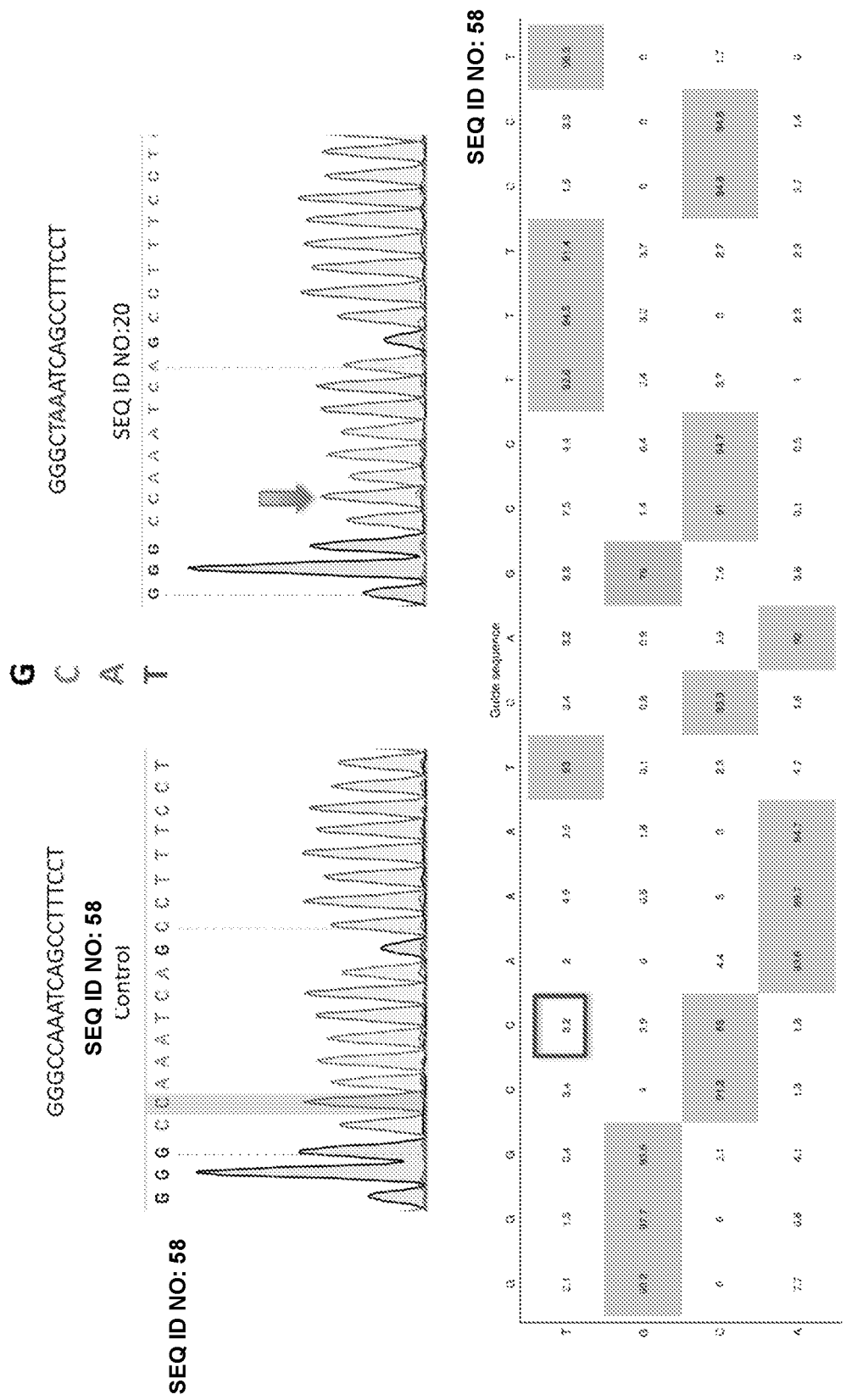
FIG. 19 depicts genomic sequencing data of control cells and cells electroporated with a gRNA (SEQ ID NO:20) designed to introduce a premature stop codon into NR3C1. The percent occurrence of a T, G, C, or A nucleotide at each position in the genome corresponding to the gRNA is shown.

Base editing was performed to introduce a premature stop codon in exon 2 of NR3C1. Electroporation of Tregs with base editor mRNA and a guide RNA having a sequence set forth in SEQ ID NO:7 was performed. Sequencing of the genetic locus revealed that base editing resulted in editing of a cytosine (C) in the genomic sequence into a thymine (T), thereby resulting in a premature TAA stop codon (FIGS. 18 and 19).

Figure 20:
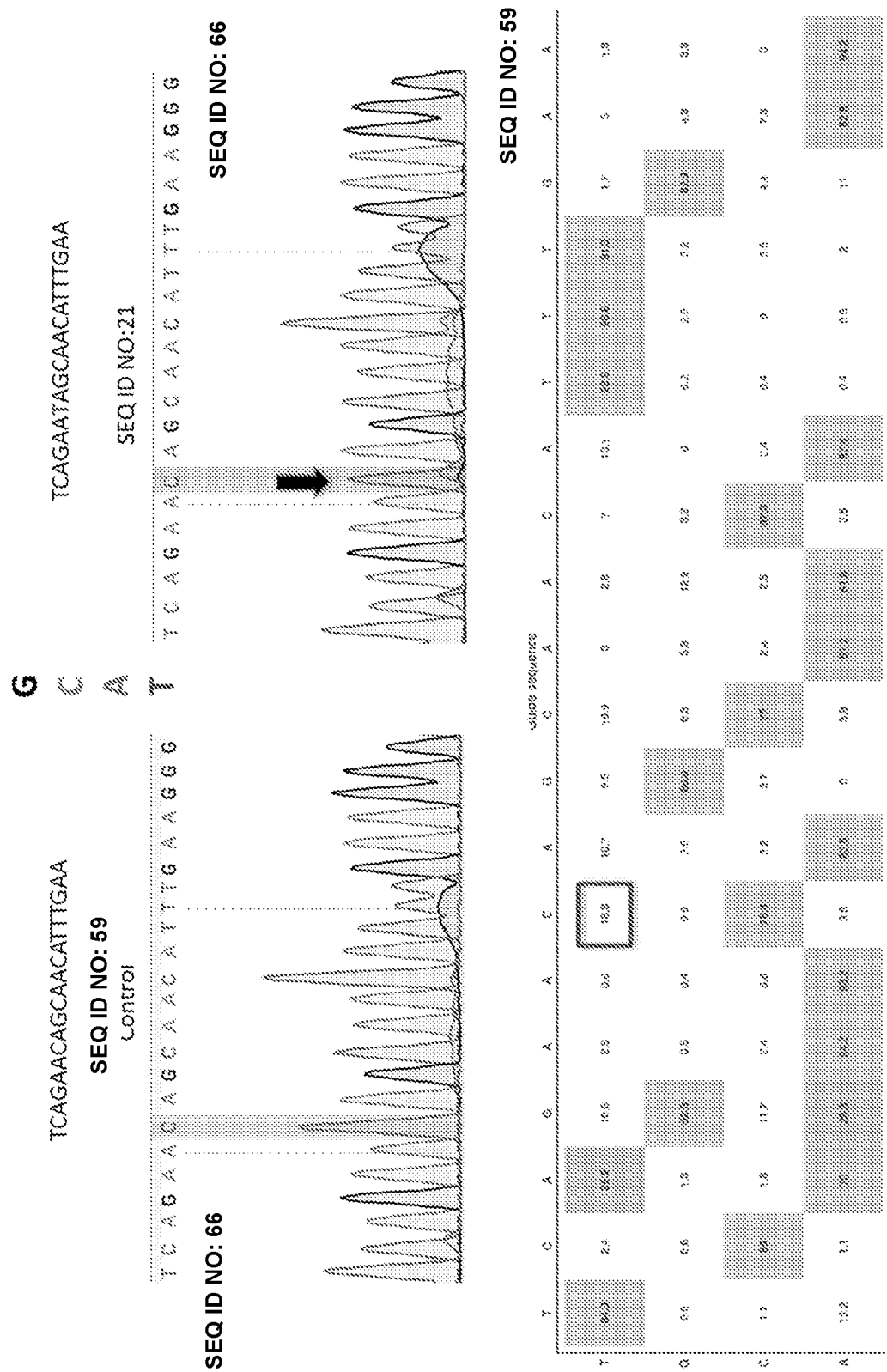
FIG. 20 depicts genomic sequencing data of control cells and cells electroporated with a gRNA (SEQ ID NO:21) designed to introduce a premature stop codon into NR3C1 The percent occurrence of a T, G, C, or A nucleotide at each position in the genome corresponding to the gRNA is shown.
Figure 21:
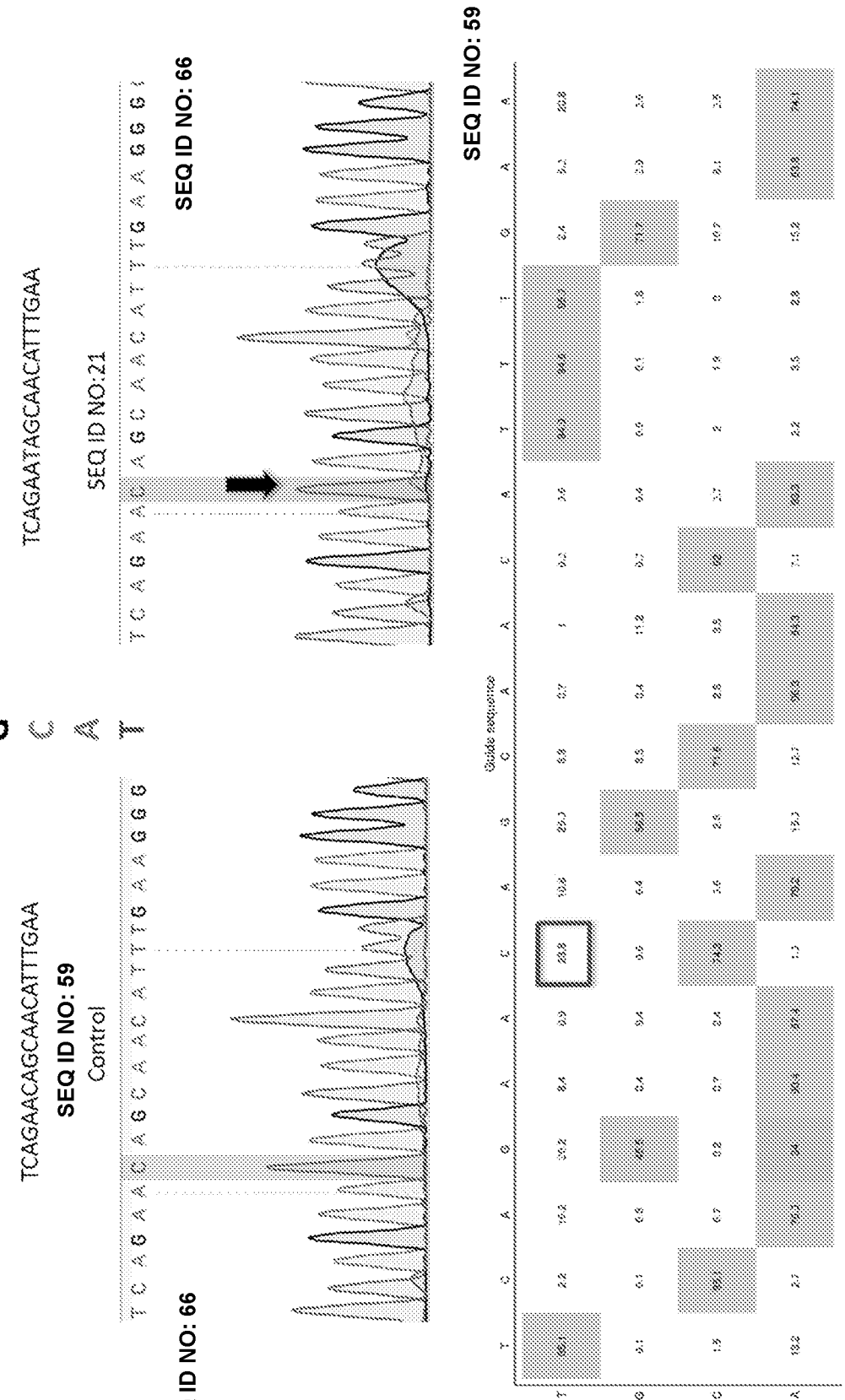
FIG. 21 depicts genomic sequencing data of control cells and cells electroporated with a gRNA (SEQ ID NO:21) designed to introduce a premature stop codon into NR3C1. The percent occurrence of a T, G, C, or A nucleotide at each position in the genome corresponding to the gRNA is shown.

Base editing was performed to introduce a premature stop codon in exon 2 of NR3C1. Electroporation of Tregs with base editor mRNA and a guide RNA having a sequence set forth in SEQ ID NO:8 was performed. Sequencing of the genetic locus revealed that base editing resulted in editing of a cytosine (C) in the genomic sequence into a thymine (T), thereby resulting in a premature TAG stop codon (FIGS. 20 and 21).

Figure 22:
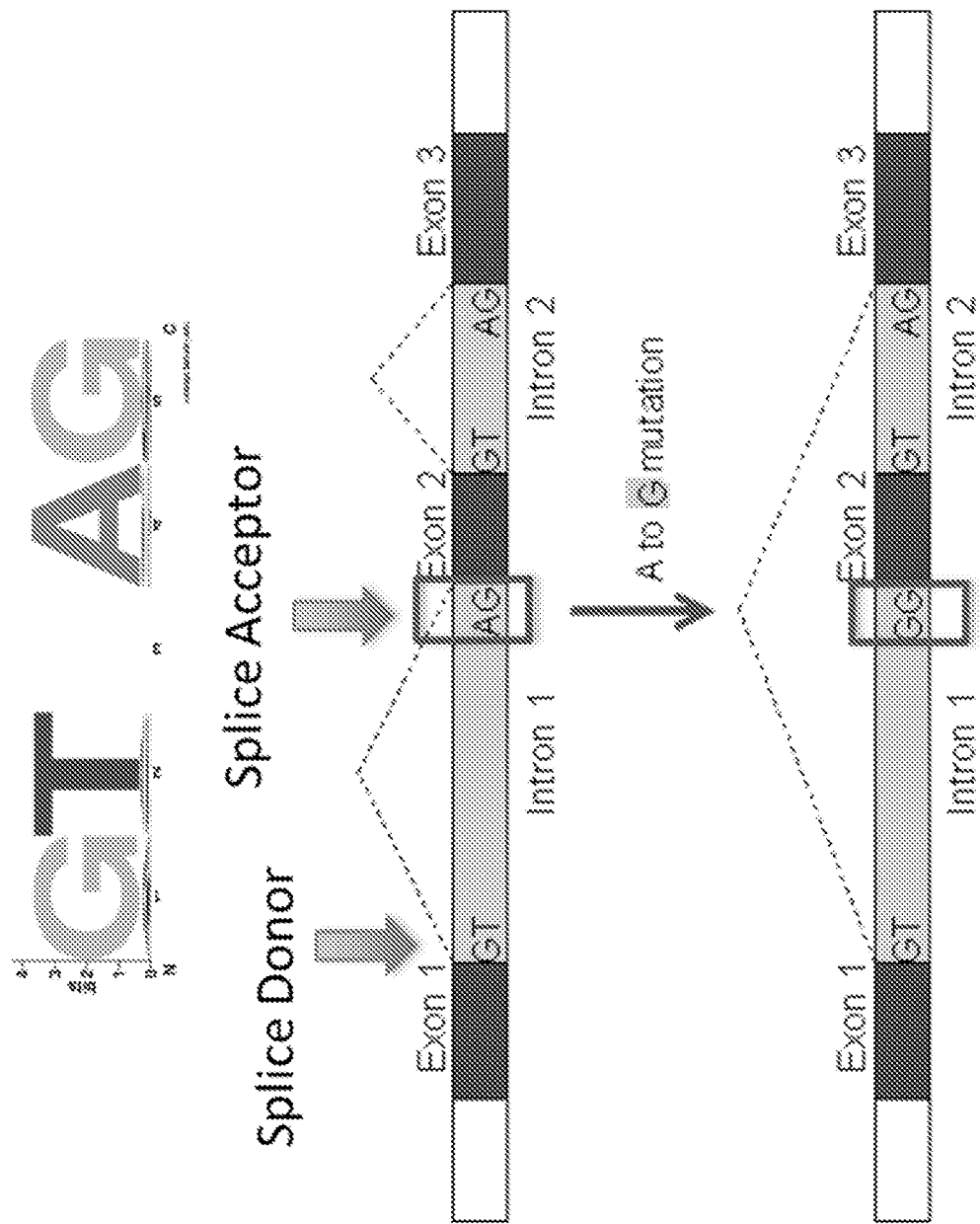
FIG. 22 depicts a schematic showing the introduction of a substitution into a splice site using a method of the present disclosure.

FIG. 22 depicts a schematic of the result of disrupting the splice site of a hypothetical gene. Base editing of either a splice donor or a splice acceptor site can disrupt the normal splicing of a gene, resulting in downregulated gene expression.

Figure 23:
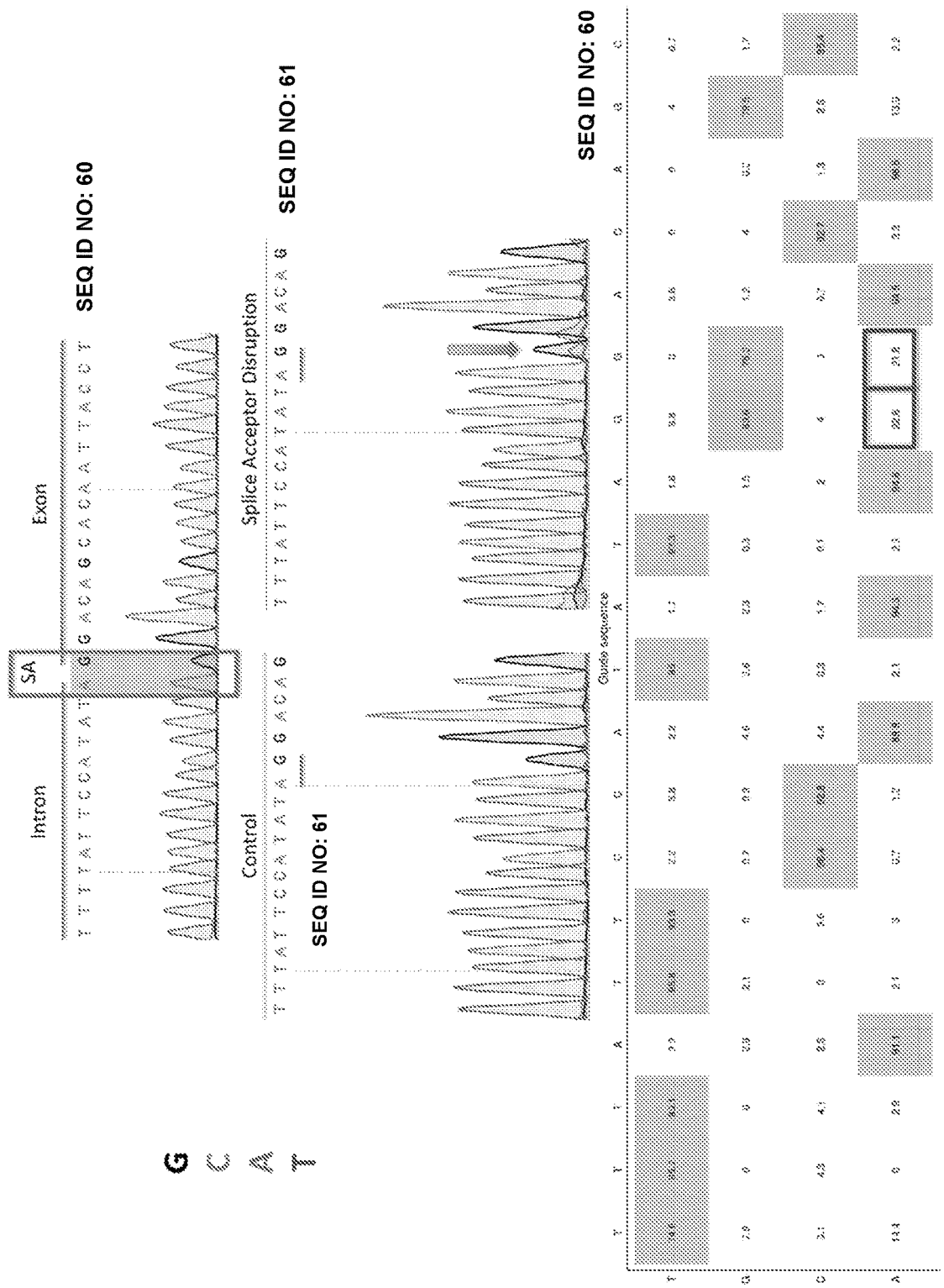
FIG. 23 depicts genomic sequencing data of control cells and cells electroporated with a gRNA (SEQ ID NO:55) designed to introduce a modification into a splice acceptor of NR3C1. The percent occurrence of a T, G, C, or A nucleotide at each position in the genome corresponding to the gRNA is shown.
Figure 24:
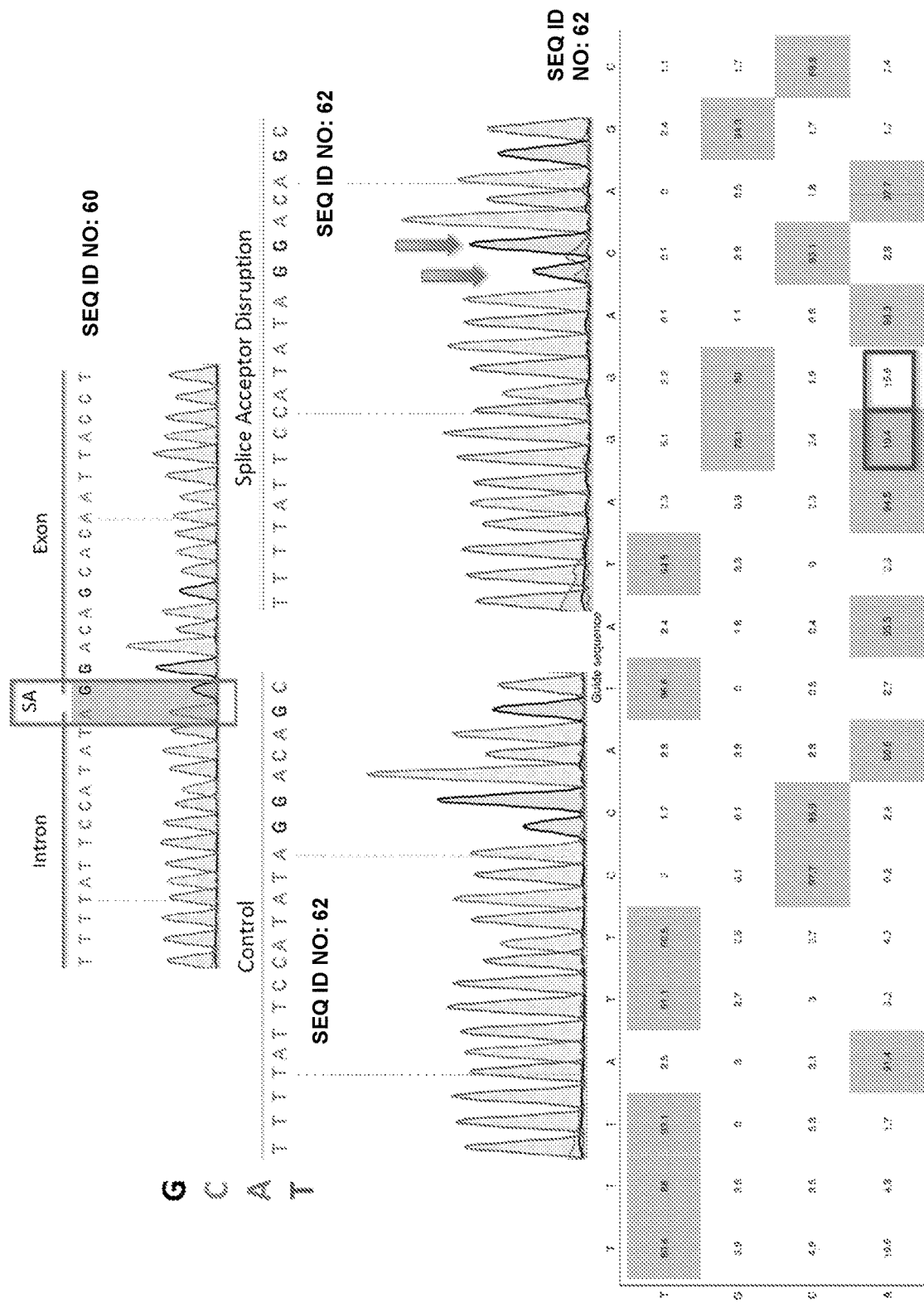
FIG. 24 depicts genomic sequencing data of control cells and cells electroporated with a gRNA (SEQ ID NO:55) designed to introduce a modification into a splice acceptor of NR3C1. The percent occurrence of a T, G, C, or A nucleotide at each position in the genome corresponding to the gRNA is shown.

Base editing was performed to disrupt a splice acceptor in NR3C1. Electroporation of Tregs with base editor mRNA and a guide RNA having a sequence set forth in SEQ ID NO:55 was performed. Sequencing of the genetic locus revealed that base editing resulted in editing of a adenosine (A) in the genomic sequence into a guanine (G), thereby resulting in a mutant GG splice acceptor site (FIGS. 23 and 24).

Figure 25:
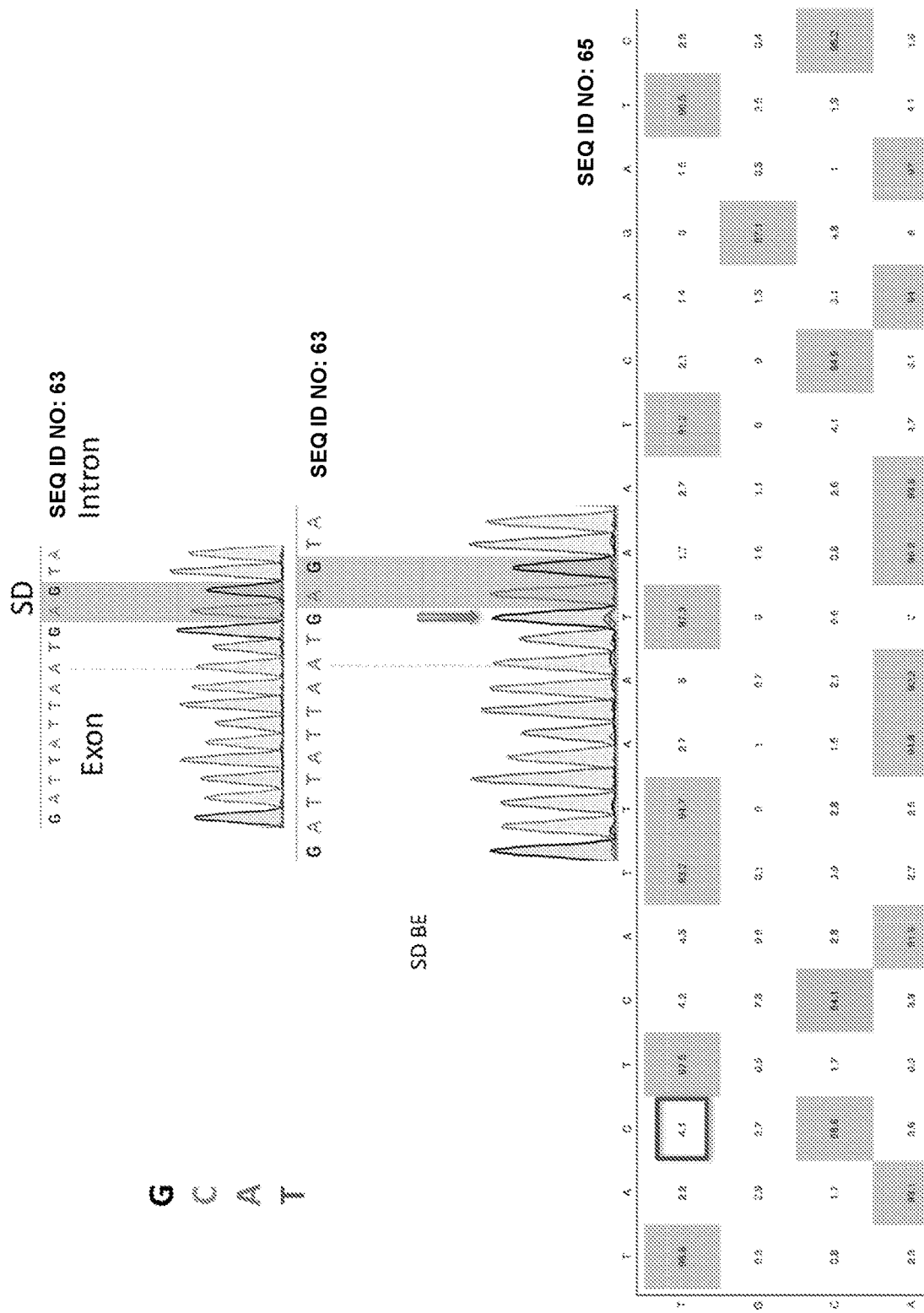
FIG. 25 depicts genomic sequencing data of control cells and cells electroporated with a gRNA (SEQ ID NO:56) designed to introduce a modification into a splice donor of NR3C1. The percent occurrence of a T, G, C, or A nucleotide at each position in the genome corresponding to the gRNA is shown.
Figure 26:
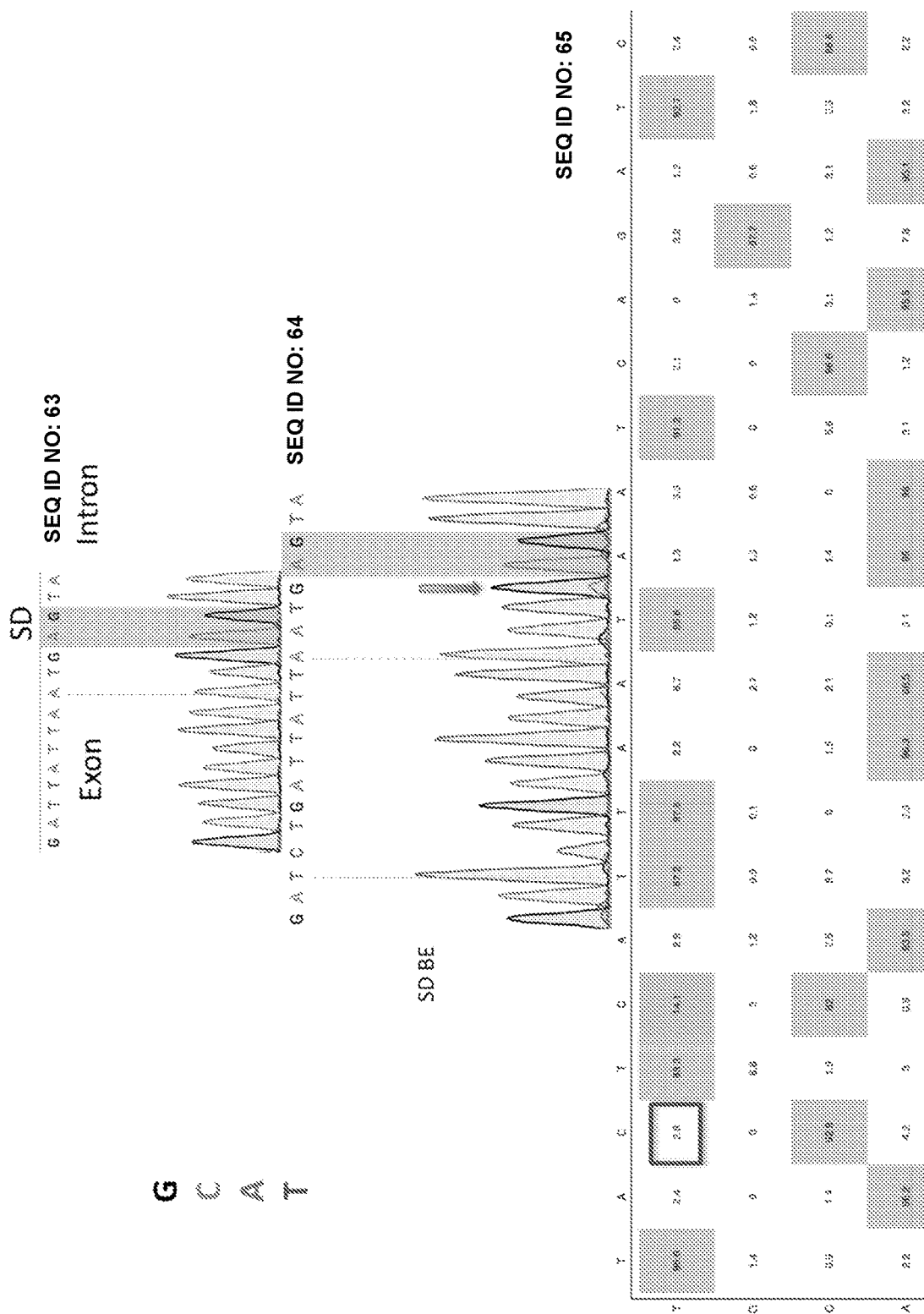
FIG. 26 depicts genomic sequencing data of control cells and cells electroporated with a gRNA (SEQ ID NO:56) designed to introduce a modification into a splice donor of NR3C1. The percent occurrence of a T, G, C, or A nucleotide at each position in the genome corresponding to the gRNA is shown.

Base editing was performed to disrupt a splice donor in NR3C1. Electroporation of Tregs with base editor mRNA and a guide RNA having a sequence set forth in SEQ ID NO:56 was performed. Sequencing of the genetic locus revealed that base editing resulted in editing of a guanine (G) in the genomic sequence into a adenosine (A), thereby resulting in a mutant splice donor site (FIGS. 25 and 26).

Example 10: Base Editing in Effector T Cells

Figure 27:
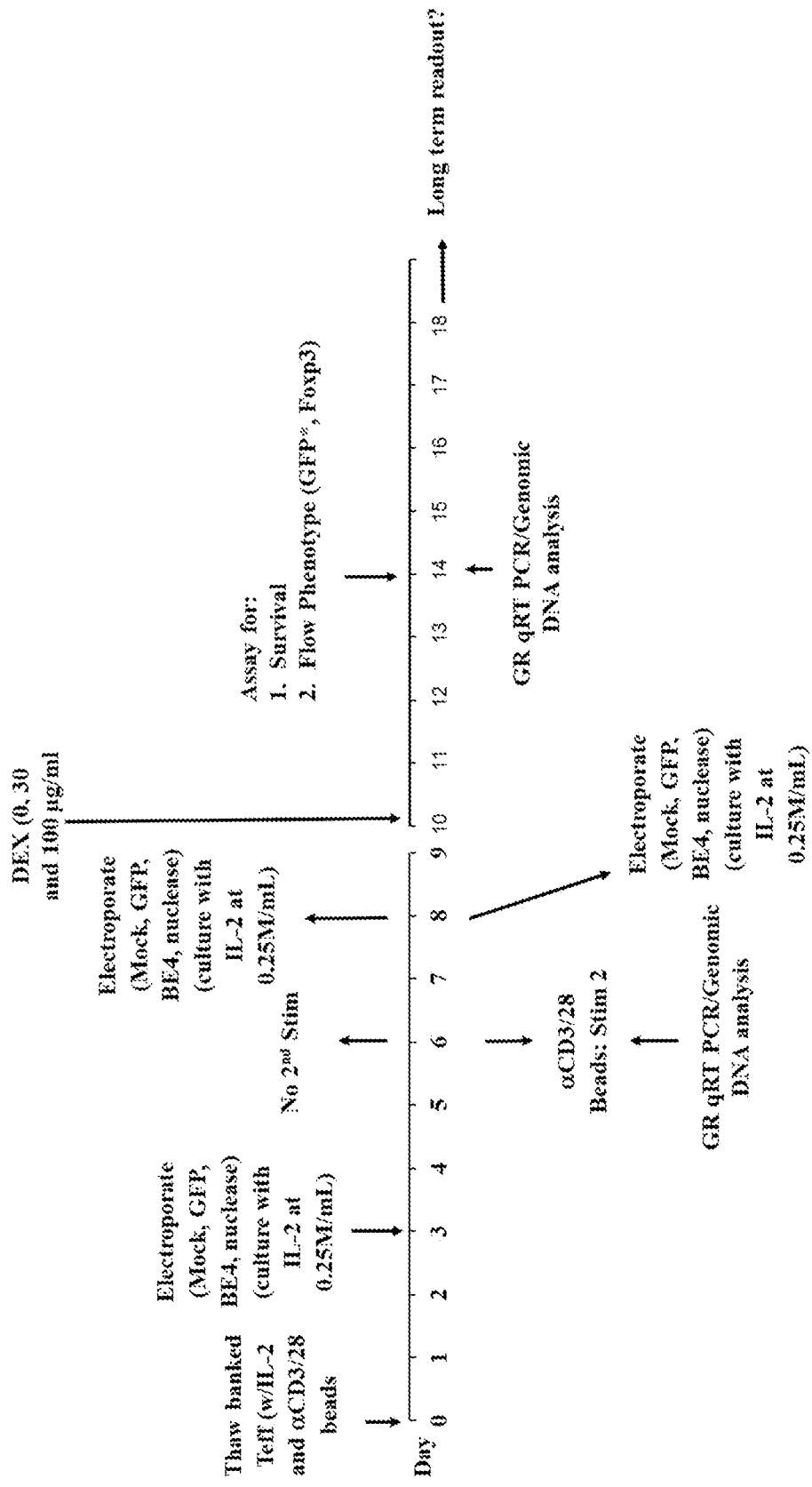
FIG. 27 depicts a general outline for two experiments. In one experiment, the glucocorticoid receptor locus was base editing in effector T cells (Teffs) using BE4, with two rounds of bead stimulation. In the second experiment, the glucocorticoid receptor locus was base editing in effector T cells using BE4, but with only one round of bead stimulation.
Figure 28:
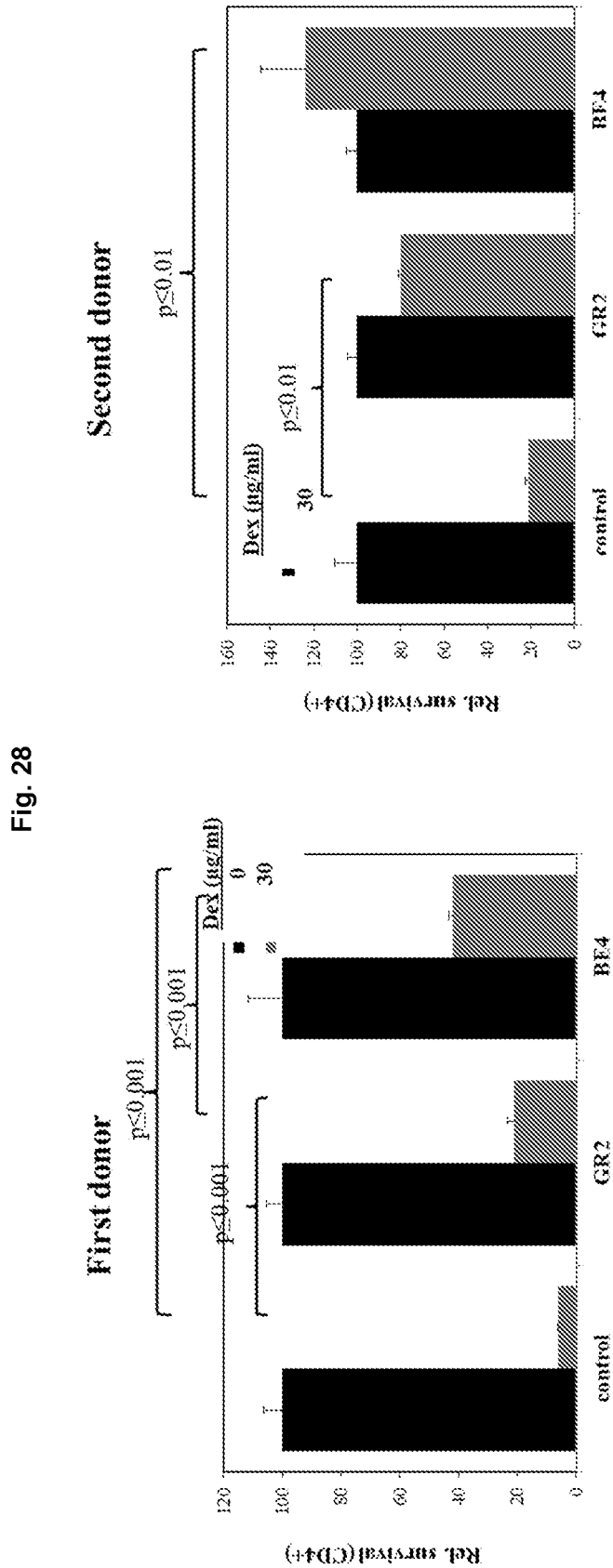
FIG. 28 depicts data showing the percent relative survival of CD4+ effector T cells (Teffs) following glucocorticoid receptor base editing from donors modified using gRNAs GR2 (SEQ ID NO: 8 in Table 1) or BE4 (SEQ ID NO:20 in Table 2) in the presence or absence of dexamethasone. The first donor's cells received two rounds of stimulation, and the second donor's cells received a single round of stimulation. Teffs receiving the two rounds of stimulation were very sensitive to Dexamethasone (Dex). Editing with two rounds of BE4 was more effective than GR2 at 30 µg/ml in both experiments (p≤0.001, p≤0.01, respectively).

Effector T cells (Teffs) were base edited by electroporation of the base editor as protein or mRNA encoding said base editor, along with a guide RNA to target bases for editing with said base editor. FIG. 27 depicts a general outline for two experiments. In one experiment, the glucocorticoid receptor locus was base editing in effector T cells (Teffs) using BE4, with two rounds of bead stimulation. In the second experiment, the glucocorticoid receptor locus was base editing in effector T cells using BE4, but with only one round of bead stimulation. FIG. 28 depicts data showing the percent relative survival of CD4+ effector T cells (Teffs) following glucocorticoid receptor base editing from donors modified using gRNAs GR2 (SEQ ID NO:8 in Table 1) or BE4 (SEQ ID NO:20 in Table 2) in the presence or absence of dexamethasone. The first donor's cells received two rounds of stimulation, and the second donor's cells received a single round of stimulation. Teffs receiving the two rounds of stimulation were very sensitive to Dexamethasone (Dex). Editing with two rounds of BE4 was more effective than GR2 at 30 µg/ml in both experiments (p≤0.001, p≤0.01, respectively).

What is claimed:

1. A method for generating a modified cell, comprising:
   introducing a gene editing system into a regulatory T (Treg) cell that produces a modification in an exon, a splice donor, or a splice acceptor of a gene locus encoding for NR3C1, wherein the modification downregulates gene expression of NR3C1 and renders the modified cell steroid-resistant; and
   inserting an exogenous calcineurin inhibitor resistance gene into the genome of the cell to render the modified cell calcineurin inhibitor (CNI)-resistant,
   thereby generating a modified Treg cell.

2. The method of claim 1, wherein the modification is an indel in exon 2 of NR3C1.

3. The method of claim 1, wherein the gene editing system is a CRISPR system.

4. The method of claim 3, wherein the CRISPR system comprises a guide RNA that comprises a nucleic acid sequence set forth in any one of SEQ ID NOs: 7-10.

5. The method of claim 3, wherein the CRISPR system comprises a guide RNA that comprises a nucleic acid sequence set forth in SEQ ID NO:8.

6. The method of claim 3, wherein the CRISPR system comprises a base editor and a guide RNA.

7. The method of claim 1, wherein the modification introduces a premature stop codon in NR3C1, thereby resulting in downregulated gene expression of NR3C1.

8. The method of claim 6, wherein the guide RNA comprises a nucleic acid sequence set forth in any one of SEQ ID NOs: 17-54.

9. The method of claim 3, wherein the inserting of the exogenous calcineurin inhibitor resistance gene into the genome of the cell occurs at the site of the indel in a gene locus encoding NR3C1.

10. The method of claim 3, wherein the calcineurin inhibitor resistance gene is a mutant form of a Calcineurin A (CNa) gene selected from the group consisting of PPP3Ca, PPP3Cb and PPP3Cc, a mutant form of the Calcineurin B (CNb) gene selected from the group consisting of PPP3R1 and PPP3R2, or a nucleic acid encoding a calcineurin variant protein selected from the group consisting of CNa12, CNa22, and CNb30.

11. The method of claim 1, wherein the modified cell is allogeneic to a human subject.

12. The method of claim 11, wherein the human subject has received a stem cell transplant or a solid organ transplant or is a candidate for stem cell transplantation or for solid organ transplantation.

13. The method of claim 11, wherein the human subject is suffering from an autoimmune disorder or Graft vs. Host Disease (GVHD).

* * * * *